(12) United States Patent  
de Sauvage et al.

(10) Patent No.: US 7,811,777 B2  
(45) Date of Patent: Oct. 12, 2010

(54) METHODS OF SCREENING FOR AGONISTS AND ANTAGONISTS OF PATCHED-2

(75) Inventors: Frederic J. de Sauvage, Foster City, CA (US); David A. Carpenter, San Francisco, CA (US)

(73) Assignee: Genentech Inc., South San Francisco, CA (US)

(*) Notice: Subject to any disclaimer, the term of this patent is extended or adjusted under 35 U.S.C. 154(b) by 165 days.

(21) Appl. No.: 11/538,748

(22) Filed: Oct. 4, 2006

(65) Prior Publication Data

US 2007/0049730 A1 Mar. 1, 2007

Related U.S. Application Data

(63) Continuation of application No. 09/990,046, filed on Nov. 20, 2001, which is a continuation of application No. 09/293,505, filed on Apr. 15, 1999, now Pat. No. 6,348,575.

(60) Provisional application No. 60/081,884, filed on Apr. 15, 1998.

(51) Int. Cl.
*G01N 33/567* (2006.01)
*C07K 14/72* (2006.01)
*C12P 19/00* (2006.01)
*C12N 15/09* (2006.01)
*C12N 5/07* (2006.01)

(52) U.S. Cl. .................. 435/7.21; 530/350; 530/387.3; 435/320.1; 435/325; 435/348

(58) Field of Classification Search ................ None
See application file for complete search history.

(56) References Cited

U.S. PATENT DOCUMENTS

| 4,816,567 | A |   | 3/1989 | Cabilly et al. |
|---|---|---|---|---|
| 5,225,539 | A |   | 7/1993 | Winter |
| 5,844,079 | A | * | 12/1998 | Ingham et al. ............ 530/350 |
| 5,932,448 | A |   | 8/1999 | Tso et al. |
| 6,261,786 | B1 | * | 7/2001 | Marigo et al. ............ 435/7.1 |

FOREIGN PATENT DOCUMENTS

| EP |   | 0 879 888 | 11/1998 |
|---|---|---|---|
| WO |   | WO 95/18856 | 7/1995 |
| WO |   | WO 96/11260 | 4/1996 |
| WO |   | WO 97/45541 | 12/1997 |
| WO |   | WO 99/29854 | 6/1999 |

OTHER PUBLICATIONS

Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Smith et al (1997) Nature Biotechnology 15:1222.*
Brenner (1999) Trends in Genetics 15(4): 132.*
Bork et al (1996) Trends in Genetics 12(10): 425.*
Wang et al. (1999) Nuc Acids Res. 27: 4609-4618.*
Kaufman et al (1999) Blood 94: 3178-3184.*
Campbell et al. (1997) Theriology 47(1): 63-72.*
Boitani et al, 1993. Biology of Reproduction. 48: 761-767.*
Burry, Richard W., "Specificity Controls for Immunocytochemical Methods" *J. of Histochemistry & Cytochemistry* 48(2):163-165 (2000).
Van Regenmortel, M.H.V., "From absolute to exquisite specificity. Reflections on the fuzzy nature of species, specificity and antigenic sites" *J. of Immunological Methods* 216:37-48 (1998).
U.S. Appl. No. 09/031,563, filed Feb. 26, 1998, Zhang et al.
Alcedo et al., "The Drosophila Smoothened Gene Encodes a Seven-Pass Membrane Protein, A Putative Receptor for the Hedgehog Signal." *Cell.* 86:221-232 (1996).
Apelqvist et al., "Sonic Hedgehog Directs Specialised Mesoderm Differentiation in the Intestine and Pancreas." *Current Biology.* 7(10):801-804 (Oct. 1, 1997).
Bellusci et al., "Involvement of Sonic Hedgehog (Shh) in Mouse Embryonic Lung Growth and Morphogenesis." *Development.* 124(1):53-63 (Jan. 1997).
Bitgood et al., "Hedgehog and Bmp genes are coexpressed at many diverse sites of cell-cell interaction in the mouse embryo" *Developmental Biology* 172(1):126-138 (Nov. 1995).
Bitgood et al., "Sertoli Cell Signaling by Desert Hedgehog Regulates the Male Germline." *Current Biology.* 6(3):298-304 (1996).
Bork, et al., "Go hunting in sequence databases but watch out for the traps" *Trends in Genetics* 12(10):425-427 (Oct. 1996).
Bork, P., "Powers and Pitfalls in Sequence Analysis: The 70% Hurdle" *Genome Research* 10(4):398-400 (Apr. 2000).
Bowie et al., "Deciphering Science the Message in Protein Sequences: Tolerance to Amino Acid Substitutions" *Science* 247:1306-1310 (1990).
Brenner, S.E., "Errors in genome annotation" *Trends in Genetics* 15(4):132-133 (Apr. 1999).
Carpenter et al., "Characterization of Two Patched Receptors for the Vertebrate Hedgehog Protein Family." *Proc. Natl. Acad. Sci. USA* 95(23):13630-13634 (1998).
Chen and Struhl., "Dual Roles for Patched in Sequestering and Transducing Hedgehog." *Cell.* 87(3):553-563 (Nov. 1, 1996).
Concordet et al. *Development* 122:2835-2846 (Feb. 1996).
de Jong et al., "Pathogenesis of adult testicular germ cell tumors. A cytogenetic model" *Cancer Genetics & Cytogenetics* 48(2):143-167 (Sep. 1990).
Doerks, et al., "Protein annotation: detective work for function prediction" *Trends in Genetics* 14(6):248-250 (Jun. 1998).

(Continued)

*Primary Examiner*—Bridget E Bunner
*Assistant Examiner*—Zachary C Howard
(74) *Attorney, Agent, or Firm*—Patrick J. Farley

(57) ABSTRACT

The present invention relates to nucleotide sequences, including expressed sequence tags (ESTs), oligonucleotide probes, polypeptides, antibodies, vectors and host cells expressing, immunoadhesins, agonists and antagonists to patched-2.

13 Claims, 29 Drawing Sheets

OTHER PUBLICATIONS

Echelard et al., "Sonic Hedgehog, A Member of a Family of Putative Signaling Molecules, is Implicated in the Regulation of CNS Polarity." *Cell*. 75:1417-1430 (1993).

Ericson et al., "Sonic Hedgehog Induces the Differentiation of Ventral Forebrain Neurons: A Common Signal for Ventral Patterning Within the Neural Tube." *Cell*. 81(5):747-756 (Jun. 2, 1995).

Fan and Tessier-Lavigne., "Patterning of Mammalian Somites by Surface Ectoderm and Notochord: Evidence for Sclerotome Induction by a Hedgehog Homolog." *Cell*. 79(7):1175-1186 (Dec. 30, 1994).

Fujiwara et al. *Human EST* (GeneBank Accession No. D60589) (May 21, 1996).

Gailani et al., "The Role of the Human Homologue of Drosophila Patched in Sporadic Basal Cell Carcinomas." *Nature Genetics*. 14:78-81 (Sep. 1996).

Goodrich et al., "Conservation of the Hedgehog/Patched Signaling Pathway from Flies to Mice: Induction of a Mouse Patched Gene by Hedgehog." *Genes Dev.* 10(3):301-312 (1996).

Hahn et al., "Mutations of the Human Homolog of Drosophila Patched in the Nevoid Basal Cell Carcinoma Syndrome" *Cell* 85:841-851 (1996).

Hynes et al., "Control of Cell Pattern in the Neural Tube by the Zinc Finger Transcription Factor and Oncogene Gli-1." *Neuron*. 19(1):15-26 (Jul. 1997).

Johnson et al., "Ectopic Expression of Sonic Hedgehog Alters Dorsal-Ventral Patterning of Somites." *Cell*. 79:1165-1173 (1994).

Johnson et al., "Human Homolog of Patched, a Candidate Gene for the Basal Cell Nevus Syndrome" *Science* 272:1668-1671 (1996).

Jones et al., "Replacing the Complementarity-Determining Regions in a Human Antibody with Those From a Mouse" *Nature* 321(6069):522-525 (May 29, 1986).

Krauss et al., "A Functionally Conserved Homolog of the Drosophila Segment Polarity Gene hh is Expressed in Tissues with Polarizing Activity in Zebrafish Embryos." *Cell*. 75:1431-1444 (1993).

Laufer et al., "Sonic Hedgehog and Fgf-4 Act Through a Signaling Cascade and Feedback Loop to Integrate Growth and Patterning of the Developing Limb Bud." *Cell*. 79(6):993-1003 (Dec. 16, 1994).

Liddell et al. *Antibody Technology*, BIOS Scientific Publishers pps. 9-24 and 85-102 (1995).

Marigo et al., "Biochemical Evidence that Patched is the Hedgehog Receptor." *Nature*. 384(6605):176-179 (Nov. 14, 1996).

Marigo et al., "Conservation in hedgehog signaling: induction of a chicken patched homolog by Sonic hedgehog in the developing limb" *Development* 122:1225-1233 (1996).

Marti et al., "Requirement of 19K Form of Sonic Hedgehog for Induction of Distinct Ventral Cell Types in CNS Explants." *Nature*. 375(6529):322-325 (May 25, 1995).

Morrison et al., "Chimeric Human Antibody Molecules: Mouse Antigen-Binding Domains with Human Constant Region Domains" *Proc. Natl. Acad. Sci. USA* 81(21):6851-6855 (Nov. 1984).

Motoyama et al., "Ptch2, a second mouse Patched gene is co-expressed with Sonic hedgehog." *Nature Genetics* 18(2):104-106 (Feb. 1998).

Nakano et al., "A protein with several possible membrane-spanning domains encoded by the Drosophila segment polarity gene patched" *Nature* 341:508-513 (1989).

Ngo et al., "The Protein Folding Problem and Tertiary Structure" *Computational Complexity Protein Structure Prediction, and the Levinthal Paradox*, Chapter 14, pp. 492-495 (Mar. 2, 1995).

Nusslein-Volhard et al., "Mutations Affecting the Pattern of the Larval Cuticle in Drosophila Melanogaster" *Roux's Archives of Developmental Biology* 193(5):267-282 (1984).

Oro et al., "Basal Cell Carcinomas in Mice Overexpressing Sonic Hedgehog." *Science*. 276(5313):817-821 (May 2, 1997).

Perrimon, N., "Hedgehog and Beyond." *Cell*. 80:517-520 (Feb. 1995).

Presta, L., "Antibody Engineering" *Current Opinion in Structural Biology* 2:593-596 (1992).

Rassoulzadegan et al., "Transmeiotic differentiation of male germ cells in culture" *Cell* 75(5):997-1006 (Dec. 3, 1993).

Riddle et al., "Sonic Hedgehog Mediates the Polarizing Activity of the ZPA." *Cell*. 75:1401-1416 (1993).

Riechmann et al., "Reshaping Human Antibodies for Therapy" *Nature* 332:323-327 (Mar. 24, 1988).

Roberts et al., "Sonic Hedgehog is an Endodermal Signal Inducing Bmp-4 and Hox Genes During Induction and Regionalization of the Chick Hindgut." *Development*. 121:3163-3174 (1995).

Skolnick et al., "From Genes to protein structure and function: novel applications of computational approaches in the genomic era" *Trends in Biotechnology* 18(1):34-39 (Jan. 2000).

Smith, et al., "The challenges of genome sequence annotation or "The devil is in the details"" *Nature Biotechnology* 15(12):1222-1223 (Nov. 1997).

Stone et al., "The Tumour-Suppressor Gene Patched Encodes a Candidate Receptor for Sonic Hedgehog." *Nature*. 384(14):129-134 (Nov. 1996).

Summersgill et al., "Molecular cytogenetic analysis of adult testicular germ cell tumours and identification of regions of consensus copy number change" *British Journal of Cancer* 77(2):305-313 (1998).

Symth et al. *Human Molecular Genetics* 8(2):291-297 (1999).

Takabatake et al., "Hedgehog and patched gene expression in adult ocular tissues" *FEBS Letters* 410:485-489 (1997).

van den Heuvel and Ingham, "Smoothened Encodes a Receptor-Like Serpentine Protein Required for Hedgehog Signalling" *Nature* 382:547-551 (1996).

Vortkamp et al., "Regulation of rate of cartilage differentiation by Indian hedgehog and PTH-related protein" *Science* 273:613-622 (1996).

Wallis, G., "Bone growth: Coordinating chondrocyte differentiation" *Current Biology* 6(12):1577-1580 (1996).

Wells, J. A., "Additivity of Mutational Effects in Proteins" *Biochemistry* 29(37):8509-8517 (Sep. 18, 1990).

Wicking and Bale, "Molecular basis of the nevoid basal cell carcinoma syndrome" *Current Opinion in Pediatrics* 9:630-635 (1997).

Xie et al., "Activating Smoothened Mutations in Sporadic Basal-Cell Carcinoma." *Nature*. 391(6662):90-92 (Jan. 1, 1998).

Xie et al., "Mutations of the PATCHED gene in several types of sporadic extracutaneous tumors" *Cancer Research* 57(12):2369-2372 (Jun. 15, 1997).

Zaphiropoulos et al., "PTCH2, a novel human patched gene undergoing alternative splicing and up-regulated in basal cell carcinomas" *Cancer Research* 59:787-792 (1999).

* cited by examiner

```
  1 GTTATTTCAG GCCATGGTGT TGCGCCGAAT TAATTCCCGA TCCAGACATG ATAAGATACA TTGATGAGTT TGGACAAACC ACAACTAGAA TGCAGTGAAA
    CAATAAAGTC CGGTACCACA ACGCGGCTTA ATTAAGGGCT AGGTCTGTAC TATTCTATGT AACTACTCAA ACCTGTTTGG TGTTGATCTT ACGTCACTTT
    SEQ ID NO: 1

101 AAAATGCTTT ATTTGTGAAA TTTGTGATGC TATTGCTTTA TTTGTAACCA TTATAAGCTG CAATAAACAA GTTGGGCCAT GTTGGGCCAA CTTCTGCAGG
    TTTTACGAAA TAAACACTTT AAACACTACG ATAACGAAAT AAACATTGGT AATATTCGAC GTTATTTGTT CAACCCGGTA CAACCCGGTT GAAGACGTCC

201 TCGACTCTAG AGGATCCCCG GGGAATTCCG ATCGCCGCCC CTCAGAGAGC TGCCCCCGAG TTACACACCC CCGCAGCACC
    AGCTGAGATC TCCTAGGGGC CCCTTAAGGC TAGCGGCGGG GAGTCTCTCG ACGGGGGCTC AATGTGTGGG GGCGTCGTGG
  1                                                    M T R S P P L R E L P P S Y T P P A R T A A P
    SEQ ID NO: 2

301 CCAGATCCTA GCTGGAGCC TGAAGGCTCC ACTCTGGCTT CGTGCTTACT TCCAGGGCCT GCTCTTCTCT CTGGGATGCG GGATCCAGAG ACATTGTGGC
    GGTCCTGGAT CGACCCTCGG ACTTCCGAGG TGAGACCGAA GCACGAATGA AGGTCCCGGA CGAGAAGAGA GACCCTACGC CCTAGGTCTC TGTAACACCG
    ^ insert starts here
 24  Q I L A G S L K A P L W L R A Y F Q G L L F S L G C G I Q R H C G 401 AAAGTGCTCT TTCTGGGACT GTTGGCCTTT GGGGCCCTTT CATTAGGTCT CCGCATGGCT GAGGCTGCAT CAAACTTGGA ATTATTGAGA GTAGAAGTGG
    TTTCACGAGA AAGACCCTGA CAACCGGAAA CCCCGGGAAA GTAATCCAGA GGCGTACCGA CTCCGACGTA GTTTGAACCT TAATAACTCT CATCTTCACC
 57  K V L F L G L L A F G A L A F G A L A L G L R M A E A A S Q L W V E V G 501 GCAGCCGGGT GAGCCAGGAG CTCGGTCCTC GACGTAATGT GGTTCCTCTC CAAGGAGAAA GCTGGGGGAG CAGGCAGCCC TCACTGCCAG GATGCTGATA CAGACCGCAC GCCAGGAGGG
    CGTCGGCCCA CTCGGTCCTC GAGCCAGGAG CTGCATTACA CCAAGGAGAG GTTCCTCTTT CGACCCCCTC GTCCGTCGGG AGTGACGGTC CTACGACTAT GTCTGGCGTG CGGTCCTCCC
 91  S R V S Q E L H Y T K E K L G E E A A Y T S Q M L I Q T A R Q E G 601 AGAGAACATC CTCACACCCG AAGCACTTGG CCTTCCACCTC CAGGCAGCCC TCACTGCCAG GTATCACTCT ATGGGAAGTC CTGGGATTTG
    TCTCTTGTAG GAGTGTGGGC TTCGTGAACC GGAGGTGGAG GTCCGTCGGG AGTGACGGTC CATAGTGAGA TACCCTTCAG GACCCTAAAC
124  E N I L T P E A L G L H L Q A A L T A S K V Q V S L Y G K S W D L 701 AACAAAATCT GCTACAAGTC AGGAGTTCCC TCCTCAAGGG CTTATTGAAA ATGGAATGAT TGAGTGGATG ATTGAGAAGC TGTTTCCGTG CGTGATCCTC ACCCCCCTCG
    TTGTTTTAGA CGATGTTCAG TCCTCAAGGG AGGAGTTCCC GAATAACTTT TACCTTACTA ACTCACCTAC TAACTCTTCG ACAAAGGCAC GCACTAGGAG TGGGGGGAGC
157  N K I C Y K S G V P L I E N G M I E W M I E K L F P C V I L T P L D
```

FIG._1A

```
801  ACTGCTTCTG GGAGGGAGCC AAACTCCAAG GGGGCTCCGC CTACCTGCCC GGCCGCCCCG GGCCGCGCCC GATATCCAGTG GACCAACCTG GATCCAGAGC AGCTGCTGGA
     TGACGAAGAC CCTCCCTCGG TTTGAGGTTC CCCGAGGGCG GATGGACGGG CCGGCGGGGC TATAGGTCAC CTGGTTGGAC CTAGGTCTCG TCGACGACCT
191   C  F  W   E  G  A   K  L  Q   G  G  S   A  Y  L   P  G  R   P  D  I   Q  W  T   N  L  D   P  E  Q   L  L  E

901  GGAGCTGGGT CCCTTTGCCT CCCTTGAGGG CTGCTAGACA AGGCACAGGT GGGCCAGGCC TACGTGGGGC GGCCCTGTCT GCACCCTGAT
     CCTCGACCCA GGGAAACGGA GGGAACTCCC GACGATCTGT TCCGTGTCCA CCCGGTCCGG ATGCACCCCG CCGGGACAGA CGTGGGACTA
224   E  L  G   P  F  A   S  L  E   G  F  R   E  L  L   D  K  A   Q  V  G   Q  A  Y   V  G  R   P  C  L   H  P  D

1001 GACCTCCACT GCCCACCTAG TGCCCCCAAC CATCACAGCA GGCAGGCTCC CAATGTGGCT CACGAGCTGA GTGGGGGCTG CCATGGCTTC TCCCACAAAT
     CTGGAGGTGA CGGGTGGATC ACGGGGGTTG GTAGTGTCGT CCGTCCGAGG GTTACACCGA GTGCTCGACT CACCCCCGAC GGTACCGAAG AGGTGTTTA
257   D  L  H   C  P  P   S  A  P   N  H  H   S  R  Q   A  P  N   V  A  H   E  L  S   G  G  C   H  G  F   S  H  K  F

1101 TCATGCACTG GCAGGAGGAA TTGCTGCTGG GGGTGACTAT CAGAGACCCC CAGAGACCCC CAAGGAGAGC AGAGGCCCTG TGCTGAGGGC CAGAGCACCT TCTTGCTGAT
     AGTACGTGAC CGTCCTCCTT AACGACGACC CCCACTGATA GTCTCTGGGG GTCTCTGGGG GTTCCTCTCG TCTCCGGGAC ACGACTCCCG GTCTCGTGGA AGAACGACTA
291   M  H  W   Q  E  E   L  L  L   G  M  A   R  D  P   Q  G  E   L  R  A   E  A  L   Q  S  T   F  L  L  M

1201 GAGTCCCCGC CAGCTGTACG AGCATTTCCG CAGGTGAGAG ACATTGGCTG GAGTGAGGAG CTCACTCCTC AGCCTTCTCC TCGGGGACCC CAGGCCAGCA CAGTGCTACA AGCCTGGCAG
     CTCAGGGGCG GTCGACATGC TCGTAAAGGC GTCCACTCTC TGTAACCGAC CTCACTCCTC GAGTGAGGAG AGGGCCTGGG GTCCGGTCGT GTCACGATGT TCGGACCGTC
324   S  P  R   Q  L  Y   E  H  F   R  Q  T   H  D  I   G  W  S   E  E  Q   A  S  T   V  L  Q   A  W  Q

1301 CGGGCGTTTG TGCAGCTGGC CCAGGAGGCC ACGTGCGACC GGTCCTCCCG GTGTGACCAT GCAGATCCAT CGTCTAGGTA CGGAAGAGGA GCCTTCTCCT CCACCACCCT GGATGACATC CTGCATGCGT
     GCCCGCAAAC ACGTCGACCG GGTCCTCCGG TGCACGCTGG CCAGGAGGGC CACACTGGTA GCAGATCCAT GCAGATCCAT CGGAAGAGGA GCCTTCTCCT CCACCACCCT GGATGACATC CTGCATGCGT
357   R  R  R   F  V  Q   L  A  Q   E  A  P   E  N  L   P  E  N   A  S  Q   Q  I  H   A  F  S   S  T  T   L  D  D   I  L  H  F

1401 TCTCTGAAGT CAGTGCTGCC CGTGTGGTGC GAGGCTATCT GCCTATGCCT GTGTGACCAT GCTGCGCCC AGTCCCAGGG
     AGAGACTTCA GTCACGACGG GCACACCACG CTCCGATAGA CGGATACGGA CACACTGGTA CGACGCGGG TCAGGGTCCC
391   S  E  V   S  A  A   R  V  V   G  Y  L   L  M  L   A  Y  A   C  V  T   M  L  R   W  D  C   A  Q  S   Q  G

1501 TTCCGTGGGC CTTGCTGCTG GGGCAGCGGT GGCCCTGGGC GTGGCCCTG CGGAAGCGGG GGCCCTGGG GGCCCTGGCT CTCGGACATCA CCTTCAATGC TGCCACTACC
     AAGGCACCCG GAACGACGAC CCCGTCGCCA CCGGGACCCG CACCGGGAC GCCTTGCCC CCGGACCC CCGGGACCGA GAGCCTAGT GGAAGTTACG ACGGTGATGG
424   S  V  G   L  A  G   V  L  L   V  A  L   A  V  A   S  G  L   G  L  C   A  L  L   G  I  T   F  N  A   A  T  T
```

FIG._1B

```
1601  CAGGTGCTGC CTTTCTTTGGC TCTGGGAATC GGCGTGGATG ACGTATTCCT GCCTTCACAG AGGCTCTGCC TGGCACCCCT CTCCAGGAGC
      GTCCACGACG GAAAGAACCG AGACCCTTAG CCGCACCTAC TGCATAAGGA CGGAAGTGTC TCCGAGACGG ACCGTGGGGA GAGGTCCTCG
457    Q  V  L  P   F  L  A    L  G  I    G  V  D  D   V  F  L    A  H     A  F  T  E   A  L  P    G  T  P    L  Q  E  R

1701  GCATGGGCGA GTGTCTGCAG CGCACGGGCA CCAGTGTCGT ACTCACATCC ATCAACAACA TGGCCGCCTT CCTCATGGCT GCCCTCGTTC CCATCCCTGC
      CGTACCCGCT CACAGACGTC GCGTGCCCGT GGTCACAGCA TGAGTGTAGG TAGTTGTTGT ACCGGCGGAA GGAGTACCGA CGGGAGCAAG GGTAGGGACG
491    M  G  E   C  L  Q    R  T  G  T    S  V  V    L  T  S    I  N  N  M    A  A  F    L  M  A    A  L  V  P    I  P  A

1801  GCTGCGAGCC TTCTCCCTAC AGGCGGCCAT AGTGGTTGGC TGCACCTTTG TAGCCGTGAT GCTTGTCTTC CCAGCCATCC TCAGCCTGGA CCTACGGCGG
      CGACGCTCGG AAGAGGGATG TCCGCCGGTA TCACCAACCG ACGTGGAAAC ATCGGCACTA CGAACAGAAG GGTCGGTAGG AGTCGGACCT GGATGCCGCC
524    L  R  A   F  S  L  Q    A  A  I    V  V  G    C  T  F  V    A  V  M    L  V  F    P  A  I  L   S  L  D    L  R  R

1901  CGCCACTGCC AGCGCCTTGA TGTGCTCTGC TGCTTCTCCA GTCCCTGCTC TGCTCAGGTG ATTCAGATCC TGCCCCAGGA GCTGGGGGAC GGGACAGTAC
      GCGGTGACGG TCGCGGAACT ACACGAGACG ACGAAGAGGT CAGGGACGAG ACGAGTCCAC TAAGTCTAGG ACGGGGTCCT CGACCCCCTG CCCTGTCATG
557    R  H  C  Q    R  L  D    V  L  C    C  F  S  S    P  C  S    A  Q  V    I  Q  I  L   P  Q  E    L  G  D    G  T  V  P

2001  CAGTGGGCAT TGCCCACCTC ACTGCCACAG TTCAAGCCTT TACCCACTGT GAAGCCCAGA GCCAGCATGT GGTCACCATC CTGCCTCCCC AAGCCCACCT
      GTCACCCGTA ACGGGTGGAG TGACGGTGTC AAGTTCGGAA ATGGGTGACA CTTCGGGTCT CGGTCGTACA CCAGTGGTAG GACGGAGGGG TTCGGGTGGA
591    V  G  I    A  H  L    T  A  T  V    Q  A  F    T  H  C    E  A  S  S    Q  H  V    V  T  I    L  P  P  Q    A  H  L

2101  GGTGCCCCCA CCTTCTGACC CACTGGGCTC TGAGCTCTTC AGCCCTGGAG GGTCCACACG GGACCTTCTA GGCCAGGAGG AGGAGACAAG GCAGAAGGCA
      CCACGGGGGT GGAAGACTGG GTGACCCGAG ACTCGAGAAG TCGGGACCTC CCAGGTGTGC CCTGGAAGAT CCGGTCCTCC TCCTCTGTTC CGTCTTCCGT
624    V  P  P    P  S  D  P   L  G  S    E  L  F    S  P  G  G   S  T  R    D  L  L    G  Q  E  E    T  R     Q  K  A

2201  GCCTGCAAGT CCCTGCCCTG TGCCCGCTGG AATCTTGCCC ATTTGCGCCG CTATCAGTTT CAGAAGACAG CGGGGCCAAG GCCATCGTGC
      CGGACGTTCA GGGACGGGAC ACGGGCGACC TTAGAACGGG TAAAGCGGGC GATAGTCAAA GTCTTCTGTC GCCCCGGTTC CGGTAGCACG
657    A  C  K  S    L  P  C    A  R  W    N  L  A  H    F  A  R    Y  Q  F    Q  K  T    A  G  P  R   P  S  C

2301  TGGTGCTCTT TGGTGCCCTA CTGGGCCTGA GCCTCTACGG AGCCACCTTG GTGCAAGACG GCCTGGCCCT GACGGATGTG GTGCCTCGGG GCACCAAGGA
      ACCACGAGAA ACCACGGGAT GACCCGGACT TCGGAGATGC TCGGTGGAAC CACGTTCTGC CGGACCGGGA CTGCCTACAC CACGGAGCCC CGTGGTTCCT
691    V  L  F    G  A  L    L  G  L  S    L  Y  G    A  T  L    V  Q  D  G   L  A  L    T  D  V    V  P  R  G    T  K  E
```

*FIG._1C*

```
2401  GCATGCCTTC CTGAGCGCCC AGCTCAGGTA CTTCTCCCTG TACGAGGTGG CCCTGGTGAC CCAGGGCTGG TTTGACTACG CCCATTCCCA ACGCGCCCTC
      CGTACGGAAG GACTCGCGGG TCGAGTCCAT GAAGAGGGAC ATGCTCCACC GGGACCACTG GGTCCCACCG AAACTGATGC GGGTAAGGGT TGCGCGGGAG
724   H  A  F   L  S  A   Q  L  R  Y   F  S  L   Y  E  V  A   L  V  T   Q  G  G   F  D  Y  A   H  S  Q    R  A  L

2501  TTTGATCTGC ACCAGCGCTT CAGTTCCCTC AAGGCGGTGC CTGCCCCACC GGCCACCCAG GCACCCCGCA CCTGGCTGCA CTATTACCGC AACTGGCTAC
      AAACTAGACG TGGTCGCGAA GTCAAGGGAG TTCCGCCACG ACGGGGTGGT CCGGTGGGTC CGTGGGGCGT GGACCGACGT GATAATGGCG TTGACCGATG
757   F  D  L  H   Q  R  F   S  S  L   K  A  V  L   P  P  P   A  T  Q   A  P  R  T   W  L  H   Y  Y  R   N  W  L  Q

2601  AGGGAATCCA GGCTGCCTTT GACCAGGACT GGGCTTCTGG CGCATCACC CTCTGAGGAT GGGGCCCTGG CCTACAAGCT
      TCCCTTAGGT CCGACGGAAA CTGGTCCTGA CCCGAAGACC GCGTAGTGG TGGCGTTACC CCCCGGGACC GGATGTTCGA
791   G  I  Q   A  A  F   D  Q  D  W   A  S  G   R  I  T   R  H  S  Y   R  N  G   S  E  D   G  A  L  A   Y  K  L

2701  GCTCATCCAG ACTGGAGACG CCCAGAGCC TCTGGATTTC AGCCAGCTGA CCACAAGGAA GCTGGTGGAC AGAGAGGGAC TGAATGGCTG CACGACAAAT
      CGAGTAGGTC TGACCTCTGC GGGTCCTCGG AGACCTAAAG TCGGTCGACT GGTGTTCCTT CGACCACCTG TCTCTCCCTG ACTTACCGAC GTGCTGTTTA
824   L  I  Q   T  G  D  A   Q  E  P   L  D  F   S  Q  L  T   T  R  K   L  V  D   R  E  G  L   I  P  P    E  L  F

2801  TACATGGGGC TGACCGTGTG GGTGAGCAGT GACCCCCTGG GTCTGGCAGC CTCACAGGCC AACTTCTACC CCCCACCTCC TGAATGGCTG CACGACAAAT
      ATGTACCCCG ACTGGCACAC CCACTCGTCA CTGGGGGACC CAGACCGTCG GAGTGTCCGG TTGAAGATGG GGGGTGGAGG ACTTACCGAC GTGCTGTTTA
857   Y  M  G  L   T  V  W   V  S  S   D  P  L  G   L  A  A   S  Q  A   N  F  Y  P   P  P  P   E  W  L    H  D  K  Y

2901  ACGACACCAC GGGGGAGAAC CTTCGCATCC GCCCTTGGAG TTTGCCCAGT TCCCCTTCCT GCTGCGTGGC CGACGCACCG GAGTCTTCT GACGTCTGAA
      TGCTGTGGTG CCCCCTCTTG GAAGCGTAGG CGGGAACCTC AAACGGGTCA AGGGGAAGGA CGACGCACCG GCTGCGTGGC CTCAGAAGA CTGCAGACTT
891   D  T  T   G  E  N   L  R  I  P   P  A  Q   F  A  Q  F   P  F  L   L  R  G   L  Q  K  T   A  D  F

3001  TGTGGAGGCC ATCGAGGGGG CCCGGGCAGC ATGCGCAGAG GCCGCCAGG CTGGGTGCA CGCCTACCCC AGCGGCTCCC CCTTCCTCTT CTGGGAACAG
      ACACCTCCGG TAGCTCCCCC GGGCCCGTCG TACGCGTCTC CGGCCGGTCC GACCCCACGT GCGGATGGGG TCGCCGAGGG GGAAGGAGAA GACCCTTGTC
924   V  E  A   I  E  G  A   R  A  A   C  A  E   A  G  Q  A   G  V  H   A  Y  P   S  G  S  P   F  L  F   W  E  Q

3101  TATCTGGGCC TGCGGCGCTG CTTCCTGCTG GCCGTCTGCA TCCTGCTGGT GTGCACTTTC CTCGTCTGTG CTCTGCTGCT CCTCAACCCC TGGACGGCTG
      ATAGACCCGG ACGCCGCGAC GAAGGACGAC CGGCAGACGT AGGAGGACGA CACGTGAAAG GAGCAGACAC GAGACGACGA GGAGTTGGGG ACCTGCCGAC
957   Y  L  G  L   R  R  C   F  L  L   A  V  C  I   L  L  V   C  T  F   L  V  C  A   L  L  L   L  N  P   W  T  A  G
```

FIG.–1D

```
3201 GCCTCATAGT GCTGGGTCCTG GCGATGATGA CAGTGGAACT CTTTGGTATC ATGGGTTTCC TGGGCATCAA GCTGAGTGCC ATCCCCGTGG TGATCCTTGT
     CGGAGTATCA CGACCAGGAC CGCTACTACT GTCACCTTGA GAAACCATAG TACCCAAAGG ACCCGTAGTT CGACTCACGG TAGGGGCACC ACTAGGAACA
 991  L   I   V   L   A   M   M   T   V   E   L   F   G   I   M   G   F   L   G   I   K   L   S   A   I   P   V   V   I   L   V

3301 GGCCTCTGTA GGCATTGGCG TTGAGTTCAC AGTCCACGTG GCTCTGGGCT TCCTGACCAC CCAGGGCAGC CGGAACCTGC GGGCCCGCCA TGCCCTTGAG
     CCGGAGACAT CCGTAACCGC AACTCAAGTG TCAGGTGCAC CGAGACCCGA AGGACTGGTG GGTCCCGTCG GCCTTGGACG CCCGGGCGGT ACGGGAACTC
1024  A   S   V   G   I   G   V   E   F   T   V   H   V   A   L   G   F   L   T   T   Q   G   S   R   N   L   R   A   A   H   A   L   E

3401 CACACATTTG CCCCCGTGAC CGATGGGGCC ATCTCCACAT TGCTGGGTCT GCTCATGCTT GCTGGTTCCC ACTTTGACTT CATTGTAAGG TACTTCTTTG
     GTGTGTAAAC GGGGGCACTG GCTACCCCGG TAGAGGTGTA ACGACCCAGA CGAGTACGAA CGACCAAGGG TGAAACTGAA GTAACATTCC ATGAAGAAAC
1057  H   T   F   A   P   V   T   D   G   A   I   S   T   L   L   G   L   L   M   L   A   G   S   H   F   D   F   I   V   R   Y   F   F   A

3501 CGGGCGCTGAC AGTGCTCACG CTCCTGGGCC TCCTCCATGG ACTCGTGCTG TGCTGTCCAT CCTGGGCCCG CCGGGTCTCC TGATACAGAT
     GCCCGCGACTG TCACGAGTGC GAGGACCCGG AGGAGGTACC TGAGCACGAC ACGACAGGTA GGACCCGGGC GGCCCAGAGG ACTATGTCTA
1091  A   L   T   V   L   T   L   L   G   L   L   H   G   L   V   L   L   P   V   L   S   I   L   G   P   P   P   E   V   I   Q   M

3601 GTACAAGGAA AGCCCAGAGA TCCTGAGTCC ACCAGCTCCA CAGGGAGGCG GGCTTAGGTG CCCAGAGCTT TGCCAGAGTG
     CATGTTCCTT TCGGGTCTCT AGGACTCAGG TGGTCGAGGT GTCCCTCCGC CCGAATCCAC CCCCCGTAGG AGGAGGGACG GGGTCTCGAA ACGGTCTCAC
1124  Y   K   E   S   P   E   I   L   S   P   P   A   P   Q   G   G   G   L   R   W   G   A   S   S   L   P   Q   S   F   A   R   V

3701 ACTACCTCCA TGACCGTGCC CATCCACCCA CCCCCCCTGC CTGGTGCCTA CATCCATCCA GCCCCCTGATG AGCCCCTTG GTCCCCTGCT GCCACTAGCT
     TGATGGAGGT ACTGGCACGG GTAGGTGGGT GGGGGGGACG GACCACGGAT GTAGGTAGGT CGGGGACTAC TCGGGGAAC CAGGGGACGA CGGTGATCGA
1157  T   T   S   M   T   V   A   I   H   P   P   P   L   P   G   A   Y   I   H   P   A   P   D   E   P   P   W   S   P   A   A   T   S   S

3801 CTGGCAACCT CAGTTCCAGG GGACCAGGTC CAGCCACTGG GTGAAAGAGC AGCTGAAGCA CAGAGACCAT GTGTGGGGCG TGTGGGGTCA CTGGGAAGCA
     GACCGTTGGA GTCAAGGTCC CCTGGTCCAG GTCGGTGACC CACTTTCTCG TCGACTTCGT GTCTCTGGTA CACACCCCGC ACACCCCAGT GACCCTTCGT
1191  G   N   L   S   S   R   G   P   G   P   A   T   G
                                                1203

3901 CTGGGTCTGG TGTTAGAGCC CCTGGAGGGC CCTGCTGCTG CTGCATCCCC TCTCCCGACC CAGCTGTCAT GGGCCTCCCT GATATCGAAT
     GACCCAGACC ACAATCTCGG GGACCTCCCG GGACGACGAC GACGACGACGTAGGGGG AGAGGGCTGG GTCGACAGTA CCCGGAGGGA CTATAGCTTA
                      ^ T to C                  (silent)                          pRK follows, this is the 5prime end of vector^

4001 TCAATCGATA GAACCGAGGT GCAGTTGGAC
     AGTTAGCTAT CTTGGCTCCA CGTCAACCTG
```

FIG._1E

SEQ ID NO: 3
```
                      30        40        50        60        70
905531        GCTGGGGTGCACGCCTACCNCAGCGGNTCCCCCTTCCTCTTCTGGGAACA
               : : :  : :    :   ******  *****  ******************  **
hpatched      CTGGGGCTGTCCAGTTACCCCAACGGCTACCCCTTCCTCTTCTGGGAGCA
                 3010      3020      3030      3040      3050
```
SEQ ID NO: 4
```
                      80        90       100       110       120
905531        GTATCTGGGCCTGCGGCGCTGCTTCCTGCTGGCCGTCTGCATCCTGCTGG
               ***  *  *****  **  *  ***   *  ******    *  **  **  *   **  ***
hpatched      GTACATCGGCCTCCGCCACTGGCTGCTGCTGTTCATCAGCGTGGTGTTGG
                 3060      3070      3080      3090      3100

130       140       150       160       170
905531        TGTGCACTTTCCTCGTCTGTGCTCTGCTGCTCCTNAACCCCTGGACGGCT
               *****  ********  **  ***  *   *  **  ******************
hpatched      CCTGCACATTCCTCGTGTGCGCTGTCTTCCTTCTGAACCCCTGGACGGCC
                 3110      3120      3130      3140      3150

180       190       200       210       220
905531        GGCCTNATAGTGCTGGTCCTGGCGATGATGACAGTGGAACTCTTTGGTAT
               **  ****  ***  ***********  *******  **  **  **  **  **  **
hpatched      GGGATCATTGTGATGGTCCTGGCGCTGATGACGGTCGAGCTGTTCGGCAT
                 3160      3170      3180      3190      3200

230       240       250
905531        CATGGGTTTNCTGGGCATCAAGCTGAGT
               *****  **  *  **  ********  ***
hpatched      GATGGGCCTCATCGGAATCAAGCTCAGT
                 3210      3220      3230
```

```
                      80        90       100       110       120
905531        TCTGGGCCTGCGGCGCTGCTTCCTGCTGGCCGTCTGCATCCTGCTGGTGT
               : : :    : : :       *  **  *  **  *****    ****   *  **  ****
hpatched      GCTGCTGCTGTTCATCAGCGTGGTGTTGGCC---TGCACATTCCTCGTGT
                 3090      3100      3110      3120

130       140       150
905531        GCACTTTCCTCGTCTGTGCTCTGCTGCT
               **  **  **  **  *         :        :
hpatched      GCGCTGTCTTCCTTCTGAACCCCTGGAC
                 3130      3140      3150
```

*FIG._2A*

SEQ ID NO: 5
```
                      30        40        50        60        70
1326258       GCTGGGGTGCACGCCTACCCCAGCGGCTCCCCCTTCCTCTTCTGGGAACA
              ::: ::   :   ****** ***** ****************** **
hpatched      CTGGGGCTGTCCAGTTACCCCAACGGCTACCCCTTCCTCTTCTGGGAGCA
                3010      3020      3030      3040      3050

80        90       100       110       120
1326258       GTATCTGGGCCTGCGGCGCTGCTTCCTGCTGGCCGTCTGCATCCTGCTGG
              ***  * ***** ** * ***  * ****** * ** ** *  ** ***
hpatched      GTACATCGGCCTCCGCCACTGGCTGCTGCTGTTCATCAGCGTGGTGTTGG
                3060      3070      3080      3090      3100

130       140       150
1326258       TGTGCACTTTCCTCNTCTGTGCTCT
              *****  ******** ** *** *
hpatched      CCTGCACATTCCTCGTGTGCGCTGT
                3110      3120      3130
```

```
                      90       100       110       120       130
1326258       TCTGGGCCTGCGGCGCTGCTTCCTGCTGGCCGTCTGCATCCTGCTGGTGT
              :::    :::      * **  * ** *****  ****   * ** ****
hpatched      GCTGCTGCTGTTCATCAGCGTGGTGTTGGCC---TGCACATTCCTCGTGT
                3090      3100      3110                3120

140       150
1326258       GCACTTTCCTCNTCTGTGCTCT
              ** ** ** ****           :
hpatched      GCGCTGTCTTCCTTCTGAACCC
                3130      3140
```

```
                              10        20        30        40        50
1326258       CCGGGCAGCATGCGCAGAGGCCGGCCAGGCTGGGGTGCACGCCTACCCCA
              ******  *****    ** ** * ***  ******  *             :
hpatched.RC   CCGGGCGGCATG--GCGAAGCGGACCACGCTGGGGGGTGGCTCAGGGGAG
SEQ ID NO: 6    710       720       730       740       750
```

FIG._2B (SEQ ID NO: 4) PTCH    1  MASAGNAAEPQDRGGGGSGCIGAPGRPAGGGRRRTGGLRRAAAPDRDYL
(SEQ ID NO: 2) PTCH2   1  ................................MTRSPPLREL-

PTCH    51  HRPSYCDAAFALEQISKGKATGRKAPLWLRAKFQRLLFKLGCYIQKNCGK
PTCH2   11  -PPSYTPP--ARTAAPQILAGSLKAPLWLRAYFQGLLFSLGCIQRHCGK

TM1
PTCH   101  FLVGLLFGAFAVGLKAANLETNVEELWVEVGGRVSRELNYTRQKIGEE
PTCH2   58  VLFGLLAFGALAFGAALGLRMAIIETNLEQLWVEVGSRVSQELHYIKEKLGEE

PTCH   151  AMFNPQLMIQTPKEEGANVLTTEALLQHLDSALQASRVHVYMYNRQWKLE
PTCH2  108  AAYTSQMLIQTARQEGENILTPEALGLHLQAALTASKVQVSLYGKSWDLN

PTCH   201  HLCYKSGELITETGYMDQIIEYLYPCLIITPLDCFWEGAKLQSGTAYLLG
PTCH2  158  KICYKSGVPLIENGMIEWMIEKLFPCVILTPLDCFWEGAKLQGGSAYLPG

PTCH   251  KPPLRWTNFFDPLEFLEELKKINYQVDSWEEMLNKAEVGHGYMDRPCLNPA
PTCH2  208  RPDIQWTNLDPEQLLEELLEELGPFA-SLEGFRELLDKAQVGQAYVGRPCLHPD

PTCH   301  DPDCPATAPNKNSTKPLDMALVLNGGCHGLSRKYMHWQEELIVGGTVKNS
PTCH2  257  DLHCPPSAPNHHSRQAPNVAHELSGGCHGFSHKFMHWQEELLLGGMARDP

```
PTCH   700  QSPESTSSTRDLLSQFSDSSLH--CLEPPCTKWTLSSFAEKHYAPFLLKP
PTCH2  634  ELFSPGGSTRDLLGQEEETRQKAACKSLPCARWNLAHFARYQFAPLLLQS
                          TM7
PTCH   748  KAKVVVLFLFLGLLGVSLYGTIRVRDGLDLTDIVPRETREYDFIAAQFKY
PTCH2  684  HAKAMVLVLFGALLGLSLVGAILVQDGLALTDVVPRGTKEHAFLSAQLRY

PTCH   798  FSFYNMYIVTQKA-DYPNIQHLLYDLHRSFSNVKYVMLEENKQLPKMWLH
PTCH2  734  FSLYEVALVTQGGFDYAHSQRALFDLHQRFSSLKAVLPPPATQAPRTWLH
                                       ***
PTCH   847  YFRDWLQGLQDAFDSDWETGKIMPNNYKNGSDDGVLAYKLLVQTGSRDKP
PTCH2  784  YYRNWLQGIQAAFDQDWASGRITRHSYRNGSEDGALAYKLLIQTGDAQEP

PTCH   897  IDISQLTKQRLVDADGIINPSAFYIYLTAWVSNDPVAYAASQANIRPHRP
PTCH2  834  LDFSQLTITRKLVDREGLIPPELFYMGLIVWVSSDPLGLAASQANFYPPP

PTCH   947  EWVHDKADYMPETRLRIPAAEPIEYAQFPFYLNGLRDTSDFVEAIEKVRT
PTCH2  884  EWLHDKYD-TTGENLRIPPAQPLEFAQFPFLLRGLLQKIADFVEAIEGARA
                                                         TM8
PTCH   997  ICSNYTSLGLSSYPNGYPFLFWEQYIGLRHWLLFISVVLACTFLVCAVF
PTCH2  933  ACAEAGQAGVHAYPSGSPFLFWEQYLGLRRCFLLAVCLLVGTFLVCALL
```

FIG._3C

```
                                     TM10
PTCH  1047 LLNPWTAGIIVMVLALMTVELFGMMGLIGIKLSAVPVVLIASVGIGVEF
PTCH2  983 LLNPWTAGLIVLVLAMMTVELFGIMGFLGIKLSAIPVVLLAGSEFD
                           TM11
PTCH  1097 TVHVALAFLTAIGDKNRRAVLALEHMFAPVLDGAVSTLLGVLMLAGSEFD
PTCH2 1033 TVHVALGFLTTQGSRNLRAAHALEHTFAPVTDGAISTLLGVLMLAGSHFD
                                  TM12
PTCH  1147 FIVRYFFAVLAILTILGVLNGLVLPVLLSFFGPYPEVSPANGLNRLPTP
PTCH2 1083 FIVRYFFAALTVLILGLLHGLVLLLSILGPPPEVIQMYKESPEILS

PTCH  1197 SPEPPPSVVRFAMPPGHTHSGSDSSDSEYSSQTTVSGLSEELRHYEAQQG
PTCH2 1133 PPAPQGGGLRWGASSSLPQS-FARVTTSMTVAIHPPPLPGAYIHPAPDEP

PTCH  1247 AGGPAHQVIVEATENPVFAHSTVVHPESRHHPPSNPRQQPHLDSGSLPPG
PTCH2 1182 PWSPAIATSSGNLSSRGPGPATG

PTCH  1297 RQGQQPRRDPPREGLWPPLYRPRRDAFEISTEGHSGPSNRARWGPRGARS

PTCH  1347 HNPRNPASTAMGSSVPGYCQPITTVTASASVTVAVHPPPVPGPGRNPRGG

PTCH  1397 LCPGYPETDHGLFEDPHVPFHVRCERRDSKVEVIELQDVECEERPRGSSS

PTCH  1447 N
```

FIG._3D

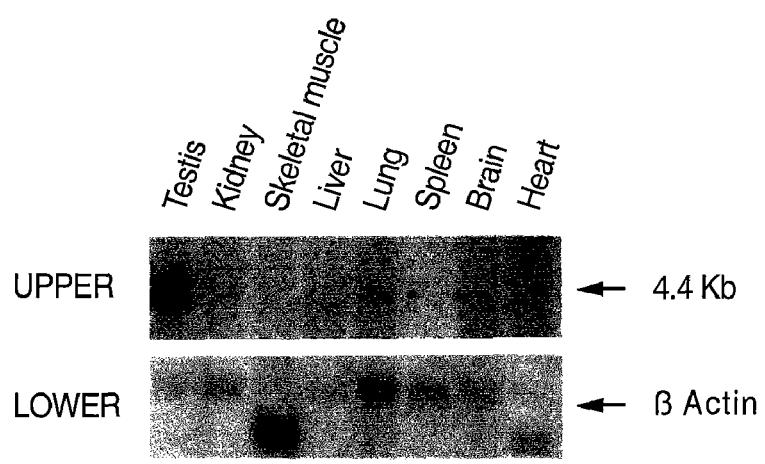
FIG._4
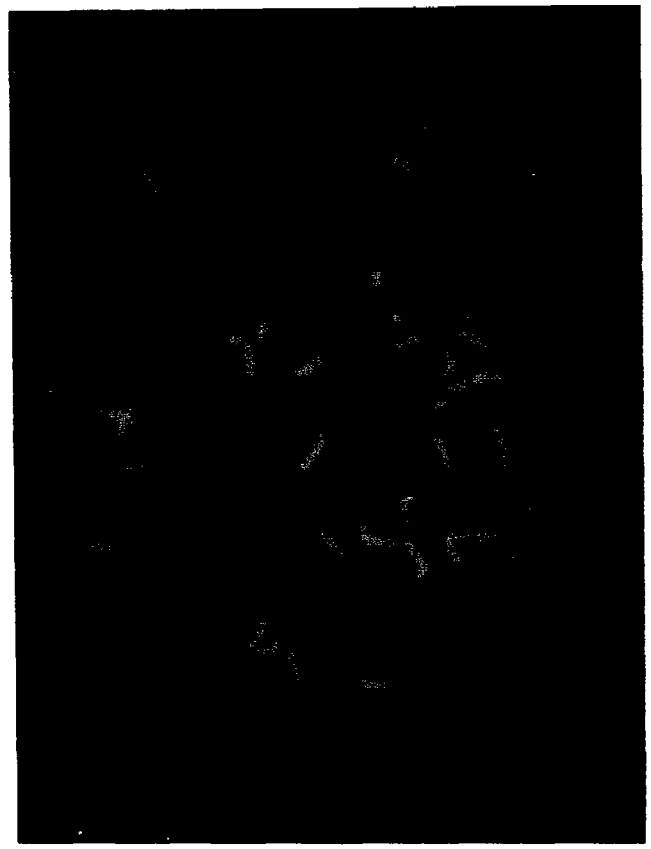
FIG._5

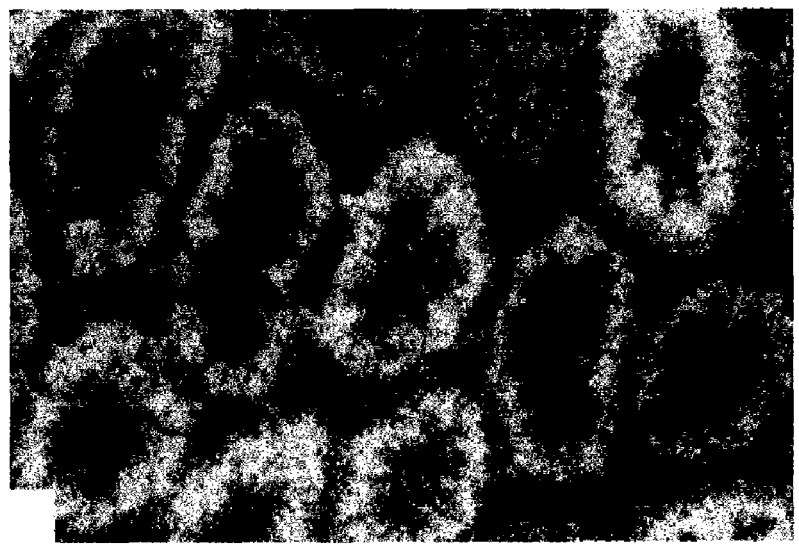
FIG._6C
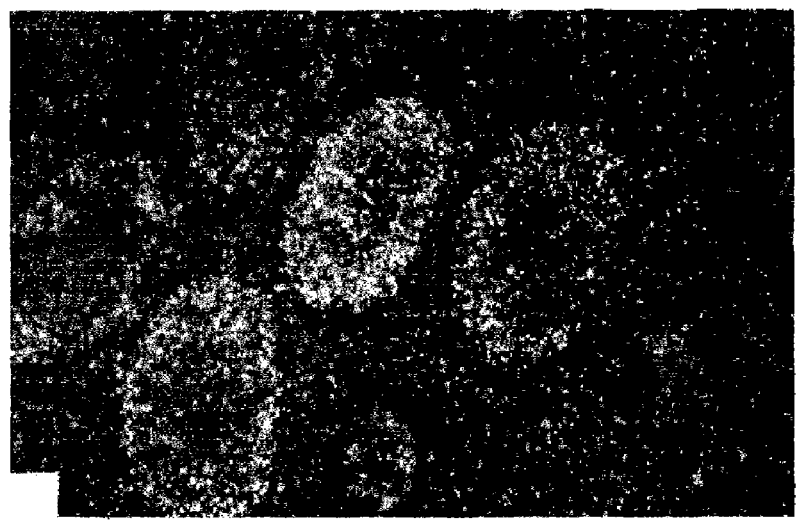
FIG._6B
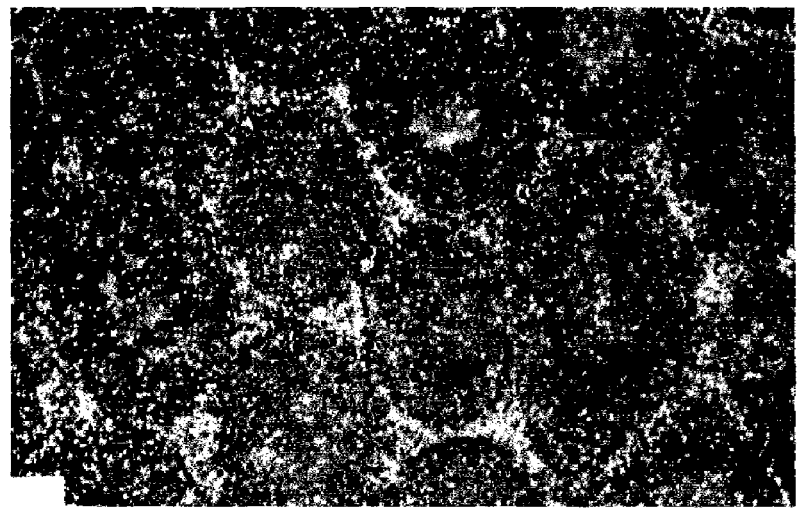
FIG._6A

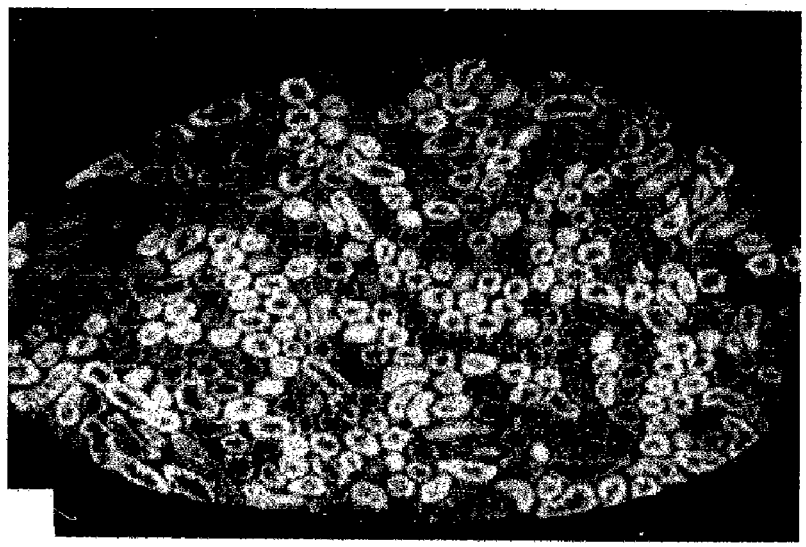
FIG._6F
FIG._6E
FIG._6D

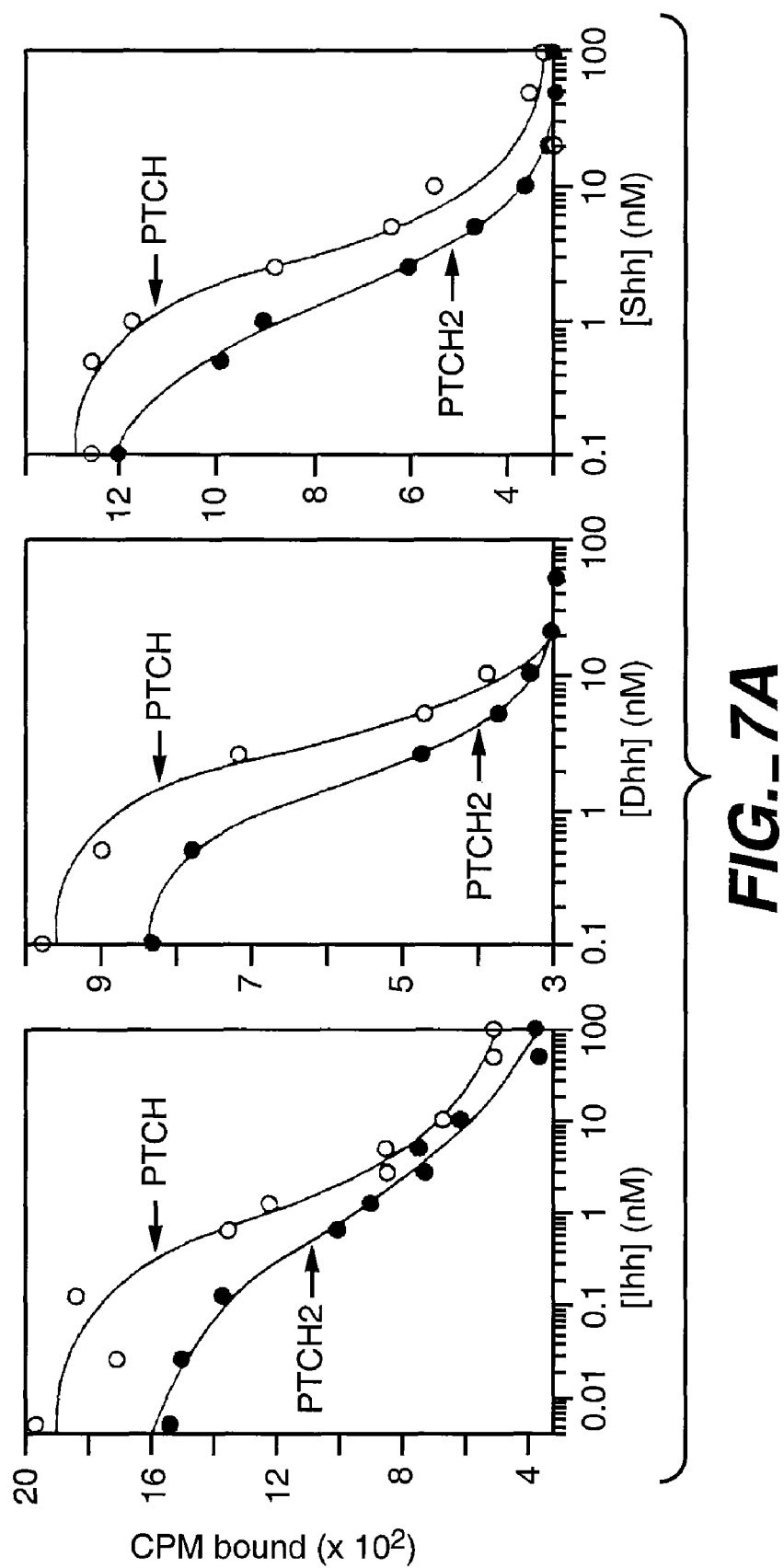
FIG._7A

|  | 10 | 20 | 30 | 40 | 50 |
|---|---|---|---|---|---| h*Ptch*-2     MTRSPPLRELPPSYTPPARTAAPQILAGSLKAPLWLRAYFQGLLFSLGCG
              * *. .* ********...****.*****************
mPatched2     MVRPLSLGELPPSYTPPARSSAPHILAGSLQAPLWLRAYFQGLLFSLGCR
(SEQ ID NO:7)  10        20        30        40        50

60        70        80        90       100
h*Ptch*-2     IQRHCGKVLFLGLLAFGALALGLRMAIIETNLEQLWVEVGSRVSQELHYT
              .******.*********.*.*.***************
mPatched2     IQKHCGKVLFLGLVAFGALALGLRVAVIETDLEQLWVEVGSRVSQELHYT
               60        70        80        90       100

110       120       130       140       150
h*Ptch*-2     KEKLGEEAAYTSQMLIQTARQEGENILTPEALGLHLQAALTASKVQVSLY
              ****************.* *.****.****************
mPatched2     KEKLGEEAAYTSQMLIQTAHQEGGNVLTPEALDLHLQAALTASKVQVSLY
               110       120       130       140       150

160       170       180       190       200
h*Ptch*-2     GKSWDLNKICYKSGVPLIENGMIEWMIEKLFPCVILTPLDCFWEGAKLQG
              **************************.******************
mPatched2     GKSWDLNKICYKSGVPLIENGMIERMIEKLFPCVILTPLDCFWEGAKLQG
               160       170       180       190       200

210       220       230       240       250
h*Ptch*-2     GSAYLPGRPDIQWTNLDPEQLLEELGPFASLEGFRELLDKAQVGQAYVGR
              **************.******************************
mPatched2     GSAYLPGRPDIQWTNLDPQQLLEELGPFASLEGFRELLDKAQVGQAYVGR
               210       220       230       240       250

260       270       280       290       300
h*Ptch*-2     PCLHPDDLHCPPSAPNHHSRQAPNVAHELSGGCHGFSHKFMHWQEELLLG
              *.* *****.****.***********************
mPatched2     PCLDPDDPHCPPSAPNRHSRQAPNVAQELSGGCHGFSHKFMHWQEELLLG
               260       270       280       290       300

310       320       330       340       350
h*Ptch*-2     GMARDPQGELLRAEALQSTFLLMSPRQLYEHFRGDYQTHDIGWSEEQAST
              * * .*****************************************
mPatched2     GTARDLQGQLLRAEALQSTFLLMSPRQLYEHFRGDYQTHDIGWSEEQASM
               310       320       330       340       350

*FIG._8A*

```
              360        370        390        390        400
hPtch-2   VLQAWQRRFVQLAQEALPENASQQIHAFSSTTLDDILHAFSEVSAARVVG
          ******************* ****************** ****** .****
mPatched2 VLQAWQRRFVQLAQEALPANASQQIHAFSSTTLDDILRAFSEVSTTRVVG
              360        370        380        390        400

410        420        430        440        450
hPtch-2   GYLLMLAYACVTMLRWDCAQSQGSVGLAGVLLVALAVASGLGLCALLGIT
          *****************************.*******************
mPatched2 GYLLMLAYACVTMLRWDCAQSQGAVGLAGVLLVALAVASGLGLCALLGIT
              410        420        430        440        450

460        470        480        490        500
hPtch-2   FNAATTQVLPFLALGIGVDDVFLLAHAFTEALPGTPLQERMGECLQRTGT
          ******************.******* * *.*** ****** . ***
mPatched2 FNAATTQVLPFLALGIGVDDIFLLAHAFTKAPPDTPLPERMGECLRSTGT
              460        470        480        490        500

510        520        530        540        550
hPtch-2   SVVLTSINNMAAFLMAALVPIPALRAFSLQAAIVVGCTFVAVMLVFPAIL
          ** ***.*** **.******************* * *********
mPatched2 SVALTSVNNMVAFFMAALVPIPALRAFSLQAAIVVGCNFAAVMLVFPAIL
              510        520        530        540        550

560        570        580        590        600
hPtch-2   SLDLRRRHCQRLDVLCCFSSPCSAQVIQILPQELGDGTVPVGIAHLTATV
          ******* ******************.****** .***********
mPatched2 SLDLRRRHRQRLDVLCCFSSPCSAQVIQMLPQELGDRAVPVGIAHLTATV
              560        570        580        590        600

610        620        630        640        650
hPtch-2   QAFTHCEASSQHVVTILPPQAHLVPPPSDPLGSELFSPGGSTRDLLGQEE
          ********************..*.*******.***********.***
mPatched2 QAFTHCEASSQHVVTILPPQAHLLSPASDPLGSELYSPGGSTRDLLSQEE
              610        620        630        640        650

660        670        680        690        700
hPtch-2   ETRQKAACKSLPCARWNLAHFARYQFAPLLLQSHAKAIVLVLFGALLGLS
          *  ***..* **.* ***************..*** **..*******
mPatched2 GTGPQAACRPLLCAHWTLAHFARYQFAPLLLQTRAKALVLLFFGALLGLS
              660        670        680        690        700
```

FIG._8B

|  | 710 | 720 | 730 | 740 | 750 | hPtch-2    LYGATLVQDGLALTDVVPRGTKEHAFLSAQLRYFSLYEVALVTQGGFDYA
           *************************************************
mPatched2  LYGATLVQDGLALTDVVPRGTKEHAFLSAQLRYFSLYEVALVTQGGFDYA
              710       720       730       740       750

760       770       780       790       800
hPtch-2    HSQRALFDLHQRFSSLKAVLPPPATQAPRTWLHYYRNWLQGIQAAFDQDW
           ****************************************.**********
mPatched2  HSQRALFDLHQRFSSLKAVLPPPATQAPRTWLHYYRSWLQGIQAAFDQDW
              760       770       780       790       800

810       820       830       840       850
hPtch-2    ASGRITRHSYRNGSEDGALAYKLLIQTGDAQEPLDFSQLTTRKLVDREGL
           **** *******************.************.*
mPatched2  ASGRITCHSYRNGSEDGALAYKLLIQTGNAQEPLDFSQLTTRKLVDKEGL
              810       820       830       840       850

860       870       880       890       900
hPtch-2    IPPELFYMGLTVWVSSDPLGLAASQANFYPPPPEWLHDKYDTTGENLRIP
           *************************************************
mPatched2  IPPELFYMGLTVWVSSDPLGLAASQANFYPPPPEWLHDKYDTTGENLRIP
              860       870       880       890       900

910       920       930       940       950
hPtch-2    PAQPLEFAQFPFLLRGLQKTADFVEAIEGARAACAEAGQAGVHAYPSGSP
           .*********.***************.**************
mPatched2  AAQPLEFAQFPFLLHGLQKTADFVEAIEGARAACTEAGQAGVHAYPSGSP
              910       920       930       940       950

960       970       980       990       1000
hPtch-2    FLFWEQYLGLRRCFLLAVCILLVCTFLVCALLLLNPWTAGLIVLVLAMMT
           *****************************.**************
mPatched2  FLFWEQYLGLRRCFLLAVCILLVCTFLVCALLLLSPWTAGLIVLVLAMMT
              960       970       980       990       1000

1010      1020      1030      1040      1050
hPtch-2    VELFGIMGFLGIKLSAIPVVILVASVGIGVEFTVHVALGFLTTQGSRNLR
           *******************.************..****
mPatched2  VELFGIMGFLGIKLSAIPVVILVASIGIGVEFTVHVALGFLTSHGSRNLR
              1010      1020      1030      1040      1050

*FIG._8C*

```
                    1060       1070       1080       1090       1100
hPtch-2    AAHALEHTFAPVTDGAISTLLGLLMLAGSHFDFIVRYFFAALTVLTLLGL
           ** ***.********.************.****.****  ********
mPatched2  AASALEQTFAPVTDGAVSTLLGLLMLAGSNFDFIIRYFFVVLTVLTLLGL
                    1060       1070       1080       1090       1100

1110       1120       1130       1140       1150
hPtch-2    LHGLVLLPVLLSILGPPPEVIQMYKESPEILSPPAPQGGGLRWGASSSLP
           ****.*************.*.*.*****. *...*** *****. ...**
mPatched2  LHGLLLLPVLLSILGPPPQVVQVYKESPQTLNSAAPQRGGLRWDRPPTLP
                    1110       1120       1130       1140       1150

1160       1170       1180       1190       1200
hPtch-2    QSFARVTTSMTVAIHPPPLPGAYIHPAPDEPPWSPAATSSGNLSSRGPGP
           ************.*********.***..**
mPatched2  QSFARVTTSMTVALHPPPLPGAYVHPASEEPT
                    1160       1170       1180 hPtch-2    ATG
```

FIG._8D

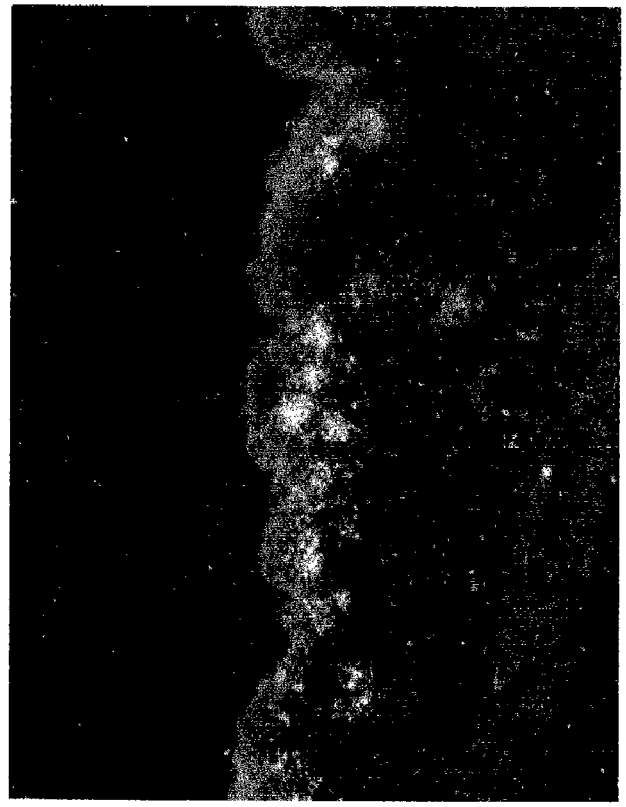
FIG._9

> Consensus Sequence of human patched 2 cDNA clone
> length: 4004 bp
SEQ ID NO: 8

```
  1 CCCACGCGTC CGGAGAGAAGC TGGGGAGGA GGCTGCATAC ACCTCTCAGA TGCTGATACA GACCGCACGC CAGGAGGGAG AGAACATCCT CACACCCGAA
    GGGTGCGCAG GCCCTCTTCG ACCCCCTCCT CCGACGTATG TGGAGAGTCT ACGACTATGT CTGGCGTGCG GTCCTCCCCTC TCTTGTAGGA GTGTGGGCTT
                                                         ^                                                    ^
                                                       race 6                                              race 5'
101 GCACTTGGCC TCCACCTCCA GGCAGCCCTC ACTGCCAGTA AGTCCAAGT ATCACTCTAT GGGAAGTCCT GGGATTTGAA CAAAATCTGC TACAAGTCAG
    CGTGAACCGG AGGTGGAGGT CCGTCGGGGA TGACGGTCAT TTCAGTTCA TAGTGAGATA CCCTTCAGGA CCCTAAACTT GTTTTAGACG ATGTTCAGTC
201 GAGTTCCCCT TATTGAAAAT GGAATGATTG AGCGGATGAT TGAGAAGCTG TTTCCGTGCG TGATCCTTAC CCCCCCTCGAC TGCTTCTGGG AGGGAGCCAA
    CTCAAGGGGA ATAACTTTTA CCTTACTAAC TCGCCTACTA ACTCTTCGAC AAAGGCACGC ACTAGGAGTG GGGGAGCTG ACGAAGACCC TCCCTCGGTT
301 ACTCCAAGGG GGCTCCGCCT ACCTGCCGCT CCCAATGTGG CTCACGAGCT GAGTGGGGGC CTCACCCCCG ACGGTACCGA AGAGGTGTT TAAGTACGTG
    TGAGGTTCCC CCGAGGCGGA TGGACGGCGA GGGTTACACC GAGTGCTCGA CTCACCCCCG TGCCATGGCT CTGGGG GTGTGGTCT TAAGTACGTG ACCGTCCTCC
401 AATTGCTGCT GGGAGGCATG GCCAGAGACC CCCAAGGAGA GCTGCTGAGG GCAGAGGCCC CTTCTTGCTG ATGAGTCCCC GCCAGCTGTA
    TTAACGACGA CCCTCCGTAC CGGTCTCTGG GGGTTCCTCT CGACGACTCC CGTCTCCGGG ACGTCTCGTG GAAGAACGAC TACTCAGGGG CGGTCGACAT
501 CGAGCATTTC CGGGGTGACT ATCAGACACA TGACATTGGC TGGAGTGAGG AGCAGGCCAG ACCTCACTCC CCCTCCTGCC CTTCAGCTGG CAAGCCTGGC TGTGCAGGTC
    GCTCGTAAAG GCCCCACTGA TAGTCTGTGT ACTGTAACCG ACCTCACTCC TGGTCCGGTC GTCGTCCGAT CGGTCGGCCA GTTCGGACCG ACACGTCCAG
601 GGTATGGACA AGGACAGGGG GGTGCCCTGA GGCCATTCCC TCCTCCTGCC GGCCATTCCC CCCTCCTATC CACCCTGTTT CTCCAGCTGG CCCAGGAGGC CCTGCCTGAG
    CCATACCTGT TCCTGTCCCC CCACGGGACT CCGGTAAGGG AGGAGGACGG GGGAGGATAG GTGGGACAAA GAGGTCGACC GGGTCCTCCG GGACGACTC
```

FIG.—10A

```
 701  AACGCTTCCC AGCAGATCCA TGCCTTCTCC TCCACCACCC TGGATGACAT CCTGCATGCG TTCTCTGAAG TCAGTGCTGC CCGTGTGGTG GGAGGCTATC
      TTGCGAAGGG TCGTCTAGGT ACGGAAGAGG AGGTGGTGGG ACCTACTGTA GGACGTACGC AAGAGACTTC AGTCACGACG GGCACCACCA CCTCCGATAG

801  TGCTCATGGT GGGTCTTGCA CCTGGCACCT TGCCCCCACC CCAGTGCCCA CCACCTCCAA CCCCTGGGAG CCCCTGAGAC TGCCCTTTCC CCCCACAGCT
      ACGAGTACCA CCCAGAACGT GGACCGTGGA ACGGGGGTGG GGTCACGGGT GGTGGAGGTT GGGGACCCCT GGGGACTCTG ACGGGAAAGG GGGGTGTCGA

901  GGCCTATGCC TGTGTGACCA TGCTGCCGCC CAGTCCCAGG GTTCCGTGGG CCTTGCCGGG GTACTGCTGG GGTGGCCTCA
      CCGGATACGG ACACACTGGT ACGACGGCGG GTCAGGGTCC CAAGGCACCC CGAACGGCCC CATGACGACC CCACCGGAGT

1001  GGCCTTGGGC TCTGTGCCCT GCTCGGCATC ACCTTCAATG CTGCCACTAC CCAGTACGC CAGGACTGCA GGGCAGAGACT ACCAGGCTTC
      CCGAACCCG AGACACGGGA CGAGCCGTAG TGGAAGTTAC GACGGTGATG GTCCTGACGT CCGTCTGAG TCACGGTCAG TGGTCCGAAG

1101  ACGGGTCCTC AGCTGCCCGC TCCTCTGCCC TGCCCTTCTT GACTCTGGGA ATCGGCTGG ATGACGTATT CCTGCTGGGG CATGCCTTCA
      TGCCCAGGAG TCGACGGGCG AGGAGACGGG ACGGGAAGAA CTGAGACCCT TAGCCGCACC TACTGCATAA GGACGACCGC GTACGGAAGT

1201  CAGAGGCTCT GCCTGGCACC CCTCTCCAGG TGGGGCCTTG TCCCCCAGGG CTCATCTGAG GCAGCTCAGC TTACTGGTTA AGAGCCTCTT GGTTCAAGTG
      GTCTCCGAGA CGGACCGTGG GGAGAGGTCC ACCCCGGAAC AGGGGGTCCC GAGTAGACTC CGTCGAGTCG AATGACCAAT TCTCGGAGAA CCAAGTTCAC

1301  ACCTTGGGCT GCTAATGAAC CTTGTGTGCCT CTTGTCCCCA TGTGTCCCCA GAACAGGGGT ACACATTTGT CCCTAAGGGT TATTGTTTGG ATCAGTGAAG
      TGGAACCCGA CGATTACTTG GAACACACGGA GAACAGGGGT CTTGTCCCCA GAATTCCCA ATCACGACAC AGGATTCCCA ATAACAAACC TAGTCACTTC

1401  TAACTCAAGT TGAATGCTTA GAACAGCCCA ATGGTACCCA ATAAATGCTA GCCACTGTGT TATGACTGCC CCACCTCTGC ACCCCAAGTT
      ATTGAGTTCA ACTTACGAAT CTTGTCGGGT TACCATGGGT TATTTACGAT CGGTGACACA ATACTGACGG GGTGGAGACG TGGGGTTCAA
```

FIG._10B

```
1501  CCTGAGCCTC CCCTTCACTC CACTTTGACA CGGCCCCTCC CTTGTGACCT GAGGGCAGGT CCCCACTCTG TCCTGGCAGG AGCGCATGGG CGAGTGTCTG
      GGACTCGGAG GGGAAGTGAG GTGAAACTGT GCCGGGGAGG CAACACTGGA CTCCCGTCCA GGGGTGAGAC AGGACCGTCC TCGCGTACCC GCTCACAGAC

1601  CAGGCGCACGG GCACCAGTGT TGTACTCACA TCCATCAACA ACATGGCCGC CTTCCTCATG GCTGCCCTCG TTCCCATCCC TGGCTGCGA GCCTTCTCCC
      GTCGCGTGCC CGTGGTCACA ACATGAGTGT AGGTAGTTGT TGTACCGGCG GAAGGAGTAC CGACGGGAGC AAGGGTAGGG ACGGCGACGCT CGGAAGAGGG

1701  TACAGCCTGG ACCTACGGCG GCGCCACTGC CAGCGCCTTG ATGTGCTCTG CTGCTTCTCC AGGTACTGCC CCCCTTCCTC CCGTGACCCA
      ATGTCGGACC TGGATGCCGC CGCGGTGACG GTCGCGGAAC TACACGAGAC GACGAAGAGG TCCATGACGG GGGGAAGGAG GGCACTGGGT

1801  CGGCCAGCCTG TCCCCCTCACC AGCATTTCAA GGCACAGACC TGTCATCCAC TCTCTACCTC TTCCAGTCCC TGCTCTGCTC AGTGATTCA GATCCTGCCC
      GCGGTCGGAC AGGGGAGTGG TCGTAAAGTT CCGTGTCTGG ACAGTAGGTG AAGGTCAGGG ACGAGACGAG AAGGTCAGGG TCCACTAAGT CTAGGACGGG

1901  CAGGAGCTGG GGGACGGGAC AGTACCAGTG GGCATTGCCC ACCTCACTGC CACAGTTCAA GCCTTTACCC ACTGTGAAGC CAGCAGCCAG CATGTGGTCA
      GTCCTCGACC CCCTGCCCTG TCATGGTCAC CCGTAACGGG TGGAGTGACG GTGTCAAGTT CGGAAATGGG TGACACTTCG GTCGTCGGTC GTACACCAGT

2001  CCATCCTGCC TCCCCAAGCC CACCTGGTTC TGACCCACTG GGCTCTGAGC TCTTCAGCCC TGGAGGGTCC ACACGGGACC TTCTAGGCCA
      GGTAGGACGG AGGGGTTCGG GTGGACCACG ACTGGGTGAC CCGAGACTCG AGAAGTCGGG ACCTCCCAGG TGTGCCCTGG AAGATCCGGT

2101  GGAGGAGGAG ACAAGGCAGA AGGCAGCCTG CAAGTCCCTG CCCTGTGCCC GCTGAATCT TGCCCATTTC GCCCGCTATC AGTTTGCCCC GTTGCTGCTC
      CCTCCTCCTC TGTTCCGTCT TCCGTCGGAC GTTCAGGGAC GGGACACGGG CGACCTTAGA ACGGGTAAAG CGGGCGATAG TCAAACGGGG CAACGACGAG

2201  CAGTCACATG CCAAGGCCAT CGTGCTGGTG CTCTTTGGTG CCTGAGCCTC TACGGAGCCA CCTTGGTGCA AGACGGGCCTG GCCCTGACGG
      GTCAGTGTAC GGTTCCGGTA GCACGACCAC GAGAAACCAC GAGAAGACCC GGACTCGGAG ATGCCTCGGT GGAACCACGT TCTGCCCGGAC CGGGACTGCC
```

*FIG._10C*

```
2301  ATGTGGTGCC TCGGGGCACC AAGGAGCATG CCTTCCTGAG CGCCCAGCTC AGTACTTCT CCCTGTACGA GGTGGCCCAG GTGACCCAGG GTGGCTTTGA
      TACACCACGG AGCCCCGTGG TTCCTCGTAC GGAAGGACTC GCGGGTCGAG TCCATGAAGA GGGACATGCT CCACCGGGTC CACCGGGTCC CACCGAAACT

2401  CTACGCCCAC TCCCAACGCG CCCTCTTTGA TCTGCACCAG CGCTTCAGTT CCCTCAAGGC GGTGCTGCCC CCACCGGCCA CCCAGGCACC CCGCACCTGG
      GATGCGGGTG AGGGTTGCGC GGGAGAAACT AGACGTGGTC GCGAAGTCAA GGGAGTTCCG CCACGACGGG GGTGGCCGGT GGGTCCGTGG GGCGTGGACC

2501  CTGCACTATT ACCGCAACTG GCTACAGGGA ATCCAGGCTG CCTTTGACCA GGACTGGGCT TCACCCGCCA TCGTACCGC CTCGTACCGC AATGGCTCTG
      GACGTGATAA TGGCGTTGAC CGATGTCCCT TAGGTCCGAC GGAAACTGGT CCTGACCCGA AGTGGGCGCG AGTGGGCGGT GAGCATGGCG TTACCGAGAC

2601  AGGATGGGGC CCTGGCCTAC AAGCTGCTCA TCCAGACTGG AGACGCCCAG GAGCCTCTGG ATTTCAGCCA GGTTGGGAGA GGGCTGGAGG GGTCCACTAG
      TCCTACCCCG GGACCGGATG TTCGACGAGT AGGTCTGACC TCTGCGGGTC CTCGGGAGAC TAAAGTCGGT CCAACCCTCT CCCGACCTCC CCAGTGATC

2701  TACAGGGGCT GCAGGCCTCC CCTTCAGCCC TGGGCCCAGG GTGAGCAGTG ACCCCCTGGG TCTGGCAGCC TCACAGGCCA ACTTCTACCC CCCACCTCCT GAATGGCTGC
      ATGTCCCCGA CGTCCGGAGG GGAAGTCGGG ACCCGGGTCC CACTCGTCAC TGGGGGACCC AGACCGTCGG AGTGTCCGGT TGAAGATGGG CTTACGACG

2801  GAGCTCTTCT ACATGGGGCT GACCGTGTGG GTGAGCAGTG ACCCCCTGGG TCTGGCAGCC TCACAGGCCA ACTTCTACCC CCACCTCCT GAATGGCTGC
      CTCGAGAAGA TGTACCCCGA CTGGCACACC CACTCGTCAC TGGGGGACCC AGACCGTCGG AGTGTCCGGT TGAAGATGGG CTTACGACG

2901  ACGACAAATA CGACACCACG GGGGAGAACC TTCGCAGTGA GTCTTGGGGG GAGCTCGGCA AGAGCCTCAG CCTCGCCCAC ACAAGCCCTG AGCCTGAGGC
      TGCTGTTTAT GCTGTGGTGC CCCCTCTTGG AAGCGTCACT CAGAACCCCC CTCGAGCCGT TCTCGGAGTC GGAGCGGGTG TGTTCGGGAC TCGGACTCCG

3001  CCTGCCCACT CTGCCCCGTG CTCACCGCCC TGTCCCTCTC CCTCCACAGT CCCGCCCAGCT CAGCCCTTGG AGTTTGCCCA
      GGACGGGTGA GACGGGGCAC GAGTGGCGGG ACAGGGAGAG GGAGGTGTCA GGAGGTGTCA GTCGGGAACC TCAAACGGGT
```

*FIG._10D*

```
3101 GTTCCCCTTC CTGCTGCGTG GCCTCCAGAA GACTGCAGAC TTTGTGGAGG CCATCGAGGG GGCCCGGGCA GCATGCGCAG AGGCCGGCCA GGCTGGGGTG
     CAAGGGGAAG GACGACGCAC CGGAGTCTT CTGACGTCTG AAACACCTCC GGTAGCTCCC CCGGGCCCGT CGTACGCGTC TCCGGCCGGT CCGACCCCAC

3201 CACGCCTACC CCAGCGGCTC CCCCTTCCTC TTCTGGGAAC AGTATCTGGG CCTGCGGCGC TGCTTCCTGC TGGCCGTCTG CATCCTGCTG GTGTGCACTT
     GTGCGGATGG GGTCGCCGAG GGGAAGGAG AAGACCCTTG TCATAGACCC GGACGCCGCG ACGAAGGACG ACCGGCAGAC GTAGGACGAC CACACGTGAA

3301 TCCTCGTCTG TGCTCTGCTG CTCCTCAACC CCTGGACGGC TGGCCTCATA GTGAGTGCTT GCAGGAGTGG GGACAGAGAC ACCCCACCCT TCCCTGCCCA
     AGGACGAGAC ACGAGACGAC GAGGAGTTGG GGACCTGCCG ACCGGAGTAT CACTCACGAA CGTCCTCACC CCTGTCTCTG TGGGGTGGGA AGGGACGGGT

3401 GCCTGTCATC CCTCCTGCCA GGAGCCCTCT GTGAGCCCTG TCTCCCTCAG GTGCTGGTCC TGGCGATGAT GACAGTGGAA CTCTTTGGTA TCATGGGTTT
     CGGACAGTAG GGAGGACGGT CCTCGGGAGA CACTCGGGAC AGAGGGAGTC CACGACCAGG ACCGCTACTA CTGTCACCTT GAGAAACCAT AGTACCCAAA

3501 CCTGGGCATC AAGCTGAGTG GGTGATCCTT GTGGCCTCTG TAGGCATTGG CGTTGAGTTC ACAGTCCACG TGGCTCTGGT GAGCACGGGC
     GGACCCGTAG TTCGACTCAC CCACTAGGAA CACCGGAGAC ATCCGTAACC GCAACTCAAG TGTCAGGTGC ACCGAGACCA CTCGTGCCCG

3601 ACCCCGGGGA GGGACCAATC AGCTGATTCA GTATTCAACA CATATTGTTC AAGCCCCTAC TATGTGCTAG AGAATTTGGG CTGGGTGGAC
     TGGGGCCCCT CCCTGGTTAG TCGACTAAGT CATAAGTTGT GTATAACAAG TTCGGGGATG ATACACGATC TCTTAAACCC GACCCACCTG

3701 GTGGTGGCTC ATTCCTGTAA TCCCAGCACT TTGGGAGGCC GAGGCGGGTG GATCACCTGA GGTCGGGAGT CCAGCCCTCA AGCTTTGGTC CCTGCCAAC ATGGTGAAAC
     CACCACCGAG TAAGGACATT AGGGTCGTGA AACCCTCCGG CTCCGCCCAC CTAGTGGACT CCAGCCCTCA GGTCGGGAGT TCGAAACCAG GGACCGGTTG TACCACTTTG

3801 CCTGTCTTTA CTAAAAATAC AAAAAATTAG CCAGGCGTGG TGGCACATGC CAGTAGTCCC AGCTACTTTG GAGGCTGAGG CAGAATTGCT TGAACCTGGG
     GGACAGAAAT GATTTTTATG TTTTTTAATC GGTCCGCACC ACCGTGTACG GTCATCAGGG TCGATGAAAC CTCCGACTCC GTCTTAACGA ACTTGGACCC

3901 AGGCGAAGGT TGCAGTGAGC TGAGATCGTG CCATTGCACT CCAGCCTGGG CAACAAGAGT GCAACTCTCC GTCTCAAAAA AAAAAAAAAA AAGGGCGGCC
     TCCGCTTCCA ACGTCACTCG ACTCTAGCAC GGTAACGTGA GGTCGGACCC GTTGTTCTCA CGTTGAGAGG CAGAGTTTTT TTTTTTTTTT TTCCCGCCGG

4001 GCGA
     CGCT
```

*FIG._10E*

Clone 16.1 human patched 2
> length: 2082 bp
> SEQ ID NO: 9

```
  1 TTCCGGCATG ACTCGATCGC CGCCCCTCAG AGAGCTGCCC CCGAGTTACA CACCCCCAGA GCACCCCAGA TCCTAGCTGG GAGCCTGAAG
    AAGGCCGTAC TGAGCTAGCG GCGGGGAGTC TCTCGACGGG GGCTCAATGT GTGGGGTCG AGCTTGGCGT CGTGGGTCT AGGATCGACC CTCGGACTTC
101 GCTCCACTCT GGCTTCGTGC TTACTTCCAG GCCCTGCTCT TCTCTCTGGG ATGCGGGATC CAGAGACATT GTGGCAAAGT GCTCTTTCTG GGACTGTTGG
    CGAGGTGAGA CCGAAGCACG AATGAAGGTC CGGACGACT AGAGAGACCC TACGCCCTAG GTCTCTGTAA CACCGTTTCA CGAGAAAGAC CCTGACAACC
201 CCTTTGGGGC CCTGGCATTA GGTCTCCCGCA TGGCCATTAT TGAGACAAAC TTGGAACAGC TCTGGGTAGA AGTGGGCAGC CGGGTGAGCC AGGAGCTGCA
    GGAAACCCCG GGACCGTAAT CCAGAGGCGT ACCGGTAATA ACTCTGTTTG AACCTTGTCG AGACCCATCT TCACCCGTCG GCCCACTCGG TCCTCGACGT
301 TTACACCAAG GAGAAGCTGG GGGAGGAGGC TGCATACACC TCTCAGATGC TGATACAGAC ACTCTATGTG CGCACGCCAG GAGGAGAGA ACATCCTCAC ACCCGAAGCA
    AATGTGGTTC CTCTTCGACC CCCTCCTCCG ACGTATGTGG AGAGTCTCTG ACTATATCTG TGAGATACCC GCGTGCGGTC CTCCCTCTCT TGTAGGAGTG TGGGCTTCGT
401 CTTGGCCTCC ACCTCCAGGC AGCCCTCACT GCCAGTAAAG TCCAAGTATC ACTCTATGGG AAGTCCTGGG ATTTGAACAA AATCTGCTAC AAGTCAGGAG
    GAACCGGAGG TGGAGGTCCG TCGGGAGTGA CGGTCATTTC AGGTTCATAG TGAGATACCC TTCAGGACCC TAAACTTGTT TTAGACGATG TTCAGTCCTC
501 TTCCCCTTAT TGAAAATGGA ATGATTGAGT GGATGATTGA GAAGCTGTTT CCGTGCGTGA TCCTCACCCC CCTCGACTGC TTCTGGGAGG GAGCCAAACT
    AAGGGGAATA ACTTTTACCT TACTAACTCA CCTACTAACT CTTCGACAAA GGCACGCACT AGGAGTGGGG GGAGCTGACG AAGACCCTCC CTCGGTTTGA
```

FIG._11A

```
 601 CCAAGGGGGC TCCGCCTACC TGCCCGGCCG CCCGGATATC CAGTGGACCA ACCTGGATCC AGAGCAGCTG CTGGAGGAGC TGGTCCCTT TGCCTCCCTT
     GGTTCCCCCG AGGGCGGATGG ACGGGCCGGC GGGCCTATAG GTCACCTGGT TGGACCTAGG TCTCGTCGAC GACCTCCTCG ACCCAGGGAA ACGGAGGGAA

701 GAGGGCTTCC GGGAGTGCT AGACAAGGCA CAGTGGGCC AGGCCTACGT GGGGCGGCCC TGTCTGCACC CTGATGACCT CCACTGCCCA CCTAGTGCCC
     CTCCCGAAGG CCCTCGACGA TCTGTTCCGT GTCACCCGG CCCGCCGGG ACAGACGTGG GACTACTGGA GGTGACGGGT GGATCACGGG

801 CCAACCATCA CAGCAGGCAG GCTCCCAATG GCTGAGTGGG TGGCTCACGA GCTTCTCCCA CAAATTCATG CACTGGCAGG AGGAATTGCT
     GGTTGGTAGT GTCGTCCGTC CGAGGGTTAC CGACTCACCC ACCGAGTGCT CGAAGAGGGT GTTTAAGTAC GTGACCGTCC TCCTTAACGA

901 GCTGGAGGC ATGGCCAGAG ACCCCCAAGG AGAGCTGCTG CCCTGCAGAG AGGAGCAGGC CTACAAGCCT CACCTTCTTG CCCGCCAGCT GTACGAGCAT
     CGACCCTCCG TACCGGTCTC TGGGGGTTCC TCTCGACGAC TCCCGTCTCC TCCTCGTCCG GGGACGTCTC GTGGAAGAAC GGGCGGTGA CATGCTCGTA

1001 TTCCGGGGTG ACTATCAGAC ACATGACATT GGCTGGAGTG CAGGAGCAGGC CTACAAGCCT CTACAAGCCT CTTTGTGCAG CTGGCCCAGG
     AAGGCCCCAC TGATAGTCTG TGTACTGTAA CCGACCTCAC GTCGTGTCAC GATGTTCGGA CCGTCGCCGC GAAACACGTC GACCGGGTCC

1101 AGGCCCTGCC TGAGAACGCT TCCCAGCAGA TCCATGCCTT CTCCTCCACC ACCCTGGATA ACATCCTGCA TCCGTTCTCT GAAGTCAGTG CTGCCCGTGT
     TCGGGGACGG ACTCTTGCGA AGGGTCGTCT AGGTACGGAA GAGGAGGTGG TGGGACCTAT TGTAGGACGT AGGCAAGAGA CTTCAGTCAC GACGGGCACA

1201 GGTGGGAGGC TATCTGCTCA TGCCTGTGTG ACCATGCTGC GGTGGACTG CCCCCAGTCC CGCCCAGTCC CAGGGTTCCG TGGGCCTTGC CGGGGTACTG
     CCACCCTCCG ATAGACGAGT ACGACCGGAT TGGTACGACG CCACCTGAC GTCCCAAGGC GTCCCAAGGC GTCCCAAGGC ACCCGGAACC GCCCCATGAC

1301 CTGGTGGCCC TGGCGGGTGG CTCAGGCCTT GGGCTCTGTG CCCTGCTCGG CATCACCTTC AATGCTGCCA CTACCCAGGT GCTGCCCTTC TTGGCTCTGG
     GACCACCGGG ACCGCCACCG GAGTCCGGAA CCCGAGACAC GGGACGAGCC GTAGTGGAAG TTACGACGGT GATGGGTCCA CGACGGGAAG AACCGAGACC
```

FIG._11B

```
1401 GAATCGGCGT GGATGACGTA TTCCTGCTGG CGCATGCCTT CACAGAGGCT CTGCCTGGCA CCCCTCTCCA GGAGCGCATG GGCGAGTGTC TGCAGCGCAC
     CTTAGCCGCA CCTACTGCAT AAGGACGACC GCGTACGGAA GTGTCTCCGA GACGGACCGT GGGGAGAGGT CCTCGCGTAC CCGCTCACAG ACGTCGCGTG

1501 GGGCACCAGT GTCGTACTCA CATCCATCAA CAACATGGCC GCCTTCCTCA TGGCTGCCCT CGTTCCCATC CCTGCCGCTGC GAGCCTTCTC CTTACAGCCA
     CCCGTGGTCA CAGCATGAGT GTAGGTAGTT GTTGTACCGG CGGAAGGAGT ACCGACGGGA GCAAGGGTAG GGACGCGACG CTCGGAAGAG GAATGTCGGT

1601 TCCTCAGCCT GGACCTACGG CGGCGCCACT GCCAGCGCCT TGATGTGCTC TGCTGCTTCT CCAGTCCCTG CTCTGCTCAG GTGATTCAGA TCCTGCCCCA
     AGGAGTCGGA CCTGGATGCC GCCGCGGTGA CGGTCGCGGA ACTACACGAG AGACGAAGA GGTCAGGGAC GAGACGAGTC CACTAAGTCT AGGACGGGGT

1701 GGAGCTGGGG GACGGGACAG TACCAGTGGG CATTGCCCAC CTCACTGCCA CAGTTCAAGC CTTTACCCAC TGTGAAGCCA GCAGCCAGCA TGTGGTCACC
     CCTCGACCCC CTGCCCCTGTC ATGGTCACCC GTAACGGGTG GAGTGACGGT GTCAAGTTCG GAAATGGGTG ACACTTCGGT CGTCGGTCGT ACACCAGTGG

1801 ATCCTGCCTC CCCAAGCCCA CCTGGTGCCC CCACCTTCTG GAGCCTGGGG CTCTGAGCTC TTCAGCCCTG GAGGGTCCAC ACGGGACCTT CTAGGCCAGG
     TAGGACGGAG GGGTTCCGGT GGACCACGGG CGGTGGAAGAC CGAGTCGGAC AAGTCGGGAC CTCCCAGGTG TGCCCTGGAA GATCCGGTCC

1901 AGGAGGAGAC AAGGCAGAAG GCAGCCTGCA AGTCCCTGCC CTGTGCCCGC TGGAATCTTG CCCATTTCGC CCCGGAATTC CTGCAGCCCG GGGGATCCAC
     TCCTCCCCTG TTCCGTCTTC CGTCGGACGT TCAGGGACGG GACACGGGCG ACCTTAGAAC GGGTAAAGCG GGGCCTTAAG GACGTCGGGC CCCCTAGGTG

2001 TAGTTCTAGA GCGGCCGCCA CCGCGGTGGA GCTCCAGCTT TTGTTCCCTT TAGTGAGGGT TAATTGCGCG CTTGGGTATC TT
     ATCAAGATCT CGCCGGCGGT GGCGCCACCT CGAGGTCGAA AACAAGGGAA ATCACTCCCA ATTAACGCGC GAACCCATAG AA
```

METHODS OF SCREENING FOR AGONISTS AND ANTAGONISTS OF PATCHED-2

RELATED APPLICATIONS

This application is a continuation of U.S. Ser. No. 09/990,046, filed Nov. 20, 2001, which is a continuation of U.S. Ser. No. 09/293,505, filed Apr. 15, 1999, now U.S. Pat. No. 6,348,575, which claims the benefit under 35 §119 of U.S. Ser. No. 60/081,884, filed Apr. 15, 1998, now expired, the contents all of which are incorporated herein by reference.

FIELD OF THE INVENTION

The present invention relates generally to signaling molecules, specifically to signaling and mediator molecules in the hedgehog (Hh) cascade which are involved in cell proliferation and differentiation.

BACKGROUND OF THE INVENTION

Development of multicellular organisms depends, at least in part, on mechanisms which specify, direct or maintain positional information to pattern cells, tissues, or organs. Various secreted signaling molecules, such as members of the transforming growth factor-beta (TGF-β), Wnt, fibroblast growth factors and hedgehog families have been associated with patterning activity of different cells and structures in *Drosophila* as well as in vertebrates. Perrimon, *Cell:* 80: 517-520 (1995).

Segment polarity genes were first discovered in *Drosophila*, which when mutated caused a change in the pattern of structures of the body segments. These changes affected the pattern along the head to tail axis. Hedgehog (Hh) was first identified as a segment-polarity gene by a genetic screen in *Drosophila melanogaster*, Nusslein-Volhard et al., *Roux. Arch. Dev. Biol.* 193: 267-282 (1984), that plays a wide variety of developmental functions. Perrimon, supra. Although only one *Drosophila* Hh gene has been identified, three mammalian Hh homologues have been isolated: Sonic Hh (Shh), Desert Hh (Dhh) and Indian Hh (Ihh), Echelard et al., *Cell* 75: 1417-30 (1993); Riddle et al., *Cell* 75: 1401-16 (1993). Shh is expressed at high level in the notochord and floor plate of developing vertebrate embryos, and acts to establish cell fate in the developing limb, somites and neural tube. In vitro explant assays as well as ectopic expression of Shh in transgenic animals show that SHh plays a key role in neural tube patterning, Echelard et al. (1993), supra.; Ericson et al., *Cell* 81: 747-56 (1995); Marti et al., *Nature* 375: 322-5 (1995); Roelink et al. (1995), supra; Hynes et al., *Neuron* 19: 15-26 (1997). Hh also plays a role in the development of limbs (Krauss et al., *Cell* 75: 1431-44 (1993); Laufer et al., *Cell* 79, 993-1003 (1994)), somites (Fan and Tessier-Lavigne, *Cell* 79, 1175-86 (1994); Johnson et al., *Cell* 79: 1165-73. (1994)), lungs (Bellusci et al., *Develop.* 124: 53-63 (1997) and skin (Oro et al., *Science* 276: 817-21 (1997). Likewise, Ihh and Dhh are involved in bone, gut and germinal cell development, Apelqvist et al., *Curr. Biol.* 7: 801-4 (1997); Bellusci et al., *Dev. Suppl.* 124: 53-63 (1997); Bitgood et al., *Curr. Biol.* 6: 298-304 (1996); Roberts et al., *Development* 121: 3163-74 (1995). Specifically, Ihh has been implicated in chondrocyte development [Vortkamp, A. et al., *Science* 273: 613-22 (1996)] while Dhh plays a key role in testis development. Bitgood et al., supra. With the exception of the gut, in which both Ihh and Shh are expressed, the expression patterns of the hedgehog family members do not overlap. Bitgood et al., supra.

At the cell surface, Hh function appears to be mediated by a multicomponent receptor complex involving patched (e.g., Ptch) and Smoothened (e.g., Smo), two multi-transmembrane proteins initially identified as segment polarity genes in *Drosophila* and later characterized in vertebrates. Nakano et al., *Nature* 341: 508-513 (1989); Goodrich et al., *Genes Dev.* 10: 301-312 (1996); Marigo et al., *Develop.* 122: 1225-1233 (1996); van den Heuvel, M. & Ingham, P. W., *Nature* 382: 547-551 (1996); Alcedo, J. et al., *Cell* 86: 221-232 (1996); Stone, D. M. et al., *Nature* 384: 129-34 (1996). Upon binding of Hh to Patched, the normal inhibitory effect of Patched on Smo is relieved, allowing Smo to transduce the Hh signal across the plasma membrane. It remains to be established if the Patched/Smo receptor complex mediates the action of all 3 mammalian hedgehogs or if specific components exist. Interestingly, a second murine Patched gene, Patched-2 was recently isolated [Motoyama, J. et al., *Nature Genetics* 18: 104-106 (1998)], but its function as a Hh receptor has not been established. In order to characterize Patched-2 and compare it to Patched with respect to the biological function of the various Hh family members, Applicants have isolated the human Patched-2 gene. Biochemical analysis of Patched and Patched-2 show that both bind to all members of the Hh family with similar affinity and that both molecules can form a complex with Smo. However, the expression patterns of Patched-2 and Patched do not overlap. While Patched is expressed throughout the mouse embryo, Patched-2 is found mainly in spermatocytes which require Desert Hedgehog (Dhh) for proper development suggesting that Patched-2 mediates Dhh's activity in the testis. Chromosomal localization of Patched-2 places it on chromosome 1p33-34, a region deleted in some germ cell tumors, raising the possibility that Patched-2 may be a tumor suppressor in Dhh target cells.

SUMMARY OF THE INVENTION

In one embodiment, the invention provides an isolated nucleic acid molecule having at least about 80% sequence identity to (a) a DNA molecule encoding a patched-2 polypeptide comprising the sequence of amino acids 1 to 1203 of FIG. 1 (SEQ ID NO:2), or (b) the complement of the DNA molecule of (a); and encoding a polypeptide having patched-2 biological activity. The sequence identity preferably is >91%, more preferably about 92%, most preferably about 95%. In one aspect, the isolated nucleic acid has at least >91%, preferably at least about 92%, and even more preferably at least about 95% sequence identity with a polypeptide having amino acid residues 1 to about 1203 of FIG. 1 (SEQ ID NO:2). In a further aspect, the isolated nucleic acid molecule comprises DNA encoding a human patched-2 polypeptide having amino acid residues 1 to about 1203 of FIG. 1. In yet another aspect, the invention provides for an isolated nucleic acid comprising DNA having at least a 95% sequence identity to (a) a DNA molecule encoding the same mature polypeptide encoded by the cDNA in ATCC Deposit No. 209778 (designation: pRK7.hptc2.Flag-1405), alternatively the coding sequence of clone pRK7.hptc2.Flag-1405, deposited under accession number ATCC 209778. In a still further aspect, the invention provides for a nucleic acid comprising human patched-2 encoding sequence of the cDNA in ATCC Deposit No. 209778 (designation: pRK7.hptc2.Flag-1405) or a sequence which hybridizes thereto under stringent conditions.

In another embodiment, the invention provides a vector comprising DNA encoding a human patched-2 polypeptide. A host cell comprising such a vector is also provided. By way of example, the host cells may be mammalian cells, (e.g.

CHO cells), prokaryotic cells (e.g., *E. coli*) or yeast cells (e.g., *Saccharomyces cerevisiae*). A process for producing patched-2 polypeptides is further provided and comprises culturing host cells under conditions suitable for expression of patched-2 and recovering the same from the cell culture.

In yet another embodiment, the invention provides an isolated patched-2 polypeptide. In particular, the invention provides isolated native sequence patched-2 polypeptide, which in one embodiment is a human patched-2 including an amino acid sequence comprising residues 1 to about 1203 of FIG. 1 (SEQ ID NO:2). Human patched-2 polypeptides with or without the initiating methionine are specifically included. Alternatively, the invention provides a human patched-2 polypeptide encoded by the nucleic acid deposited under accession number ATCC 209778.

In yet another embodiment, the invention provides chimeric molecules comprising a patched-2 polypeptide fused to a heterologous polypeptide or amino acid sequence. An example of such a chimeric molecule comprises a patched-2 polypeptide fused to an epitope tag sequence or a constant region of an immunoglobulin.

In yet another embodiment, the invention provides expressed sequence tag (EST) comprising the nucleotide sequences identified in FIG. 2A (905531) and FIG. 2B (1326258).

In yet another embodiment, the invention provides for alternatively spliced variants of human patched-2 having patched-2 biological activity.

In yet another embodiment, the invention provides for method of using patched-2 for the treatment of disorders which are mediated at least in part by Hedgehog (Hh), especially Desert hedgehog (Dhh). In particular, testicular cancer. In yet another embodiment, the invention provides a method of using antagonists or agonists of patched-2 for treating disorders or creating a desirable physiological condition effected by blocking Hh signaling, especially Dhh signaling. (E.g, contraception).

BRIEF DESCRIPTION OF THE DRAWINGS

FIGS. 1A-1E shows the nucleotide (SEQ ID NO:1) and derived amino acid (SEQ ID NO:2) sequence of a native sequence of human Ptch-2 polypeptide.

FIG. 2A shows EST 905531 (SEQ ID NO:3) and FIG. 2B shows EST 1326258 (SEQ ID NO:5) in alignment with human Ptch (SEQ ID NO:18). These ESTs were used in the cloning of human full-length Ptch-2 (SEQ ID NO:1).

FIGS. 3A-3D show a comparison between human Ptch (SEQ ID NO:33) and Ptch-2 (SEQ ID NO:2). Gaps introduced for optimal alignment are indicated by dashes. Identical amino acids are boxed. The 12 transmembrane domains are indicated by the gray boxes, all of which are conserved between the two sequences. Alignment results between the two sequences indicate 53% identity. The most significant difference is a shorter C-terminal intracellular domain in human Ptch-2 (SEQ ID NO:2) in comparison with human Ptch (SEQ ID NO:33).

FIG. 4 shows a northern blot of Ptch-2 which indicates expression is limited to the testis. Multiple human fetal and adult tissue northern blots were probe fragments corresponding to the 3'-untranslated region of murine Ptch-2.

FIG. 5 shows a chromosomal localization of two BAC clones which were isolated by PCR screening with human patched-2 derived probes. Both probes were mapped by FISH to human chromosome 1p33-34.

FIGS. 6A-F is an in situ hybridization comparing Ptch, Ptch-2 and Fused (FuRK). High magnification of mouse testis showing expression of (A) Ptch, Ptch-2 (B) and FuRK (C). Low magnification of testis section hybridized with Ptch-2 sense (D) and anti-sense probe (E) respectively. FIG. 6(F) shows low magnification of testis section hybridized with FuRK. Scale bar: A, B, C, 0.05 mm; D, E, F: 0.33 mm.

FIG. 7A is logarithmic plot comparing the binding Ptch-2 to Dhh and Shh. Competitive binding of recombinant murine $^{125}$I-Shh to 293 cells overexpressing hPtch or hPtch-2. There was no detectable binding to mock transfected cells (data not shown).

FIGS. 8A-8D is a sequence comparison between human Ptch-2 (SEQ ID NO:2) and murine Ptch 2 (SEQ ID NO:7), which indicates that there is about 91% identity between the two sequences.

FIG. 9 is an in situ hybridization which demonstrates the accumulation of Ptch and Ptch-2 mRNA detected by in situ hybridization in basal cells of E18 transgenic mice overexpressing SMO-M2 (Xie et al., *Nature* 391: 90-92 (1998)).

FIGS. 10A-10E depict a partial sequence representing clone 3A (SEQ ID NO:8), a partial patched-2 fragment which was initially isolated from a fetal brain library.

FIGS. 11A-C depict a partial sequence representing clone 16.1 (SEQ ID NO:9), a partial patched-2 fragment which was isolated from a testis library.

DETAILED DESCRIPTION OF THE PREFERRED EMBODIMENTS

I. Definitions

Figure 7B:
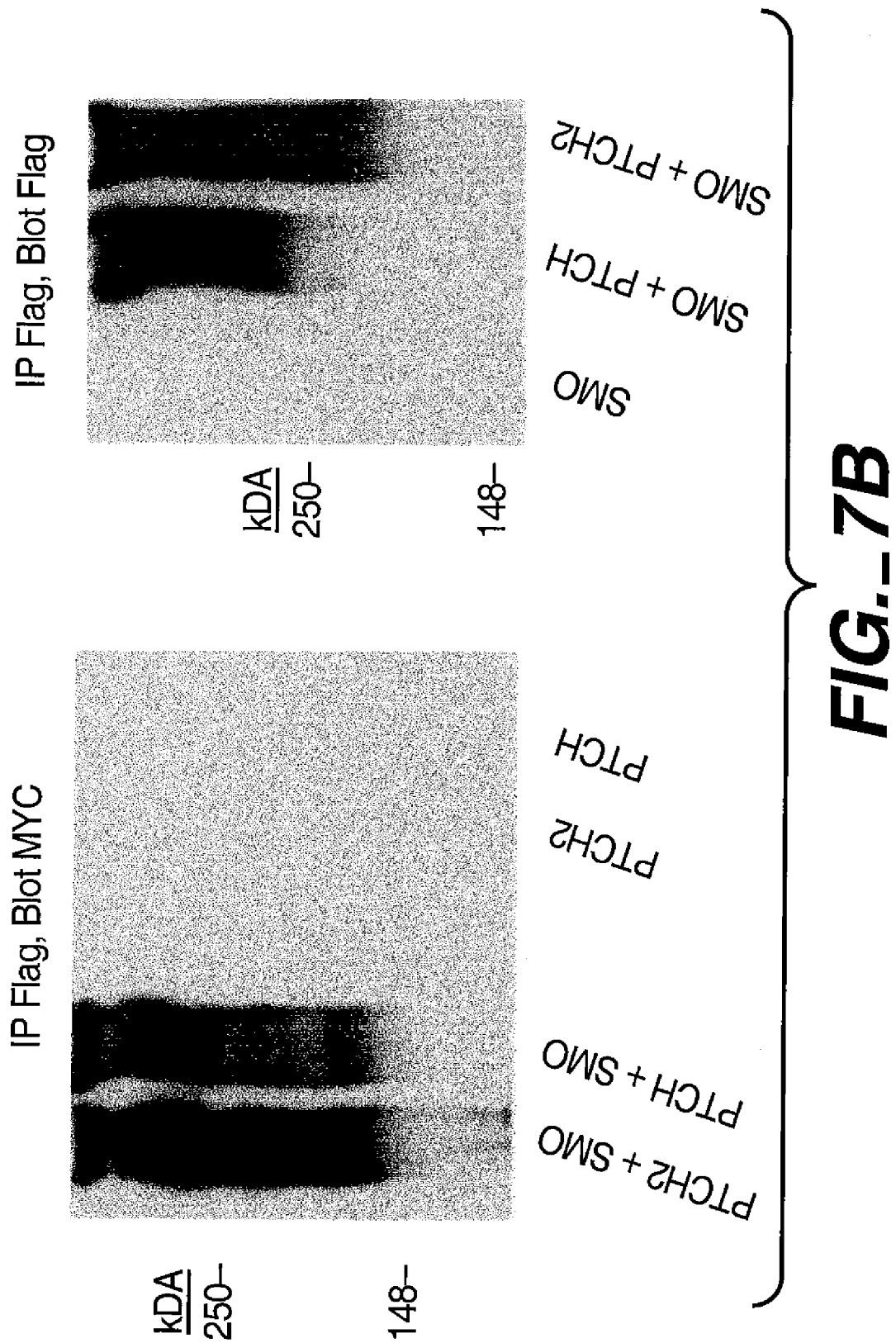
FIG. 7B is a western blot illustrating co-immunoprecipitation of epitope tagged Ptch or Ptch-2 with epitope tagged Smo. Immunoprecipitation was performed with antibodies to the Flag tagged Ptch and analyzed on a 6% acrylamide gel with antibodies to the Myc tagged Smo. Protein complexes can be detected for both Ptch and Ptch-2 with Smo. Ptch and Ptch-2 express at similar levels as shown by immunoprecipitation using antibodies to the Flag-tag and western blot using the same anti-Flag antibody.

The terms "patched-2" and "patched-2 polypeptide" when used herein encompass native sequence patched-2 and patched-2 variants (which are further defined herein) having patched-2 biological activity. Patched-2 may be isolated from a variety of sources, such as from testes tissue types or from another source, or prepared by recombinant or synthetic methods.

A "native sequence patched-2" comprises a polypeptide having the same amino acid sequence as a human patched-2 derived from nature. Such native sequence patched-2 can be isolated from nature or can be produced by recombinant and/or synthetic means. The term "native sequence vertebrate patched-2" specifically encompasses naturally occurring truncated forms of human patched-2, naturally occurring variant forms (e.g., alternatively spliced forms) and naturally-occurring allelic variants of human patched-2. Thus, one embodiment of the invention, the native sequence patched-2 is a mature or full-length native patched-2 comprising amino acids 1 to 1203 of FIG. 1 (SEQ ID NO:2) with or without the initiating methionine at position 1.

"Patched-2 variant" means an active human patched-2 as defined below having at least >91% amino acid sequence identity to (a) a DNA molecule encoding a patched-2 polypeptide, or (b) the complement of the DNA molecule of (a). In a particular embodiment, the patched-2 variant has at least >91% amino acid sequence homology with the human Ptch-2 having the deduced amino acid sequence shown in FIG. 1 for a full-length native sequence human patched-2. Such patched-2 variants include, without limitation, patched-2 polypeptides wherein one or more amino acid residues are added, or deleted, at the N- or C-terminus of the sequence of FIG. 1 (SEQ ID NO:2). Preferably, the nucleic acid or amino acid sequence identity is at least about 92%, more preferably at least about 93%, and even more preferably at least about 95%.

The term "Ptch" or "Ptch-2" refer to the particular species of molecules isolated and characterized in the application, while the terms "patched" and patched-2" refer to the more generalized description as defined above.

"Percent (%) amino acid sequence identity" with respect to the patched-2 sequences identified herein is defined as the percentage of amino acid residues in a candidate sequence that are identical with the amino acid residues in the patched-2 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST-2 software that are set to their default parameters. Those skilled in the art can determine appropriate parameters for measuring alignment, including any algorithms needed to achieve maximal alignment over the full length of the sequences being compared. Alternatively, % identity can be determined by Align-2, authored by Genentech, Inc., which was filed with user documentation in the United States Copyright Office, Washington, D.C. 20559, on Dec. 10, 1991, and is registered under U.S. Copyright Registration No. TXU 510087.

"Percent (%) nucleic acid sequence identity" with respect to the patched-2 sequences identified herein is defined as the percentage of nucleotides in a candidate sequence that are identical with the nucleotides in the patched-2 sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST-2 software that are set to their default parameters. Those skilled in the art can determine appropriate parameters for measuring alignment, including any algorithms needed to achieve maximal alignment over the full length of the sequences being compared. Alternatively, % identity can be determined by Align-2, authored by Genentech, Inc., which was filed with user documentation in the United States Copyright Office, Washington, D.C. 20559, on Dec. 10, 1991, and is registered under U.S. Copyright Registration No. TXU 510087.

The term "epitope tagged" when used herein refers to a chimeric polypeptide comprising patched-2 polypeptide, or a portion thereof, patched-2 to a "tag polypeptide". The tag polypeptide has enough residues to provide an epitope against which an antibody can be made, yet is short enough such that it does not interfere with activity of the patched-2 polypeptide. The tag polypeptide preferably also is fairly unique so that the antibody does not substantially cross-react with other epitopes. Suitable tag polypeptides generally have at least six amino acid residues and usually between about 8 to about 50 amino acid residues (preferably, between about 10 to about 20 residues).

As used herein, the term "immunoadhesin" designates antibody-like molecules which combine the binding specificity of a heterologous protein (an "adhesin") with the effector functions of immunoglobulin constant domains. Structurally, the immunoadhesin comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesins may be obtained from any immunoglobulin, such as IgG-1, IgG-2, IgG-3 or IgG-4 subtypes, IgA (including IgA-1 and IgA-2, IgE, IgD or IgM. Immunoadhesion reported in the literature include fusions of the T cell receptor* [Gascoigne et al., Proc. Natl. Acad. Sci. USA 84: 2936-2940 (1987)]; CD4* [Capron et al., Nature 337: 525-531 (1989); Traunecker et al., Nature 339: 68-70 (1989); Zettmeissl et al., DNA Cell Biol. USA 9: 347-353 (1990); Byrn et al., Nature 344, 667-670 (1990)]; L-selectin (homing receptor) [Watson et al., J. Cell. Biol. 110, 2221-2229 (1990); Watson et al, Nature 349, 164-167 (1991)]; CD44* [Aruffo et al., Cell 61, 1303-1313 (1990)]; CD28* and B7* [Linsley et al., J. Exp. Med. 173, 721-730 (1991)]; CTLA-4* [Lisley et al., J. Exp. Med. 174, 561-569 (1991)]; CD22* [Stamenkovic et al., Cell 66. 1133-1144 (1991)]; TNF receptor [Ashkenazi et al., Proc. Natl. Acad. Sci. USA 88, 10535-10539 (1991); Lesslauer et al., Eur. J. Immunol. 27, 2883-2886 (1991); Peppel et al., J. Exp. Med. 174 1483-1489 (1991)]; NP receptors [Bennett et al., J. Biol. Chem. 266, 23060-23067 (1991)]; IgE receptor α-chain* [Ridgway and Gorman, J. Cell. Biol. 115, abstr. 1448 (1991)]; HGF receptor [Mark, M. R. et al., J. Biol. Chem., 267(36): 26166-26171 (1992)], where the asterisk (*) indicates that the receptor is a member of the immunoglobulin superfamily.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends upon the ability of denatured DNA to reanneal when complementary strands are present in an environment near but below their $T^m$ (melting temperature). The higher the degree of desired homology between the probe and hybridizable sequence, the higher the relative temperature which can be used. As a result, it follows that higher relative temperatures would tend to make the reaction conditions more stringent, while lower temperatures less so. Moreover, stringency is also inversely proportional to salt concentrations. For additional details and explanation of stringency of hybridization reactions, see Ausubel et al., Current Protocols in Molecular Biology (1995).

"Stringent conditions," as defined herein may be identified by those that: (1) employ low ionic strength and high temperature for washing, for example 0.015 M sodium chloride/ 0.0015 M sodium citrate/0.1% sodium dodecyl sulfate at 50° C.; (2) employ during hybridization a denaturing agent, such as formamide, for example, 50% (vol/vol) formamide with 0.1% bovine serum albumin/1% Ficoll/0.1% polyvinylpyrrolidone/50 mM sodium phosphate buffer at pH 6.5 with 750 mM sodium chloride, 75 mM sodium citrate at 42° C.; (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the vertebrate patched-2 natural environment will not be present. Ordinarily, however, isolated polypeptide will be prepared by at least one purification step.

An "isolated" patched-2 nucleic acid molecule is a nucleic acid molecule that is identified and separated from at least one contaminant nucleic acid molecule with which it is ordinarily associated in the natural source of the patched-2 nucleic acid. An isolated patched-2 nucleic acid molecule is other than in the form or setting in which it is found in nature. Isolated patched-2 nucleic acid molecules therefore are distinguished from the corresponding native patched-2 nucleic acid molecule as it exists in natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single monoclonal antibodies (including agonist and antagonist antibodies), antibody compositions with polyepitopic specificity, as well as antibody fragments (e.g., Fab, F(ab')$_2$ and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1975), or may be made by recombinant DNA methods [see, e.g. U.S. Pat. No. 4,816,567 (Cabilly et al.)].

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity [U.S. Pat. No. 4,816,567; Cabilly et al.; Morrison et al., *Proc. Natl. Acad. Sci. USA* 81, 6851-6855 (1984)].

"Humanized" forms of non-human (e.g. murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, corresponding non-human residues replace Fv framework residues of the human immunoglobulin. Furthermore, humanized antibody may comprise residues that are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., *Nature* 321, 522-525 (1986); Reichmann et al., *Nature* 332, 323-329 (1988); Presta, *Curr. Op. Struct. Biol.* 2 593-596 (1992) and U.S. Pat. No. 5,225, 539 (Winter) issued Jul. 6, 1993.

"Active" or "activity" for the purposes herein refers to form(s) of patched-2 which retain the biologic and/or immunologic activities of native or naturally occurring patched-2. A preferred activity is the ability to bind to and affect, e.g., block or otherwise modulate, hedgehog, especially Desert hedgehog signaling. For example, the regulation of the pathogenesis of testicular cancer, male spermatocyte formation and basal cell carcinoma.

The term "antagonist" is used herein in the broadest sense to include any molecule which blocks, prevents, inhibits, neutralizes the normal functioning of patched-2 in the Hh signaling pathway. One particular form of antagonist includes a molecule that interferes with the interaction between Dhh and Ptch-2. Alternatively, an antagonist could also be a molecule which increases the levels of patched-2. In a similar manner, the term "agonist" is used herein to include any molecule which promotes, enhances or stimulates the binding of a Hh to patched-2 in the Hh signaling pathway (e.g., blocking binding of Ptch-2 to Smo). Suitable molecules that affect the protein-protein interaction of Hh and Ptch-2 and its binding proteins include fragments of the latter or small bioorganic molecules, e.g., peptidomimetics, which will prevent or enhance, as the case may be, the binding of Hh to Ptch-2. Non-limiting examples include proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Another preferred form of antagonist includes antisense oligonucleotides that inhibit proper transcription of wild type patched-2.

The term "modulation" or "modulating" means upregulation or downregulation of a signaling pathway. Cellular processes under the control of signal transduction may include, but are not limited to, transcription of specific genes; normal cellular functions, such as metabolism, proliferation, differentiation, adhesion, apoptosis and survival, as well as abnormal processes, such as transformation, blocking of differentiation and metastasis.

The techniques of "polymerase chain reaction," or "PCR", as used herein generally refers to a procedure wherein minute amounts of a specific piece of nucleic acid, RNA and/or DNA are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR sequences form total genomic DNA, and cDNA transcribed from total cellular RNA, bacteriophage, or plasmid sequences, etc. See generally Mullis et al., *Cold Spring Harbor Symp. Quant. Biol.* 51: 263 (1987); Erlich, Ed., PCR Technology, (Stockton Press, NY, 1989). As used herein, PCR is considered to be one, but not the only, example of a nucleic acid test sample comprising the use of a known nucleic acid as a primer and a nucleic acid polymerase to amplify or generate a specific piece of nucleic acid.

II. Compositions and Methods of the Invention

A. Full-Length Patched-2

Figure 3B:
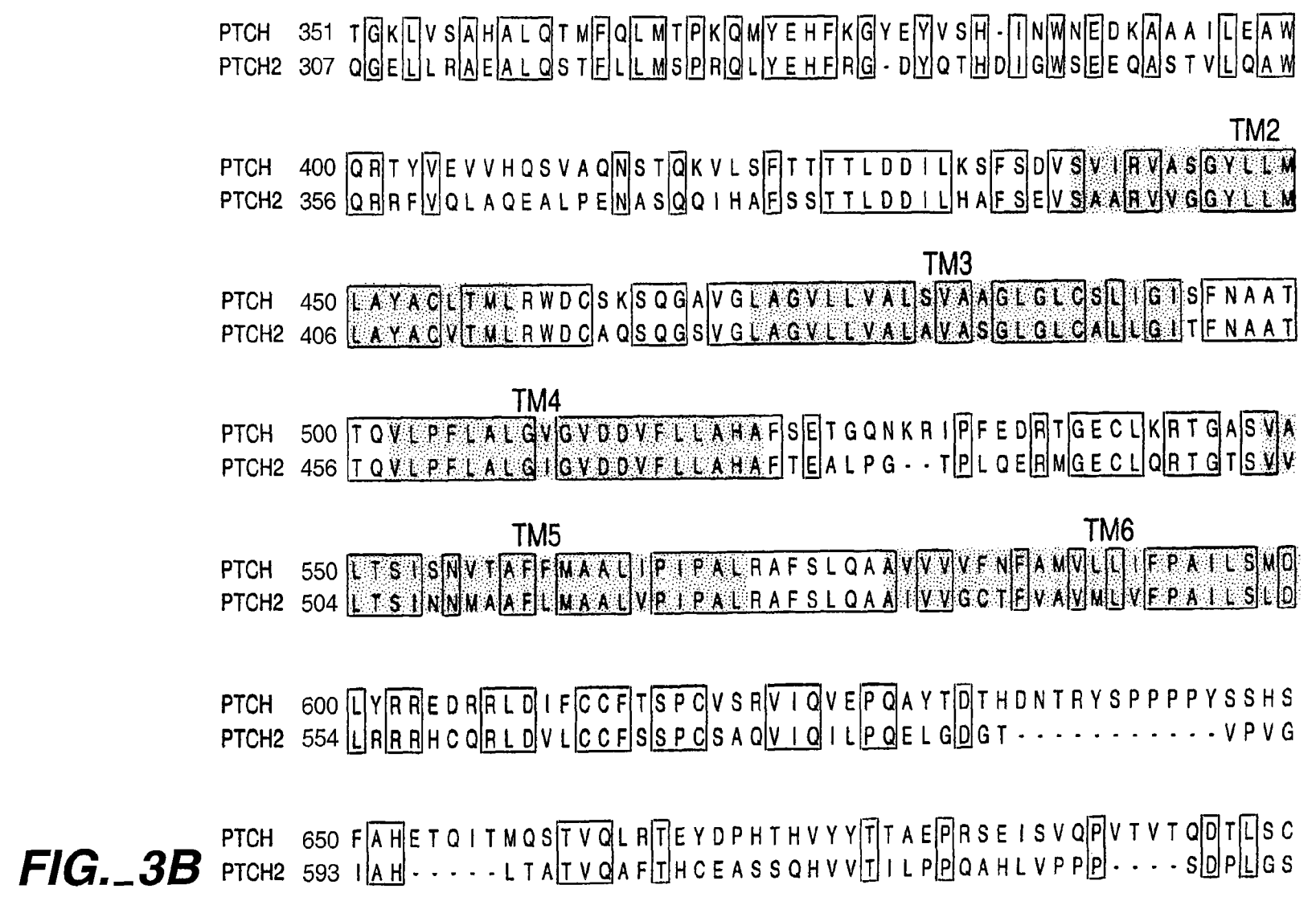

The present invention provides newly identified and isolated nucleotide sequences encoding polypeptides referred to in the present application as patched-2. In particular, Applicants have identified and isolated cDNA encoding a human patched-2 polypeptide, as disclosed in further detail in the Examples below. Using BLAST, BLAST-2 and FastA sequence alignment computer programs (set to the default parameters), Applicants found that a full-length native sequence human Ptch-2 (SEQ ID NO:2) (shown in FIG. 3) has 53% amino acid sequence identity with human patched (SEQ ID NO:33). Moreover human full-length patched-2 (SEQ ID NO:2) has about a 91% sequence identity with murine Ptch-2 (SEQ ID NO:7) (FIG. 8). Accordingly, it is presently believed that the human patched-2 (SEQ ID NO:2) disclosed in the present application is a newly identified member of the mammalian hedgehog signaling cascade, specifically Desert hedgehog.

The full-length native sequence of human patched-2 gene, or portions thereof, may be used as hybridization probes for a cDNA library to isolate the full-length gene or to isolate still other vertebrate homolog genes (for instance, those encoding naturally-occurring variants of patched-2 or patched-2 from other species) which have a desired sequence identity to the human patched-2 sequence disclosed in FIG. 1 (SEQ ID NO:2). Optionally, the length of the probes will be about 20 to about 50 bases. The hybridization probes may be derived from the nucleotide sequence of FIG. 1 (SEQ ID NO:1) or from genomic sequences including promoters, enhancer elements and introns of native sequence vertebrate patched-2. By way of example, a screening method will comprise isolating the coding region of the vertebrate patched-2 gene using the known DNA sequence to synthesize a selected probe of about 40 bases. Hybridization probes may be labeled by a variety of labels, including radionucleotides such as $^{32}$P or $^{35}$S, or enzymatic labels such as alkaline phosphatase coupled to the probe via avidin/biotin coupling systems. Labeled probes having a sequence complementary to that of the vertebrate patched-2 gene of the present invention can be used to screen libraries of human cDNA, genomic DNA or mRNA to determine which members of such libraries the probe hybridizes to.

B. Patched-2 Variants

In addition to the full-length native sequence patched-2 described herein, it is contemplated that patched-2 variants can be prepared. Patched-2 variants can be prepared by introducing appropriate nucleotide changes into a known patched-2 DNA, or by synthesis of the desired patched-2 polypeptides. Those skilled in the art will appreciate that amino acid changes may alter post-translational processes of patched-2.

Variations in the native full-length sequence patched-2 or in various domains of the patched-2 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the patched-2 that results in a change in the amino acid sequence of patched-2 as compared with the native sequence patched-2. Optionally, the variation is by substitution of at least one amino acid with any other amino acid in one or more of the domains of patched-2. Guidance in determining which amino acid residue may be inserted, substituted or deleted without adversely affecting the desired activity may be found by comparing the sequence of the patched-2 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vitro assay described in the Examples below.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl Acids Res.*, 10: 6487 (1987)], cassette mutagenesis [Wells et al., *Gene*, 34:315 (1985)], restriction selection mutagenesis [Wells et al., *Philos. Trans. R. Soc. London SerA,* 317:415 (1986)] or other known techniques can be performed on the cloned DNA to produce the vertebrate patched-2 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

In the comparison between human Ptch (SEQ ID NO:33) and Ptch-2 (SEQ ID NO:2) sequences depicted in FIG. 3, the 12 transmembrane domains are identified in gray, while identical residues are boxed. Gaps are indicated by dashes (–) and are inserted to maximize the total identity score between the two sequences.

C. Modifications of Patched-2

Covalent modifications of patched-2 are included within the scope of this invention. One type of covalent modification includes reacting targeted amino acid residues of patched-2 with an organic derivatizing agent that is capable of reacting with selected side chains or the N- or C-terminal residues of the vertebrate patched-2. Derivatization with bifunctional agents is useful, for instance, for crosslinking patched-2 to a water-insoluble support matrix or surface for use in the method for purifying anti-patched-2 antibodies, and vice-versa. Commonly used crosslinking agents include, e.g., 1,1-bis(diazo-acetyl)-2-phenylethane, glutaraldehyde, N-hydroxy-succinimide esters, for example, esters with 4-azidosalicylic acid, homobifunctional imidoesters, including disuccinimidyl esters such as 3,3'-dithiobis-(succinimidyl-propionate), bifunctional maleimides such as bis-N-maleimido-1,8-octane and agents such as methyl-3-[(p-azidophenyl)-dithio]proprioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the a-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of patched-2 comprises linking the patched-2 polypeptide to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337. Such modifications would be expected in increase the half-life of the molecules in circulation in a mammalian system; Extended half-life of patched-2 molecules might be useful under certain circumstances, such as where the patched-2 variant is administered as a therapeutic agent.

The patched-2 of the present invention may also be modified in a way to form a chimeric molecule comprising patched-2 bonded to another, heterologous polypeptide or amino acid sequence. In one embodiment, such a chimeric molecule comprises a fusion of patched-2 with a tag polypeptide, which provides an epitope to which an anti-tag antibody can selectively bind. The epitope tag is generally placed at the amino- or carboxyl-terminus of the patched-2. The presence of such epitope-tagged forms of the patched-2 can be detected using an antibody against the tag polypeptide. Also, provision of the epitope tag enables the patched-2 to be readily purified by affinity purification using an anti-tag antibody or another type of affinity matrix that binds to the epitope tag. In an alternative embodiment, the chimeric molecule may comprise a fusion of the patched-2 with an immunoglobulin or a particular region of an immunoglobulin. For a bivalent form of the chimeric molecule, such a fusion could be to the Fc region of an IgG molecule. Ordinarily, the C-terminus of a contiguous amino acid sequence of a patched-2 receptor is fused to the N-terminus of a contiguous amino acid sequence of an immunoglobulin constant region, in place of the variable region(s), however N-terminal fusions are also possible.

Typically, such fusions retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, immunoadhesins may be synthesized according to known methods.

The precise site at which the fusion is made is not critical; particular sites are well known and may be selected in order to optimize the biological activity, secretion or binding characteristics of the immunoadhesins.

In a preferred embodiment, the C-terminus of a contiguous amino acid sequence which comprises the binding site(s) of patched-2, at the N-terminal end, to the C-terminal portion of an antibody (in particular the Fc domain), containing the effector functions of an immunoglobulin, e.g., immunoglobulin $G_1$ (IgG-1). As herein above mentioned, it is possible to fuse the entire heavy chain constant region to the sequence containing the binding site(s). However, more preferably, a sequence beginning in the hinge region just upstream of the papain cleavage site (which defines IgG Fc chemically; residue 216, taking the first residue of heavy chain constant region to be 114 [Kobat et al., supra], or analogous sites of other immunoglobulins) is used in the fusion. Although it was earlier thought that in immunoadhesins the immunoglobulin light chain would be required for efficient secretion of the heterologous protein-heavy chain fusion proteins, it has been found that even the immunoadhesins containing the whole IgG1 heavy chain are efficiently secreted in the absence of light chain. Since the light chain is unnecessary, the immunoglobulin heavy chain constant domain sequence used in the construction of the immunoadhesins of the present invention may be devoid of a light chain binding site. This can be achieved by removing or sufficiently altering immunoglobulin heavy chain sequence elements to which the light chain is ordinarily linked so that such binding is no longer possible. Thus, the CH1 domain can be entirely removed in certain embodiments of the patched-2/immunoglobulin chimeras.

In a particularly preferred embodiment, the amino acid sequence containing the extracellular domain(s) of patched-2 is fused to the hinge region and CH2, CH3; or CH1, hinge, CH2 and CH3 domains of an IgG-1, IgG-2, IgG-3, or IgG-4 heavy chain.

In some embodiments, the patched-2/immunoglobulin molecules (immunoadhesins) are assembled as monomers, dimers or multimers, and particularly as dimers or tetramers. Generally, these assembled immunoadhesins will have known unit structures similar to those of the corresponding immunoglobulins. A basic four chain structural unit (a dimer of two immunoglobulin heavy chain-light chain pairs) is the form in which IgG, IgA and IgE exist. A four chain unit is repeated in the high molecular weight immunoglobulins; IgM generally exists as a pentamer of basic four-chain units held together by disulfide bonds. IgA globulin, and occasionally IgG globulin, may also exist in a multimeric form in serum. In the case of multimers, each four chain unit may be the same or different.

It is not necessary that the entire immunoglobulin portion of the patched-2/immunoglobulin chimeras be from the same immunoglobulin. Various portions of different immunoglobulins may be combined, and variants and derivatives of native immunoglobulins can be made as herein above described with respect to patched-2, in order to optimize the properties of the immunoadhesin molecules. For example, immunoadhesin constructs in which the hinge of IgG-1 was replaced with that of IgG-3 were found to be functional and showed pharmacokinetics comparable to those of immunoadhesins comprising the entire IgG-1 heavy chain.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8: 2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)]. A preferred tag is the influenza HA tag.

D. Preparation of Patched-2

The description below relates primarily to production of a particular patched-2 by culturing cells transformed or transfected with a vector containing patched-2 nucleic acid. It is, of course, contemplated that alternative methods, which are well known in the art, may be employed to prepare patched-2. For instance, the patched-2 sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the vertebrate patched-2 may be chemically synthesized separately and combined using chemical or enzymatic methods to produce the full-length patched-2.

1. Isolation of DNA Encoding Vertebrate Patched-2

DNA encoding patched-2 may be obtained from a cDNA library prepared from tissue believed to possess the patched-2 mRNA and to express it at a detectable level. Accordingly, human patched-2 DNA can be conveniently obtained from a cDNA library prepared from human tissue, such as described in the Examples. The vertebrate patched-2-encoding gene may also be obtained from a genomic library or by oligonucleotide synthesis.

Libraries can be screened with probes (such as antibodies to the patched-2 or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding vertebrate patched-2 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as BLAST, BLAST-2, ALIGN, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for patched-2 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of transfection are known to the ordinarily skilled artisan, for example, CaPO$_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology* 52:456-457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336: 348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for vertebrate patched-2-encoding vectors. *Saccharomyces cerevisiae* is a commonly used lower eukaryotic host microorganism.

Suitable host cells for the expression of vertebrate patched-2 are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR(CHO, Urlaub and Chasin, *Proc. Natl. Acad. Sci. USA*, 77:4216 (1980)); mouse sertoli cells (TM4, Mather, *Biol. Reprod.* 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding patched-2 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques, which are known to the skilled artisan.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV or BPV) are useful for cloning vectors in mammalian cells. A preferred replicable expression vector is the plasmid is pRK5. Holmes et al., *Science*, 253:1278-1280 (1991).

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the patched-2 nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the patched-2 nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding patched-2.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Patched-2 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Inserting an enhancer sequence into the vector may increase transcription of a DNA encoding the vertebrate patched-2 by higher eukaryotes. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the patched-2 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding patched-2.

Still other methods, vectors, and host cells suitable for adaptation to the synthesis of patched-2 in recombinant vertebrate cell culture are described in Gething et al., *Nature*, 293:620-625 (1981); Mantei et al., *Nature*, 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence patched-2 polypeptide or against a synthetic peptide based on the DNA sequences provided herein or against exogenous sequence patched-2 to patched-2 DNA and encoding a specific antibody epitope.

5. Purification of Polypeptide

Forms of patched-2 may be recovered from host cell lysates. Since patched-2 is membrane-bound, it can be released from the membrane using a suitable detergent solution (e.g. Triton-X 100) or by enzymatic cleavage. Cells employed in expression of patched-2 can be disrupted by various physical or chemical means, such as freeze-thaw cycling, sonication, mechanical disruption, or cell lysing agents.

It may be desired to purify patched-2 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the patched-2. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular patched-2 produced.

E. Uses for Patched-2

(1) Patched-2 is a Specific Receptor for Dhh

The hedgehog signaling pathway has been implicated in the formation of embryonic structures in mammals and invertebrates. The multi-pass transmembrane receptor Ptch, is a negative regulator of the hedgehog pathway, repressing the serpentine signaling molecule Smoothened (Smo). Data have shown that loss of Ptch leads to deregulation of the hedgehog pathway leading to formation of aberrant structures in the embryos and carcinoma in the adult.

Applicants' newly identified second human patched gene, termed patched-2, has a similar 12 transmembrane domain topology as does patched, and can bind to all the members of the Hh family and can complex with Smo. However, the expression patterns of Ptch-2 and Ptch do not overlap. Ptch-2 is expressed mainly in the developing spermatocytes, which are supported directly by the Dhh producing Sertoli cells, which suggests that Ptch-2 is a receptor for Desert hedgehog.

In the adult tubule, Sertoli cells, which are unusually large secretory cells, traverse the seminiferous tubule from the basal lamina to the luminal aspect, sending out cytoplasmic protrusions that engulf the germ cells. These contacts are particularly close during spermiogenesis, in which the haploid round spermatids undergo differentiation to produce the highly specialized, motile sperm. Tight junctions between adjacent Sertoli cells compartmentalize the tubule into a basal region, which contains mitotic spermatogonia and early spermtocytes, and an adluminal compartment, which contains meiotic spermatocytes and maturing spermatids. In fact, a Sertoli-derived cell line supports the meiotic progression of germ cells in culture, consistent with the view that factors derived from Sertoli cells contribute to germ cell maturation, Rassoulzadegan, M., et al., *Cell* 1993, 75: 997-1006. Loss of Dhh activity results in a recessive, sex-specific phentotype. Female mice homozygous for the mutation were fully viable and fertile, whereas male mice were viable but infertile. A gross examination indicated that, as early as 18.5 dpc, the testes of mutant males were noticeably smaller than those of heterozygous littermates. Bitgood et al., *Curr. Biol.*, 1996 6(3): 298-304. Thus, Sertoli cells likely independently regulate mitotic and meiotic stages of germ cell development during postnatal development. Therefore, since patched-2 appears to be the receptor for Dhh, molecules which modulate the binding of Dhh to Ptch-2 would affect the activation of Dhh signaling, and thereby would have utility in the treatment of conditions which are modulated by Dhh. (For example, testicular cancer). Alternatively, it is also provided that antagonists or agonists of patched-2 may be used for treating disorders or creating a desirable physiological condition effected by blocking Dhh signaling. (E.g, contraception, infertility treatment).

(2) General Uses for Patched-2

Nucleotide sequences (or their complement) encoding patched-2 have various applications in the art of molecular biology, including uses as hybridization probes, in chromosome and gene mapping and in the generation of anti-sense RNA and DNA. Patched-2 nucleic acid will also be useful for the preparation of patched-2 polypeptides by the recombinant techniques described herein.

The full-length native sequence patched-2 gene, or portions thereof, may be used as hybridization probes for a cDNA library to isolate the full-length gene or to isolate still other genes (for instance, those encoding naturally-occurring variants of patched-2) which have a desired sequence identity to the patched-2 sequence disclosed in FIG. 1 (SEQ ID NO:1). Optionally, the length of the probes will be about 20 to about 50 bases. The hybridization probes may be derived from the nucleotide sequence of FIG. 1 (SEQ ID NO:1) or from genomic sequences including promoters, enhancer elements and introns of native sequence patched-2. By way of example, a screening method will comprise isolating the coding region of the patched-2 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the patched-2 gene of the present invention can be used to screen libraries of human cDNA, genomic DNA or mRNA to determine to which members of such libraries the probe hybridizes. Hybridization techniques are described in further detail in the Examples below.

The probes may also be employed in PCR techniques to generate a pool of sequences for identification of closely related patched-2 sequences.

Nucleotide sequences encoding patched-2 can also be used to construct hybridization probes for mapping the gene, which encodes patched-2 and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Patched-2 polypeptides can be used in assays to identify the other proteins or molecules involved in complexing with patched-2 which ultimately results in the modulation of hedgehog signaling. Alternatively, these molecules can modulate the binding of patched-2 to Dhh. By such methods, inhibitors of the binding interaction can be identified. Proteins involved in such binding interactions can also be used to screen for peptide or small molecule inhibitors or agonists of the binding interaction. Also, the substrate of patched-2 can be used to isolate correlative complexing proteins. Screening assays can be designed to find lead compounds that mimic the biological activity of a native patched-2 or to find those that act as a substrate for patched-2. Such screening assays will include assays amenable to high-throughput screening of chemical libraries, making them particularly suitable for identifying small molecule drug candidates. Such small molecule inhibitors could block the enzymatic action of patched-2, and thereby inhibit hedgehog signaling. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode patched-2 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, was introduced into the animal or an ancestor of the animal at a prenatal, e.g., an embryonic stage. A transgene is a DNA sequence that is integrated into the genome of a cell from which a transgenic animal develops. In one embodiment, cDNA encoding patched-2 can be used to clone genomic DNA encoding patched-2 in accordance with established techniques and the genomic sequences used to generate transgenic animals that contain cells which express DNA encoding patched-2. Methods for generating transgenic animals, particularly animals such as mice or rats, have become conventional in the art and are described, for example, in U.S. Pat. Nos. 4,736,866 and 4,870,009. Typically, particular cells would be targeted for patched-2 transgene incorporation with tissue-specific enhancers. Transgenic animals that include a copy of a transgene encoding patched-2 introduced into the germ line of the animal at an embryonic stage can be used to examine the effect of increased expression of DNA encoding patched-2. Such animals can be used as tester animals for reagents thought to confer protection from, for example, pathological conditions associated with its overexpression.

Non-human homologues of vertebrate patched-2 can be used to construct a patched-2 "knock out" animal which has a defective or altered gene encoding patched-2 as a result of homologous recombination between the endogenous gene encoding patched-2 and altered genomic DNA encoding patched-2 introduced into an embryonic cell of the animal. For example, cDNA encoding patched-2 can be used to clone genomic DNA encoding patched-2 in accordance with established techniques. A portion of the genomic DNA encoding patched-2 can be deleted or replaced with another gene, such as a gene encoding a selectable marker that can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach,* E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the patched-2 polypeptide.

Suppression or inhibition (antagonism) of Dhh signaling is also an objective of therapeutic strategies. Since patched-2 can combine with all members of the hedgehog family (i.e., Shh, Dhh, Ihh), antagonist molecules which prevent the binding of hedgehog molecules to Ptch-2 have therapeutic utility. For example, SHh signaling is known to be activated in Basal Cell Carcinoma; Dhh is known to be involved in the regulation of spermatogenesis. Inhibitor or antagonist of Hh signaling would be effective therapeutics in the treatment of Basal Cell Carcinoma or male contraception, respectively.

The stimulation of Dhh signaling (agonism) is also an objective of therapeutic strategies. Since Ptch-2 also binds to the other members of the Hh family, Ihh and Shh, activating Dhh signaling would be useful in disease states or disorders characterized by inactive or insufficient Hh signaling. For example, degenerative disorders of the nervous system, e.g., Parkinson's disease, memory deficits, Alzheimer's disease, Lou Gehrig's disease, Huntington's disease, schizophrenia, stroke and drug addiction. Additionally, patched-2 agonists could be used to treat gut diseases, bone diseases, skin diseases, diseases of the testis (including infertility), ulcers, lung diseases, diseases of the pancreas, diabetes, osteoporosis.

F. Anti-Patched-2 Antibodies

The present invention further provides anti-vertebrate patched-2 antibodies. Exemplary antibodies include polyclonal, monoclonal, humanized, bispecific, and heteroconjugate antibodies.

1. Polyclonal Antibodies

The anti-patched-2 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the patched-2 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-patched-2 antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the patched-2 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications,* Marcel Dekker, Inc., New York, (1987) pp. 51-63].

The culture medium in which the hybridoma cells are cultured can then be assayed for the presence of monoclonal antibodies directed against patched-2. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Humanized Antibodies

The anti-patched-2 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct Biol.*, 2:593-596 (1992)].

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies [Cole et al., *Monoclonal Antibodies and Cancer Therapy*, Alan R. Liss, p. 77 (1985) and Boerner et al., *J. Immunol.*, 147(1):86-95 (1991)].

4. Bispecific Antibodies

Bispecific antibodies are monoclonal, preferably human or humanized, antibodies that have binding specificities for at least two different antigens. In the present case, one of the binding specificities is for the vertebrate patched-2, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

G. Uses for Anti-Patched-2 Antibodies

The anti-patched-2 antibodies of the invention have various utilities. For example, anti-patched-2 antibodies may be used in diagnostic assays for patched-2, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144: 945 (1962); David et al., *Biochemistry*, 13:1014 (1974); Pain et al., *J. Immunol Meth.*, 40:219 (1981); and Nygren, *J. Histochem. and Cytochem.*, 30:407 (1982).

Anti-patched-2 antibodies also are useful for the affinity purification of patched-2 from recombinant cell culture or natural sources. In this process, the antibodies against patched-2 are immobilized on a suitable support, such a Sephadex resin or filter paper, using methods well known in the art. The immobilized antibody then is contacted with a sample containing the patched-2 to be purified, and thereafter the support is washed with a suitable solvent that will remove substantially all the material in the sample except the patched-2, which is bound to the immobilized antibody. Finally, the support is washed with another suitable solvent that will release the patched-2 from the antibody.

Basal cell carcinoma (BCC) is the most common human cancer. The Hh signaling pathway was found to activated in all BCCs. Loss of Ptch function is thought to lead to unregulated Smo activity and is responsible for about half of all BCCs. Ptch being a target of the Hh pathway itself, increases in Ptch mRNA levels have been detected in BCC [Galiani, et al., Nature Genet. 14: 78-81 (1996)] as well as in animal models of BCC. Oro et al., Science 276: 817-821 (1997); Xie et al., Nature 391: 90-92 (1998). Abnormal activation of Sh signaling, such as that which occurs in BCC, was examined to confirm whether Ptch-2 expression was increased. As shown in FIG. 9, an in situ hybridization for Ptch (SEQ ID NO:4) and Ptch-2 in Smo-M2 transgenic mice (Xie et al., supra), while lower than Ptch, was still high in tumor cells. This suggests that therapeutic antibodies directed toward Ptch-2 may be useful for the treatment of BCC.

Anti-patched-2 antibodies also have utilities similar to those articulated for under the previous section "E. Uses of Patched-2". Depending on whether anti-patched-2 antibodies will bind patched-2 receptors so as to either inhibit Hh signaling (antagonist) or inhibit patched-2 complexing with Smo and thereby remove the normal inhibitory effect of Smo on Hh signaling (agonist) the antibody will have utilities corresponding to those articulated previously for patched-2.

H. Patched-2 Antagonists

Several approaches may be suitably employed to create the patched-2 antagonist and agonist compounds of the present invention. Any approach where the antagonist molecule can be targeted to the interior of the cell, which interferes or prevents wild type patched-2 from normal operation is suitable. For example, competitive inhibitors, including mutant patched-2 receptors which prevent wild type patched-2 from properly binding with other proteins necessary for Dhh and Hh signaling. Additional properties of such antagonist or agonist molecules are readily determinable by one of ordinary skill, such as size, charge and hydrophobicity suitable for transmembrane transport.

Where mimics or other mammalian homologues of patched-2 are to be identified or evaluated, the cells are exposed to the test compound and compared to positive controls which are exposed only to human patched-2, and to negative controls which were not exposed to either the compound or the natural ligand. Where antagonists or agonists of patched-2 signal modulation are to be identified or evaluated, the cells are exposed to the compound of the invention in the presence of the natural ligand and compared to controls which are not exposed to the test compound.

Detection assays may by employed as a primary screen to evaluate the Hh signaling inhibition/enhancing activity of the antagonist/agonist compounds of the invention. The assays may also be used to assess the relative potency of a compound by testing a range of concentrations, in a range from 100 mM to 1 pM, for example, and computing the concentration at which the amount of phosphorylation or signal transduction is reduced or increased by 50% ($IC_{50}$) compared to controls.

Assays can be performed to identify compounds that affect Hh signaling of patched-2 substrates. Specifically, assays can be performed to identify compounds that increase the phosphorylation activity of patched-2 or assays can be performed to identify compounds that decrease the Hh signaling of patched-2 substrates. These assays can be performed either on whole cells themselves or on cell extracts. The assays can be performed in a variety of formats, including protein-protein binding assays, biochemical screening assays, immunoassays, cell based assays, etc. Such assay formats are well known in the art.

The screening assays of the present invention are amenable to high-throughput screening of chemical libraries, and are particularly suitable for identifying small molecule drug candidates.

(1) Antagonist and Agonist Molecules

To screen for antagonists and/or agonists of patched-2 signaling, the assay mixture is incubated under conditions whereby, but for the presence of the candidate pharmacological agent, patched-2 induces hedgehog signaling with a reference activity. The mixture components can be added in any order that provides for the requisite hedgehog activity. Incubation may be performed at any temperature that facilitates optimal binding, typically between about 4° and 40° C., more commonly between about 15° and 40° C. Incubation periods are likewise selected for optimal binding but also minimized to facilitate rapid, high-throughput screening, and are typically between about 0.1 and 10 hours, preferably less than 5 hours, more preferably less than 2 hours. After incubation, the effect of the candidate pharmacological agent on the patched-2 signaling is determined in any convenient way. For cell-free binding-type assays, a separation step is often used to separate bound and unbound components. Separation may, for example, be effected by precipitation (e.g. TCA precipitation, immunoprecipitation, etc.), immobilization (e.g. on a solid substrate), followed by washing. The bound protein is conveniently detected by taking advantage of a detectable label attached to it, e.g. by measuring radioactive emission, optical or electron density, or by indirect detection using, e.g. antibody conjugates.

For example, a method of screening for suitable patched-2 antagonists and/or agonists could involve the application of Dhh and other hedgehog ligands. Such a screening assay could compare in situ hybridization in the presence and absence of the candidate antagonist and/or agonist in a patched-2 expressing tissue as well as confirmation or absence of patched-2 modulated cellular development. Typically these methods involve exposing an immobilized patched-2 to a molecule suspected of binding thereto and determining the level of ligand binding downstream activation of reporter constructs and/or evaluating whether or not the molecule activates (or blocks activation of) patched-2. In order to identify such patched-2 binding ligands, patched-2 can be expressed on the surface of a cell and used to screen libraries of synthetic candidate compounds or naturally-occurring compounds (e.g., from endogenous sources such as serum or cells).

Suitable molecules that affect the protein-protein interaction of patched-2 and its binding proteins include fragments of the latter or small molecules, e.g., peptidomimetics, which will inhibit ligand-receptor interaction. Such small molecules, which are usually less than 10 K molecular weight, are preferable as therapeutics since they are more likely to be permeable to cells, are less susceptible to degradation by various cellular mechanisms, and are not as apt to elicit an immune response as proteins. Small molecules include but are not limited to synthetic organic or inorganic compounds. Many pharmaceutical companies have extensive libraries of such molecules, which can be conveniently screened by using the assays of the present invention. Non-limiting examples include proteins, peptides, glycoproteins, glycopeptides, glycolipids, polysaccharides, oligosacchardies, nucleic acids, bioorganic molecules, peptidomimetics, pharmacological agents and their metabolites, transcriptional and translation control sequences, and the like.

A preferred technique for identifying molecules which bind to patched-2 utilizes a chimeric substrate (e.g., epitope-tagged patched-2 or patched-2 immunoadhesin) attached to a solid phase, such as the well of an assay plate. The binding of the candidate molecules, which are optionally labeled (e.g., radiolabeled), to the immobilized receptor can be measured. Alternatively, competition for various Hh pathways, especially Dhh (SEQ ID NO:13) can be measured. In screening for antagonists and/or agonists, patched-2 can be exposed to a patched-2 substrate followed by the putative antagonist and/or agonist, or the patched-2 binding protein and antagonist and/or agonist can be added simultaneously, and the ability of the antagonist and/or agonist to block patched-2 activation can be evaluated.

(2) Detection Assays

The patched-2 polypeptides are useful in assays for identifying lead compounds for therapeutically active agents that modulate patched-2 receptor/ligand hedgehog signaling. Specifically, lead compounds that either prevent the formation of patched-2 signaling complexes or prevent or attenuate patched-2 modulated hedgehog signaling (e.g, binding to patched-2) can be conveniently identified.

Various procedures known in the art may be used for identifying, evaluating or assaying the inhibition of activity of the patched-2 proteins of the invention. As patched-2 is believed to be a receptor for Dhh, but also binds Shh and Ihh, techniques known for use with identifying ligand/receptor modulators may also be employed with the present invention. In general, such assays involve exposing target cells in culture to the compounds and a) biochemically analyzing cell lysates to assess the level and/or identity of binding; or (b) scoring phenotypic or functional changes in treated cells as compared to control cells that were not exposed to the test substance. Such screening assays are described in U.S. Pat. No. 5,602,171, U.S. Pat. No. 5,710,173, WO 96/35124 and WO 96/40276.

(a) Biochemical Detection Techniques

Biochemical analysis can be evaluated by a variety of techniques. One typical assay mixture which can be used with the present invention contains patched-2 and a ligand protein with which patched-2 is normally associated (e.g., Dhh) usually in an isolated, partially pure or pure form. One or both of these components may be patched-2 to another peptide or polypeptide, which may, for example, provide or enhance protein-protein binding, improve stability under assay conditions, etc. In addition, one of the components usually comprises or is coupled to a detectable label. The label may provide for direct detection by measuring radioactivity, luminescence, optical or electron density, etc., or indirect detection such as an epitope tag, an enzyme, etc. The assay mixture can additionally comprise a candidate pharmacological agent, and optionally a variety of other components, such as salts, buffers, carrier proteins, e.g. albumin, detergents, protease inhibitors, nuclease inhibitors, antimicrobial agents, etc., which facilitate binding, increase stability, reduce nonspecific or background interactions, or otherwise improve the efficiency or sensitivity of the assay.

The following detection methods may also be used in a cell-free system wherein cell lysate containing the signal transducing substrate molecule and patched-2 is mixed with a compound of the invention. To assess the activity of the compound, the reaction mixture may be analyzed by the SDS-PAGE technique or it may be added to substrate-specific anchoring antibody bound to a solid support, and a detection procedure as described above is performed on the separated or captured substrate to assess the presence or absence of a patched-2 binding ligand. The results are compared to those obtained with reaction mixtures to which the compound is not added. The cell-free system does not require the natural ligand or knowledge of its identity. For example, Posner et al. (U.S. Pat. No. 5,155,031 describes the use of insulin receptor as a substrate and rat adipocytes as target cells to demonstrate the ability of pervanadate to inhibit PTP activity. Another example, Burke et al., *Biochem. Biophys. Res. Comm.* 204: 129-134 (1994) describes the use of autophosphorylated insulin receptor and recombinant PTP1B in assessing the inhibitory activity of a phosphotyrosyl mimetic.

(i) Whole Cell Detection

A common technique involves incubating cells with patched-2 and radiolabeled ligand, lysing the cells, separating cellular protein components of the lysate using an SDS-polyacrylamide gel (SDS-PAGE) technique, in either one or two dimensions, and detecting the presence of labeled proteins by exposing X-ray film. Detection can also be effected without using radioactive labeling. In such a technique, the protein components (e.g., separated by SDS-PAGE) are transferred to a nitrocellulose membrane where the presence of patched-ligand complexes is detected using an anti-ligand antibody.

Alternatively, the anti-patched-2 ligand antibody can be conjugated with an enzyme, such as horseradish peroxidase, and detected by subsequent addition of a colorimetric substrate for the enzyme. A further alternative involves detecting the anti-patched-2 ligand by reacting with a second antibody that recognizes anti-patched-2 ligand, this second antibody being labeled with either a radioactive moiety or an enzyme as previously described. Examples of these and similar techniques are described in Hansen et al., *Electrophoresis* 14: 112-126 (1993); Campbell et al., *J. Biol. Chem.* 268: 7427-7434 (1993); Donato et al., *Cell Growth Diff.* 3: 258-268 (1992); Katagiri et al., *J. Immunol* 150: 585-593 (1993). Additionally, the anti-patched-2 ligand can be detected by labeling it with a radioactive substance, followed by scanning the labeled nitrocellulose to detect radioactivity or exposure of X-ray film.

Further detection methods may be developed which are preferred to those described above. Especially for use in connection with high-throughput screening, it is expected that such methods would exhibit good sensitivity and specificity, extended linear range, low background signal, minimal fluctuation, compatibility with other reagents, and compatibility with automated handling systems.

The in vivo efficacy of the treatment of the present invention can be studied against chemically induced tumors in various rodent models. Tumor cell lines propagated in in vitro cell cultures can be introduced in experimental rodents, e.g. mice by injection, for example by the subcutaneous route. Techniques for chemical inducement of tumors in experimental animals are well known in the art.

(ii) Kinase Assays

Because patched-2 is a negative regulator of Hh signaling, which when activated by Hh releases the normal inhibitory effect on Smo, the inhibition of patched-2 binding to Smo can be measured by activation of various kinase substrate associated with Hh signaling. When the screening methods of the present invention for patched-2 antagonists/agonists are carried out as an ex vivo assay, the target kinase (e.g. fused) can be a substantially purified polypeptide. The kinase substrate (e.g., MBP, Gli) is a substantially purified substrate, which in the assay is phosphorylated in a reaction with a substantially purified phosphate source that is catalyzed by the kinase. The extent of phosphorylation is determined by measuring the amount of substrate phosphorylated in the reaction. A variety of possible substrates may be used, including the kinase itself in which instance the phosphorylation reaction measured in the assay is autophosphorylation. Exogenous substrates may also be used, including standard protein substrates such as myelin basic protein (MBP); yeast protein substrates; synthetic peptide substrates, and polymer substrates. Of these, MBP and other standard protein substrates may be regarded as preferred. Other substrates may be identified, however, which are superior by way of affinity for the kinase, minimal perturbation of reaction kinetics, possession of single or homogenous reaction sites, ease of handling and post-reaction recover, potential for strong signal generation, and resistance or inertness to test compounds.

Measurement of the amount of substrate phosphorylated in the ex vivo assay of the invention may be carried out by means of immunoassay, radioassay or other well-known methods. In an immunoassay measurement, an antibody (such as a goat or mouse anti-phosphoserine/threonine antibody) may be used which is specific for phosphorylated moieties formed during the reaction. Using well-known ELISA techniques, the phosphoserine/threonine antibody complex would itself be detected by a further antibody linked to a label capable of developing a measurable signal (as for example a fluorescent or radioactive label). Additionally, ELISA-type assays in microtitre plates may be used to test purified substrates. Peraldi et al., *J. Biochem.* 285: 71-78 (1992); Schraag et al., *Anal. Biochem.* 211: 233-239 (1993); Cleavland, *Anal. Biochem.* 190: 249-253 (1990); Farley, *Anal. Biochem.* 203: 151-157 (1992) and Lozaro, *Anal. Biochem.* 192: 257-261 (1991).

For example, detection schemes can measure substrate depletion during the kinase reaction. Initially, the phosphate source may be radiolabeled with an isotope such as $^{32}P$ or $^{33}P$, and the amount of substrate phosphorylation may be measured by determining the amount of radiolabel incorporated into the substrate during the reaction. Detection may be accomplished by: (a) commercially available scintillant-containing plates and beads using a beta-counter, after adsorption to a filter or a microtitre well surface, or (b) photometric means after binding to a scintillation proximity assay bead or scintillant plate. Weernink and Kijken, *J. Biochem. Biophs. Methods* 31: 49, 1996; Braunwalder et al., *Anal. Biochem.* 234: 23 (1996); Kentrup et al., *J. Biol. Chem.* 271: 3488 (1996) and Rusken et al., *Meth. Enzymol.* 200: 98 (1991).

Preferably, the substrate is attached to a solid support surface by means of non-specific or, preferably, specific binding. Such attachment permits separation of the phosphorylated substrate from unincorporated, labeled phosphate source (such as adenosine triphosphate prior to signal detection. In one embodiment, the substrate may be physically immobilized prior to reaction, as through the use of Nunc™ high protein binding plate (Hanke et al., *J. Biol. Chem.* 271: 695 (1996)) or Wallac ScintiStrip™ plates (Braunwalder et al., *Anal. Biochem.* 234: 23 (1996). Substrate may also be immobilized after reaction by capture on, for example, P81 phophocellulose (for basic peptides), PEI/acidic molybdate resin or DEAE, or TCA precipitation onto Whatman™ 3MM paper, Tiganis et al., *Arch. Biochem. Biophys.* 325: 289 (1996); Morawetz et al., *Mol. Gen. Genet.* 250; 17 (1996); Budde et al., *Int J. Pharmacognosy* 33: 27 (1995) and Casnellie, *Meth. Enz.* 200: 115 (1991). Yet another possibility is the attachment of the substrate to the support surface, as by conjugation with binding partners such as glutathione and streptavidin (in the case of GST and biotin), respectively) which have been attached to the support, or via antibodies specific for the tags which are likewise attached to the support.

Further detection methods may be developed which are preferred to those described above. Especially for use in connection with high-throughput screening, it is expected that such methods would exhibit good sensitivity and specificity, extended linear range, low background signal, minimal fluctuation, compatibility with other reagents, and compatibility with automated handling systems.

The in vivo efficacy of the treatment of the present invention can be studied against chemically induced tumors in various rodent models. Tumor cell lines propagated in in vitro cell cultures can be introduced in experimental rodents, e.g. mice by injection, for example by the subcutaneous route. Techniques for chemical inducement of tumors in experimental animals are well known in the art.

(b) Biological Detection Techniques:

The ability of the antagonist/agonist compounds of the invention to modulate the activity of patched-2, which itself modulates hedgehog signaling, may also be measured by scoring for morphological or functional changes associated with ligand binding. Any qualitative or quantitative technique known in the art may be applied for observing and measuring cellular processes which comes under the control of patched-2. The activity of the compounds of the invention can also be assessed in animals using experimental models of disorders caused by or related to dysfunctional hedgehog signaling. For example, ineffective Dhh hedgehog signaling in mice leads to viable but sterile mice. Additionally, proper Shh signaling is critical to murine embryonic development at the notochord and floor plate, neural tube, distal limb structures, spinal column and ribs. Improper Shh signaling, is also correlative with cyclopia. Any of these phenotypic properties could be evaluated and quantified in a screening assay for patched-2 antagonists and/or agonist. Disease states associated with overexpression of hedgehog is associated with basal cell carcinoma while inactive Shh signaling leads to improper neural development.

The data obtained from these cell culture assays and animal studies can be used in formulating a range of dosages for use in humans. The dosage of the compounds of the invention should lie within a range of circulating concentrations with little or no toxicity. The dosage may vary within this range depending on the dosage form employed and the route of administration.

(2) Antisense Oligonucleotides

Another preferred class of antagonists involves the use of gene therapy techniques, including the administration of antisense oligonucleotides. Applicable gene therapy techniques include single or multiple administrations of therapeutically effective DNA or mRNA. Antisense RNAs and DNAs can be used as therapeutic agents for blocking the expression of certain genes in vivo. Reference short antisense oligonucleotides can be imported into cells where they act as inhibitors, despite their low intracellular concentrations caused by restricted uptake by the cell membrane, Zamecnik et al., *Proc. Natl. Acad. Sci. USA* 83: 4143-4146 (1986). The anti-sense oligonucleotides can be modified to enhance their uptake, e.g., by substituting their negatively charged phophodiester groups by uncharged groups.

There are a variety of techniques known for introducing nucleic acids into viable cells. The techniques vary depending upon whether the nucleic acid is transferred into cultured cells in vitro, ex vivo, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection, Dzau et al., *Trends Biotech.* 11: 205-210 (1993). In some situations it is desirable to provide the nucleic acid source with an agent that targets the cells, such as an antibody specific for a cell surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262: 4429-4432 (1987); Wagner et al., *Proc. Natl. Acad. Sci. USA* 87: 3410-3414 (1990). For a review of known gene targeting and gene therapy protocols, see Anderson et al., *Science* 256: 808-813 (1992).

In one embodiment of the invention, patched-2 expression may be reduced by providing patched-2-expressing cells with an amount of patched-2 antisense RNA or DNA effective to reduce expression of the patched-2 protein.

I. Diagnostic Uses

Another use of the compounds of the invention (e.g., patched-2, patched-2 variant and anti-patched-2 antibodies) described herein is to help diagnose whether a disorder is driven, to some extent, by patched-2 or hedgehog signaling. For example, basal cell carcinoma cells are associated with active hedgehog signaling, spermatocyte formation is associated with Dhh signaling, and defective Ptch and Ptch-2 suppression may be associated with testicular carcinomas.

A diagnostic assay to determine whether a particular disorder is driven by Ptch-2 modulated hedgehog signaling, can be carried out using the following steps: (1) culturing test cells or tissues; (2) administering a compound which can prevent Ptch-2 binding with Smo, thereby activating the Hh signaling pathway; and (3) measuring the amount of Hh signaling. The steps can be carried out using standard techniques in light of the present disclosure. For example, standard techniques can be used to isolate cells or tissues and culturing or in vivo.

Compounds of varying degree of selectivity are useful for diagnosing the role of patched-2. For example, compounds which inhibit patched-2 in addition to another form of kinase can be used as an initial test compound to determine if one of several signaling ligands drive the disorder. The selective compounds can then be used to further eliminate the possible role of the other ligands in driving the disorder. Test compounds should be more potent in inhibiting ligand-patched-2 binding activity than in exerting a cytotoxic effect (e.g., an $IC_{50}/LD_{50}$ of greater than one). The $IC_{50}$ and $LD_{50}$ can be measured by standard techniques, such as an MTT assay, or by measuring the amount of LDH released. The degree of $IC_{50}/LD_{50}$ of a compound should be taken into account in evaluating the diagnostic assay. For example, the larger the $IC_{50}/LD_{50}$ ratio the more relative the information. Appropriate controls take into account the possible cytotoxic effect of a compound of a compound, such as treating cells not associated with a cell proliferative disorder (e.g., control cells) with a test compound, can also be used as part of the diagnostic assay. The diagnostic methods of the invention involve the screening for agents that modulate the effects of patched-2 upon hedgehog signaling. Exemplary detection techniques include radioactive labeling and immunoprecipitating (U.S. Pat. No. 5,385,915).

J. Pharmaceutical Compositions and Dosages

Therapeutic formulations of the compositions of the invention are prepared for storage as lyophilized formulations or aqueous solutions by mixing the patched-2 molecule, agonist and/or antagonist having the desired degree of purity with optional "pharmaceutically-acceptable" or "physiologically-acceptable" carriers, excipients or stabilizers typically employed in the art (all of which are termed "excipients"). For example, buffering agents, stabilizing agents, preservatives, isotonifiers, non-ionic detergents, antioxidants and other miscellaneous additives. (See Remington's Pharmaceutical Sciences, 16$^{th}$ Ed., A. Osol, Ed. (1980)). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives are added to retard microbial growth, and are added in amounts ranging from 0.2%-1% (w/v). Suitable preservatives for use with the present invention include phenol, benzyl alcohol, meta-cresol, methyl paraben, propyl paraben, octadecyldimethylbenzyl ammonium chloride, benzalconium halides (e.g., chloride, bromide, iodide), hexamethonium chloride, alkyl parabens such as methyl or propyl paraben, catechol, resorcinol, cyclohexanol, and 3-pentanol.

Isotonifiers sometimes known as "stabilizers" are present to ensure isotonicity of liquid compositions of the present invention and include polyhydric sugar alcohols, preferably trihydric or higher sugar alcohols, such as glycerin, erythritol, arabitol, xylitol, sorbitol and mannitol. Polyhydric alcohols can be present in an amount between 0.1% to 25% by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thiocitic acid, sodium thioglycolate, thioglycerol, α-monothioglycerol and sodium thio sulfate; low molecular weight polypeptides (i.e. <10 residues); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trisaccacharides such as raffinose; polysaccharides such as dextran. Stabilizers can be present in the range from 0.1 to 10,000 weights per part of weight active protein.

Non-ionic surfactants or detergents (also known as "wetting agents") are present to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.). Non-ionic surfactants are present in a range of about 0.05 mg/ml to about 1.0 mg/ml, preferably about 0.07 mg/ml to about 0.2 mg/ml.

Additional miscellaneous excipients include bulking agents, (e.g. starch), chelating agents (e.g. EDTA), antioxidants (e.g., ascorbic acid, methionine, vitamin E), and cosolvents.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences,* 16th edition, A. Osal, Ed. (1980).

The formulations to be used for in vivo administration must be sterile. This is readily accomplished, for example, by filtration through sterile filtration membranes.

Sustained-release preparations may be prepared. Suitable examples of sustained-release preparations include semi-permeable matrices of solid hydrophobic polymers containing the compounds of the invention, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compounds of the invention remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The amount of therapeutic polypeptide, antibody or fragment thereof which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans. However, based on common knowledge of the art, a pharmaceutical composition effective in modulating Dhh and Hh signaling may provide a local patched-2 protein concentration of between about 10 and 1000 ng/ml, preferably between 100 and 800 ng/ml and most preferably between about 200 ng/ml and 600 ng/ml of Ptch-2.

In a preferred embodiment, an aqueous solution of therapeutic polypeptide, antibody or fragment thereof is administered by subcutaneous injection. Each dose may range from about 0.5 μg to about 50 μg per kilogram of body weight, or more preferably, from about 3 μg to about 30 μg per kilogram body weight.

The dosing schedule for subcutaneous administration may vary from once a week to daily depending on a number of clinical factors, including the type of disease, severity of disease, and the subject's sensitivity to the therapeutic agent.

Patched-2 polypeptide may comprise an amino acid sequence or subsequence thereof as indicated in FIG. 1 (SEQ ID NO:2), active amino acid sequence derived therefrom, or functionally equivalent sequence as this subsequence is believed to comprise the functional portion of the patched-2 polypeptide.

If the subject manifests undesired side effects such as temperature elevation, cold or flu-like symptoms, fatigue, etc., it may be desirable to administer a lower dose at more frequent intervals. One or more additional drugs may be administered in combination with patched-2 to alleviate such undesired side effects, for example, an anti-pyretic, anti-inflammatory or analgesic agent.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Rockville, Md.

Example 1

Introduction

At the cell surface, Hh function appears to be mediated by a multicomponent receptor complex involving Ptch and Smo, two multi-transmembrane proteins initially identified as segment polarity genes in *Drosophila* and later characterized in vertebrates. Nakano, Y. et al., *Nature* 341: 508-513 (1989); Goodrich et al., *Gene Dev.* 10: 301-312 (1996); Marigo et al., *Develop.* 122: 1225-1233 (1996); van den Heuvel et al., *Nature* 382: 547-551 (1996); Alcedo et al., *Cell* 86: 221-232 (1996); Stone et al. *Nature* 384: 129-34 (1996). Both genetic and biochemical evidence support the existence of a receptor complex where Ptch (SEQ ID NO:4) is the ligand binding subunit, and where Smo, a G-protein coupled receptor like molecule, is the signaling component. Stone et al., *Nature* 384: 129-134 (1996), Marigo et al., *Nature* 384: 176-79 (1996), Chen et al., *Cell* 87: 553-63 (1996). Upon binding of Hh to Ptch, the normal inhibitory effect of Ptch on Smo is relieved, allowing Smo to transduce the Hh signal across the plasma membrane.

Results:

It remains to be established if the patched-Smoothened receptor complex mediates the action of all 3 mammalian Hhs or if specific components exist. Recently, a second murine patched gene, Ptch-2 was recently isolated [Motoyama et al., *Nature Genet.* 18: 104-106 (1998)] but its function as a Hh receptor has not been established. In order to characterize Ptch-2 and compare it to Ptch with respect to the biological function of the various Hh family members, we have screened EST databases with the Ptch protein and identified 2 EST candidates for a novel human patched gene. A full length cDNA encoding human Ptch-2 was cloned from a testis library. The initiation ATG defines a 3612 nucleotide open reading frame encoding a 1204 amino acid long protein with a predicted molecular weight of approximately 131 kDa. The overall identity between human Ptch (SEQ ID NO:33) and Ptch-2 (SEQ ID NO:2) is 54% (FIG. 1), while the identity between human Ptch-2 (SEQ ID NO:2) and the recently described mouse Ptch 2 (SEQ ID NO:7) is 90%. (FIG. 8). The most obvious structural difference between the two human Ptch proteins is a truncated C-terminal cytoplasmic domain in Ptch-2. In addition, only one of the two glycosylation sites present in Ptch is conserved in Ptch-2.

To determine if Ptch-2 is a Hh receptor and if the two patched molecules are capable of discriminating between the various Hh ligands through specific binding, Applicants transfected human 293 embryonic kidney cells with Ptch or Ptch-2 expression constructs and analyzed the cells for binding of Shh, Dhh and Ihh. As shown on FIG. 7A, binding of $^{125}$I-Shh can be competed with an excess of Shh, Dhh or Ihh. Scatchard analysis of the displacement curves indicates that all Hhs have similar affinity for Ptch (Shh, 1.0 nM; Dhh, 2.6 nM; Ihh, 1.0 nM) and Ptch-2 (Shh, 1.8 nM; Dhh, 0.6 nM; Ihh, 0.4 nM) indicating that both Ptch and Ptch-2 can serve as physiological receptors for the 3 mammalian Hh proteins.

Applicants next determined whether, like Ptch, Ptch-2 forms a physical complex with Smo. Expression constructs for Flag-tagged Ptch or Ptch-2 were transiently co-transfected in 293 cells with Myc-tagged Smo. As described previously [Stone et al., *Nature* 384: 129-34 (1996)], in cells expressing Ptch and Smo, Ptch can be immunoprecipitated with antibodies against the epitope-tagged Smo (FIG. 7B). Similarly, Ptch-2 can be immunoprecipitated with antibodies against the epitope-tagged Smo when the two proteins are co-expressed in 293 cells. Together, these results suggest a model where Ptch-2 forms a multicomponent Hh receptor complex with Smo similar to the one described for patched (Stone et al., supra). Interestingly, these results also demonstrate that the long C-terminal tail which is missing in Ptch-2 is not required for the interaction with Smo as was already suggested by the analysis of truncated patched (Stone et al., supra). However, it remains possible that the absence of a C-terminal domain affects the capacity of Ptch-2 to block signaling by Smo or leads to difference in signaling by patched compared to patched-2.

To further investigate whether patched-2 could mediate the action of a specific Hh molecule based on its expression profile, Applicants have compared the expression pattern of Ptch and Ptch-2. First, Northern blot analysis using a probe specific for Ptch-2 revealed high levels of patched-2 mRNA in the testis (FIG. 4). By this method, Ptch-2 expression was not detected in any other tissue analyzed including embryonic tissues (data not shown). This profile is very different from the one observed for Ptch which was not found in testis by Northern blot but in a large number of adult and embryonic tissues [Goodrich et al., *Genes Dev.* 10: 301-312 (1996)]. More detailed analysis of the expression pattern of Ptch and Ptch-2 was performed by in situ hybridization with particular attention to testis. As previously described (Motoyama et al., supra), low levels of Ptch-2 expression were detected in epithelial cells of the developing tooth and skin (data not shown). High levels of Ptch-2 are expressed inside the seminiferous tubule, on the primary and secondary spermatocytes (FIG. 6B,6E) while only low levels of Ptch can be detected on the Leydig cells located in the interstitium of the seminiferous tubules (FIG. 6A). The primary and secondary spermatocytes are in close contact with the supporting Sertoli cells, the source of Dhh in the testis [Bitgood et al., *Curr. Biol.* 6: 298-304 (1996)]. To determine which one of the 2 receptors is the most relevant mediator of Dhh activity in the testis, we have analyzed the expression profile of FuRK, a Fused Related Kinase that was shown to be a component of the Hh signaling pathway (Zhang et al., submitted; copending U.S.S.N. Ser. No. 09/031,563, filed 26 Feb. 1998). Consistent with the idea that Ptch-2 is the target of Dhh in the testis, we found that FuRK is expressed only in germ cells where it colocalizes with Ptch-2 (FIG. 4c,f). Dhh is required for proper differentiation of germ cells since male Dhh-deficient mice are sterile due to lack of mature sperm (Bitgood et al., supra). Our data suggest that Dhh acts directly on germ cells through Ptch-2 while the function of Ptch expressed at low levels on testosterone producing Leydig cells is unclear.

Discussion:

Loss of heterozygosity (LOH) for patched was reported to occur with high frequency in familial as well as sporadic basal cell carcinoma [Johnson et al., *Science* 272: 1668-71 (1996); Hahn et al., *Cell* 85: 841-51 (1996); Gailani et al., *Nature Genetics* 14: 78-81; Xie et al., *Cancer Res.* 57: 2369-72 (1997)], suggesting that it functions as a tumor suppressor. According to the receptor model described above, loss of patched function may result in aberrant signaling by Smo, leading to hyperproliferation of the skin basal cell layer. If, as suggested above, patched-2 mediates the function of Dhh, loss of Ptch-2 may lead to tumor formation in tissues where Smo activity is controlled by patched-2. The gene encoding patched-2 was mapped by fluorescence in situ hybridization and by PCR using a radiation hybrid panel to human chromosome 1p33-34 (data not shown). Interestingly, recent analysis of recurrent chromosomal abnormalities in testicular tumors, including seminomas, revealed a deletion of the region 1p32-36 [Summersgill et al., *B. J. Cancer* 77: 305-313 (1998)]. Loss of this region encompassing the patched-2 locus was consistent in 36% of the germ cell tumor cases. These data raise the possibility that, like patched in basal cell carcinoma and medulloblastoma, patched-2 may be a tumor suppressor in Dhh target cells such as spermatocytes, further implicating Hh signaling in cancer.

In summary, our data demonstrate that both patched and patched-2 are genuine Hh receptors and that they are both capable of forming a complex with Smo. Although binding data indicate that patched and patched-2 do not discriminate between the various Hh ligands through affinity differences, the distinct tissue distribution of these 2 receptors suggests that in vivo, patched may be the primary receptor for Shh whereas Ptch-2 will mediate mainly Dhh signaling. The function of patched expression in Leydig cells in the absence of some of the Hh signaling components remain to be explained. Similarly, it will be of interest to determine if patched-2 plays a role when expressed in Shh expressing cells present in the developing tooth and skin Motoyama et al., *Nature Genet.* 18: 104-106 (1998). Finally, the existence of patched-2 raises the question of whether additional patched receptors exist, in particular one that mediates the function of Ihh.

Material and Methods:

1. Isolation of Human Patched-2 cDNA Clones

An expressed sequence tag (EST) DNA database (LIFESEQ®, Incyte Pharmaceuticals, Palo Alto, Calif.) was searched for a human homologue of the Drosophila segment polarity gene patched-2. Two ESTs (Incyte #905531 and 1326258) (FIGS. 2A & 2B) (SEQ ID NOS:3 and 5, respectively) were identified as a potential candidates. In order to identify human cDNA libraries containing human patched-2 clones, human cDNA libraries in pRK5 were first screened by PCR using the following primers:

```
5'-905531(A):
5'-AGGCGGGGATCACAGCA-3'      (SEQ ID NO: 19)

3'-905531(A):
5'-ATACCAAAGAGTTCCACT-3'     (SEQ ID NO: 20)
```

A fetal lung library was selected and enriched for patched-2 cDNA clones by extension of single stranded DNA from plasmid libraries grown in dut⁻/ung⁻ host using the 3'-905531 (A) primer in a reaction containing 10 µl of 10×PCR Buffer (Klentaq®), 1 µl dNTP (200 µM), 1 µl library DNA (200 ng), 0.5 µl primer, 86.5 µl H₂O and 1 µl of Klentaq® (Clontech) added after a hot start. The reaction was denatured for 1 min. at 95° C., annealed for 1 min. at 60° C. then extended for 20 min. at 72° C. DNA was extracted with phenol/CHCl₃, ethanol precipitated, then transformed by electroporation into DH10B (Gibco/BRL) host bacteria. Colonies from each transformation were replica plated on nylon membranes and screened with an overlapping oligo probe derived from the EST sequence (#905531) of the following sequence:

```
5'-Ptch2 probe:
5'-CTGCGGCGCTGCTTCCTGCTGGCCGTCTGCAT  (SEQ ID NO: 21)
CCTGCTGGTGTGC-3'

3'-Ptch2 probe:
5'-AGAGCACAGACGAGGAAAGTGCACACCAGCAG  (SEQ ID NO: 22)
GATGCAGACGGCC-3'
```

The oligo probe was labeled with [α-³²P]-ATP and T4 polynucleotide kinase. Filters were hybridized overnight at 42° C. in 50% formamide, 5×SSC, 10×Denhardt's, 0.05M sodium phosphate (pH 6.5), 0.1% sodium pyrophosphate, 50 µg/ml of sonicated salmon sperm DNA. The filters were then rinsed in 2×SSC and washed in 0.1×SSC, 0.1% SDS then exposed to Kodak® X Ray films.

Using this procedure, a partial clone was isolated from the fetal brain library (clone 3A—FIG. 10) (SEQ ID NO:8). In order to isolate the missing 5'-sequence, a testis library (see northern blot analysis, infra) was screened. The primer set used to amplify a 204 by probe from clone 3A to probe the testis library was:

```
RACE 5:
5'-ACTCCTGACTTGTAGCAGATT-3'   (SEQ ID NO: 23)
and

RACE 6:
5'-AGGCTGCATACACCTCTCAGA-3'.  (SEQ ID NO: 24)
```

The amplified probe was purified by excision from an agarose gel and labeled with a random primer labeling kit (Boehringer Mannheim). Several clones were isolated, including one (clone 16.1—FIG. 11 (SEQ ID NO:9)) containing a potential initiation methionine. A full length cDNA encoding patched-2 was reconstructed by assembling several of these clones. The full length cDNA encoding human Ptch-2 (FIG. 1) (SEQ ID NO:1) has a 3612 nucleotide long open reading frame encoding a 1204 amino acid protein with a 144 kDa predicted molecular weight. Alignment with human Ptch reveals a 53% identity between the 2 molecules at the amino acid level (FIG. 3). All 12 transmembrane domains are conserved. The most significant difference is a shorter C-terminal intracellular domain in Ptch-2 compared to Ptch.

2. Northern blot analysis:

In order to determine the best tissue source for isolation of the complete full length Ptch-2 cDNA as well as to determine its expression profile, we probed human multiple tissue northern blots (Clontech) with a 752 by fragment amplified from the 3' untranslated region of Ptch-2 using the following primers:

```
TM2: TM2
5-GCTTAGGCCCGAGGAGAT-3'       (SEQ ID NO: 25)

UTR2:
5'-AACTCACAACTTTCTCTCCA-3'.   (SEQ ID NO: 26)
```

The resulting fragment was gel purified and labeled by random priming. The blots were hybridized in ExpressHyb® hybridization solution (Clontech) in the presence of 1×10⁶ cpm/ml ³²P-labeled probe at 42° C. overnight. The blots were washed in 2×SSC at room temperature for 10 minutes and washed in 0.1×SSC/0.1% SDS at 42° C. for 30 minutes then exposed to x-ray film overnight. FIG. 4 shows that Ptch-2 message is expressed at high levels in only the testis.

3. Chromosomal Localization:

The primers TM2 (SEQ ID NO:25) and UTR2 (SEQ ID NO:26) described above were used to screen the Genome Systems (St. Louis, Mo.) BAC library. Two individual BAC clones were obtained from this library and chromosomal localization of both of the clones by FISH indicated that Ptch-2 maps to human chromosome 1p33-34 (FIG. 5). Loss of heterozyosity (LOH) for patched was reported to occur with high frequency in basal cell carcinoma. Loss of patched function is thought to lead to constitutive signaling by Smoothened (Smo), resulting in hyperproliferation of the basal layer of the dermis. A similar mechanism may lead to the formation of germ cell tumors. This model proposes that the first step in the progression of a germ cell tumor is an initial loss of DNA by a germ cell precursor, leading to a neoplastic germ cell which then forms a seminoma [De Jong et al., *Cancer Genet. Cytogenet.* 48: 143-167 (1990)]. From the invasive seminoma, all other forms of germ cell tumor types develop. Approximately 80% of all germ cell tumors correlate with an isochromosome 12p (i12p) and is found at a higher frequency in non-seminomas than seminomas [Rodriguez et al., *Cancer Res.* 52: 2285-2291 (1992)]. However, analysis of recurrent chromosomal abnormalities in testicular tumors including seminomas revealed a deletion of the region 1p32-36. Loss of this region was consistent in 36% of the germ cell tumor cases of in a recent study Summersgill et al., *B. J. Cancer* 57: 305-313 (1998)]. A similar deletion of chromosome 1p32-36 has been reported at a frequency of 28% in oligodendrogliomas Bello, et al., *Int. J. Cancer* 57: 172-175 (1994). While expression of patched-2 in the brain was not examined here in detail, patched-2 is thought to be the Dhh receptor (see below) and expression of Dhh by murine Schwann cells was previously reported [Bitgood et al, *Develop. Biol.* 172: 126-138 (1995)]. Since patched-2 localizes to chromosome 1p33-34 it is possible that patched-2 regulates Smo signaling in Dhh target cells and that loss of patched-2 function leads to abnormal Smo signaling in these cells and subsequent tumor formation.

4. In Situ Hybridization:

Mouse testis sections were cut at 16 µm, and processed for in situ hybridization by the method described in Phillips et al., *Science* 250: 290-294 (1990). $^{33}$P-UTP labeled RNA probes were generated as described in Melton et al., *Nucleic Acids Res.* 12: 7035-7052 (1984). Sense and antisense probes were synthesized from the 3' non coding region of the mouse Ptch or Ptch-2 and from a mouse FuRK cDNA fragment corresponding to the region encoding amino acid 317-486 of the human sequence using T3 and T7, respectively.

```
Ptch:
503 (Anti-sense)
5'GGATTCTAATACGACTCACTATAGGGCCCAATG    (SEQ ID NO: 27)
GCCTAAACCGACTGC3'

503 (Sense)
5'CTATGAAATTAACCCTCACTAAAGGGACCCACG    (SEQ ID NO: 28)
GCCTCTCCTCACA3'

Ptch2:
504 (Anti-sense)
5'GGATTCTAATACGACTCACTATAGGGCCCCTAA    (SEQ ID NO: 12)
ACTCCGCTGCTCCAC3'

504 (Sense)
5'CTATGAAATTAACCCTCACTAAAGGGAGCTCCC    (SEQ ID NO: 11)
GTGAGTCCCTATGTG3'
```

FuRK sense and antisense were synthesized from a mouse fused DNA fragment using T3 and T7, respectively, corresponding to the region encoding amino acid residues 317-486 of the human sequence (Zhang et al., submitted, 1998; copending U.S. Ser. No. 09/031,563, filed 26 Feb. 1998).

FIG. 6 illustrates that, although both Ptch and Ptch-2 are expressed in testis, their expression pattern does not overlap. Ptch is expressed in the Leydig cells of the interstitium while Ptch-2 is expressed in the primary and secondary spermatocytes.

The expression of Ptch-2 specifically in the developing spermatogonia suggest that Ptch-2 is the immediate target of Dhh. Dhh is expressed by Sertoli cells and mice deficient in Dhh are sterile because of a defect in sperm production [Bitgood et al., *Curr. Biol.* 6: 298-304 (1996)]. Although this effect on germ cells was though to be indirect and mediated by Ptch present on Leydig cells, our data suggest that Dhh directly acts on germ cells through Ptch-2. This is further demonstrated by the localization of FuRK, an intracellular kinase homologous to *Drosophila* Fused and involved in transducing the Hedgehog (Hh) signal. As shown in FIG. 6, FuRK is colocalizes with Ptch-2 in germ cells and not with Ptch in Leydig cells, suggesting that Ptch-2 and not Ptch will be able to transduce the Dhh signal. These results suggest that Ptch-2 is a Dhh receptor.

Ptch-2 mRNA levels in Smo-M2 transgenic mice [A Smo mutation which results in autonomous phenotypes similar to BCC, Xie et al., *Nature* 391: 90-92 (1998)] can be increased upon abnormal activation of the Hh signaling pathway. As indicated in FIG. 9, patch-2 levers were high in tumor cells (although lower than Ptch levels). This suggests that antibodies directed toward Ptch-2 may be useful in the treatments of BCC.

5. Immunoprecipitation with Smo:

The binding of Ptch-2 to Smo was assessed by cotransfection using a transient transfection system of a myc-epitope tagged Smo and a FLAG-epitope tagged Ptch or Ptch2 expression construct in 293 cells using standard techniques (Gorman, C., *DNA Cloning: A Practical Approach*, Clover, D M ed., Vol. 11, pp. 143-190, IRL Press, Washington, D.C.). 36 hours after transfection, the cells were lysed in 1% NP-40 and immunoprecipitated overnight with the 9EI0 anti-myc antibody or with the M2 anti-FLAG antibody (IBI-Kodak) followed by protein A Sepharose, and then separated on a denatured 6% polyacrylamide gel. Proteins were detected by transfer to nitrocellulose and probing with antibodies to Flag or Myc epitopes, using the ECL detection system (Amersham). FIG. 7B indicates that both Ptch and Ptch-2 are expressed at the same level (IP Flag, Blot Flag) and that like Ptch, Ptch-2 forms a physical complex with Smo. These results suggest that like patched, patched-2 controls Hh signaling through its interaction with Smo.

6. Hh Binding:

To determine whether Ptch-2 is able to bind to the various hedgehog ligands, 293 cells were transfected with Ptch or Ptch-2 using standard procedures. Cells were incubated with 100 pM $^{125}$I-Shh (19 kD amino terminal fragment of murine Shh) in the presence or absence of excess unlabeled Shh or Dhh for 2 h at room temperature. After equilibrium was reached, the ligand bound cells were centrifuged through a continuous sucrose gradient to separate unincorporated and then counted in a scintillation counter. FIG. 7A shows that both Dhh and Shh bind to Ptch and Ptch-2. Varying concentrations of cold competitor indicate that the 2 ligands have similar affinity for Ptch and Ptch-2.

Example 2

Expression of Patched-2 in *E. coli*

The DNA sequence encoding human patched-2 is initially amplified using selected PCR primers. The primers should contain restriction enzyme sites that correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences that encode for an antibiotic resistance gene, a trp promoter, a polyhis leader (including the first six STII codons, polyhis sequence, and enterokinase cleavage site), the vertebrate patched-2 coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized vertebrate patched-2 protein can then be purified using a metal chelating column under conditions that allow tight binding of the protein.

Example 3

Expression of Patched-2 in Mammalian Cells

The vector, pRK5 (see EP 307,247, published Mar. 15, 1989), is employed as the expression vector. Optionally, the vertebrate patched-2 DNA is ligated into pRK5 with selected restriction enzymes to allow insertion of the vertebrate patched-2 DNA using ligation methods such as described in Sambrook et al., supra. The resulting vector is called pRK5-patched-2.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-patched-2 DNA is mixed with about 1 µg DNA encoding the VA RNA gene [Thimmappaya et al., *Cell,* 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of vertebrate patched-2 polypeptide. The cultures containing transfected cells may undergo further incubation (in serum free medium) and the medium is tested in selected bioassays.

In an alternative technique, vertebrate patched-2 may be introduced into 293 cells transiently using the dextran sulfate method described by Somparyrac et al., *Proc. Natl. Acad. Sci.,* 12:7575 (1981). 293 cells are grown to maximal density in a spinner flask and 700 µg pRK5-patched-2 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed vertebrate patched-2 can then be concentrated and purified by any selected method, such as dialysis and/or column chromatography.

In another embodiment, vertebrate patched-2 can be expressed in CHO cells. The pSVi-patched-2 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of vertebrate patched-2 polypeptide, the culture medium may be replaced with serum free medium. Preferably, the cultures are incubated for about 6 days, and then the conditioned medium is harvested. The medium containing the expressed vertebrate patched-2 can then be concentrated and purified by any selected method.

Epitope-tagged vertebrate patched-2 may also be expressed in host CHO cells. The vertebrate patched-2 may be subcloned out of the pRK5 vector. The subclone insert can undergo PCR to fuse in frame with a selected epitope tag such as a poly-his tag into an expression vector. The poly-his tagged vertebrate patched-2 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged vertebrate patched-2 can then be concentrated and purified by any selected method, such as by $Ni^{2+}$-chelate affinity chromatography.

Example 4

Expression of Vertebrate Patched-2 in Yeast

The following method describes recombinant expression of vertebrate patched-2 in yeast.

First, yeast expression vectors are constructed for intracellular production or secretion of vertebrate patched-2 from the ADH2/GAPDH promoter. DNA encoding vertebrate patched-2, a selected signal peptide and the promoter is inserted into suitable restriction enzyme sites in the selected plasmid to direct intracellular expression of vertebrate patched-2. For secretion, DNA encoding vertebrate patched-2 can be cloned into the selected plasmid, together with DNA encoding the ADH2/GAPDH promoter, the yeast alpha-factor secretory signal leader sequence, and linker sequences (if needed) for expression of vertebrate patched-2.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant vertebrate patched-2 can subsequently be isolated and purified by removing the yeast cells from the fermentation medium by centrifugation and then concentrating the medium using selected cartridge filters. The concentrate containing vertebrate patched-2 may further be purified using selected column chromatography resins.

Example 5

Expression of Vertebrate Patched-2 in Baculovirus-Infected Insect Cells

The following method describes recombinant expression of vertebrate patched-2 in Baculovirus-infected insect cells.

The vertebrate patched-2 is patched-2 upstream of an epitope tag contained within a baculovirus expression vector. Such epitope tags include poly-his tags and immunoglobulin tags (like Fe regions of IgG). A variety of plasmids may be employed, including plasmids derived from commercially available plasmids such as pVL1393 (Novagen). Briefly, the vertebrate patched-2 or the desired portion of the vertebrate patched-2 (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged vertebrate patched-2 can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KC1), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged vertebrate patched-2 are pooled and dialyzed against loading buffer.

Alternatively, purification of the IgG tagged (or Fc tagged) vertebrate patched-2 can be performed using known chromatography techniques, including for instance, Protein A or protein G column chromatography.

Example 6

Preparation of Antibodies that Bind Vertebrate patched-2

This example illustrates preparation of monoclonal antibodies, which can specifically bind vertebrate patched-2.

Techniques for producing the monoclonal antibodies are known in the art and are described, for instance, in Goding, supra. Immunogens that may be employed include purified vertebrate patched-2, fusion proteins containing vertebrate patched-2, and cells expressing recombinant vertebrate patched-2 on the cell surface. Selection of the immunogen can be made by the skilled artisan without undue experimentation.

Mice, such as Balb/c, are immunized with the vertebrate patched-2 immunogen (E.g., extracellular portions or cells expressed Ptch-2) emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect vertebrate patched-2 antibodies.

After a suitable antibody titer has been detected, the animals "positive" for antibodies can be injected with a final intravenous injection of vertebrate patched-2. Three to four days later, the mice are sacrificed and the spleen cells are harvested. The spleen cells are then patched-2 (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-patched-2 cells, myeloma hybrids, and spleen cell hybrids.

The hybridoma cells will be screened in an ELISA for reactivity against vertebrate patched-2. Determination of "positive" hybridoma cells secreting the desired monoclonal antibodies against vertebrate patched-2 is within the skill in the art.

The positive hybridoma cells can be injected intraperitoneally into syngeneic Balb/c mice to produce ascites containing the anti-vertebrate patched-2 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 7

Gli Luciferase Assay

The following assay may be used to measure the activation of the transcription factor GLI, the mammalian homologue of the *Drosophila cubitus interruptus* (Ci). It has been shown that GLI is a transcription factor activated upon SHh stimulation of cells.

Nine (9) copies of a GLI binding site present in the HNF3□ enhancer, (Sasaki et al., *Development* 124: 1313-1322 (1997)), are introduced in front of a thymidine kinase minimal promoter driving the luciferase reporter gene in the pGL3 plasmid (Promega). The sequence of the GLI binding sequence is: TCGACAAGCAGGGAACACCCAAGTA-GAAGCTC (p9XGliLuc) (SEQ ID NO:31), while the negative control sequence is: TCGACAAGCAGG GAAGTGGGAAGTAGAAGCTC (p9XmGliLuc) (SEQ ID NO:32). These constructs are cotransfected with the full length Ptch-2 and Smo in C3H10T1/2 cells grown in F12, DMEM (50:50), 10% FCS heat inactivated. The day before transfection $1\times10^5$ cells per well was inoculated in 6 well plates, in 2 ml of media. The following day, 1 μg of each construct is cotransfected in duplicate with 0.025 mg ptkRenilla luciferase plasmid using lipofectamine (Gibco-BRL) in 100 μl OptiMem (with GlutaMAX) as per manufacturer's instructions for 3 hours at 37° C. Serum (20%, 1 ml) is then added to each well and the cells were incubated for 3 more hours at 37° C. Cells are then washed twice with PBS, then incubated for 48 hours at 37° C. in 2 ml of media. Each well is then washed with PBS, and the cells lysed in 0.5 ml Passive Lysis Buffer (Promega) for 15 min. at room temperature on a shaker. The lysate is transferred in eppendorf tubes on ice, spun in a refrigerated centrifuge for 30 seconds and the supernatant saved on ice. For each measure, 20 μl of cell lysate is added to 100 μl of LARII (luciferase assay reagent, Promega) in a polypropylene tube and the luciferase light activity measured. The reaction is stopped by the addition of Stop and Glow buffer (Promega), mixed by pipetting up and down 3 to 5 times and *Renilla* luciferase lights activity is measured on the luminometer.

Deposit of Material

The following materials have been deposited with the American Type Culture Collection, 12301 Parklawn Drive, Rockville, Md., USA (ATCC):

| Designation: | ATCC Dep. No. | Deposit Date |
|---|---|---|
| pRK7.hptc2.Flag-1405 | 209778 | Apr. 14, 1998 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A method of screening for antagonists or agonists of patched-2 biological activity comprising:
   (a) exposing target cells expressing a human patched-2 polypeptide having the amino acid sequence of SEQ ID NO:2 in culture to a candidate compound and Desert Hedgehog (Dhh) wherein said target cells are recombinant cells comprising a heterologous nucleic acid expressing said human patched-2 polypeptide; and
      (i) analyzing the cells for binding of Dhh to patched-2; or
      (ii) scoring phenotypic or functional changes in the treated cells; and
   comparing the results to control cells which were not exposed to the candidate compound, wherein either:
      (1) a decrease in binding of Dhh to patched-2 indicates that the candidate compound is an antagonist of patched-2 biological activity, and wherein an increase in binding of Dhh to patched-2 indicates that the candidate compound is an agonist of patched-2 biological activity; or
      (2) wherein a phenotypic or functional change in the treated cells compared to control cells indicates that the candidate compound is an antagonist or agonist of patched-2 biological activity.

2. The method of claim 1 wherein said recombinant cells are eukaryotic cells.

3. The method of claim 2, wherein said eukaryotic cells are vertebrate cells.

4. The method of claim 3, wherein said vertebrate cells are mammalian cells.

5. The method of claim 2, wherein said eukaryotic cells are insect cells.

6. An in vitro method of screening for an antagonist or an agonist of patched-2 biological activity comprising:
   (a) exposing a patched-2 ligand and a patched-2 polypeptide having the amino acid sequence of SEQ ID NO:2 and having patched-2 biological activity to a candidate compound; and
   (b) analyzing the binding of the patched-2 ligand to the patched-2 polypeptide in the presence of the candidate compound; and comparing the results to a control reaction which was not exposed to the candidate compound, wherein a decrease in binding of the patched-2 ligand to the patched-2 polypeptide indicates that the candidate compound is an antagonist of patched-2 biological activity, and wherein an increase in binding of the patched-2 ligand to the patched-2 polypeptide indicates that the candidate compound is an agonist of patched-2 biological activity.

7. The method of claim 6 wherein said patched-2 polypeptide is an epitope-tagged patched-2.

8. The method of claim 7 wherein said epitope-tagged patched-2 comprises a polypeptide selected from the group consisting of poly-histidine, poly-histidine-glycine, flu hemagglutinin, c-myc, Herpes Simplex virus glycoprotein D, Flag-peptide, KT3 epitope peptide, α-tubulin epitope peptide, and T7 gene 10 protein.

9. The method of claim 6 wherein said patched-2 ligand is added after said candidate compound.

10. The method of claim 6 wherein said candidate compound is added after said patched-2 ligand.

11. The method of claim 6 wherein said candidate compound and said patched-2 ligand are added simultaneously.

12. An in vitro method of screening for an antagonist or an agonist of patched-2 biological activity comprising: (a) exposing a patched-2 ligand and a patched-2 immunoadhesin, to a candidate compound, wherein said patched-2 immunoadhesin comprises a polypeptide comprising the amino acid sequence of SEQ ID NO:2; and
   (b) analyzing the binding of the patched-2 ligand to the patched-2 immunoadhesin in the presence of the candidate compound; and comparing the results to a control reaction which was not exposed to the candidate compound, wherein a decrease in binding of the patched-2 ligand to the patched-2 immunoadhesin indicates that the candidate compound is an antagonist of patched-2 biological activity, and wherein an increase in binding of the patched-2 ligand to the patched-2 immunoadhesin indicates that the candidate compound is an agonist of patched-2 biological activity.

13. The method of claim 12 wherein said immunoadhesin is attached to a solid phase.

\* \* \* \* \*

SEQUENCE LISTING

```
<160> NUMBER OF SEQ ID NOS: 35

<210> SEQ ID NO 1
<211> LENGTH: 4030
<212> TYPE: DNA
<213> ORGANISM: Homo sapiens

<400> SEQUENCE: 1
gttatttcag gccatggtgt tgcgccgaat taattcccga tccagacatg ataagataca      60
ttgatgagtt tggacaaacc acaactagaa tgcagtgaaa aaaatgcttt atttgtgaaa     120
tttgtgatgc tattgcttta tttgtaacca ttataagctg caataaacaa gttgggccat     180
ggcggccaag cttctgcagg tcgactctag aggatccccg gggaattccg gcatgactcg     240
```

```
atcgccgccc ctcagagagc tgcccccgag ttacacaccc ccagctcgaa ccgcagcacc      300
ccagatccta gctgggagcc tgaaggctcc actctggctt cgtgcttact tccagggcct      360
gctcttctct ctgggatgcg ggatccgag acattgtggc aaagtgctct ttctgggact       420
gttggccttt ggggccctgg cattaggtct ccgcatggcc attattgaga caaacttgga      480
acagctctgg gtagaagtgg gcagccgggt gagccaggag ctgcattaca ccaaggagaa      540
gctgggggag gaggctgcat acacctctca gatgctgata cagaccgcac gccaggaggg      600
agagaacatc ctcacacccg aagcacttgg cctccacctc caggcagccc tcactgccag      660
taaagtccaa gtatcactct atgggaagtc ctgggatttg aacaaaatct gctacaagtc      720
aggagttccc cttattgaaa atggaatgat tgagtggatg attgagaagc tgtttccgtg      780
cgtgatcctc acccccctcg actgcttctg ggagggagcc aaactccaag ggggctccgc      840
ctacctgccc ggccgcccgg atatccagtg gaccaacctg gatccagagc agctgctgga      900
ggagctgggt ccctttgcct cccttgaggg cttccgggag ctgctagaca aggcacaggt      960
gggccaggcc tacgtggggc ggccctgtct gcaccctgat gacctccact gcccacctag     1020
tgcccccaac catcacagca ggcaggctcc caatgtggct cacagctga gtgggggctg      1080 ccatggcttc tcccacaaat tcatgcactg gcaggaggaa ttgctgctgg gaggcatggc     1140
cagagacccc caaggagagc tgctgagggc agaggccctg cagagcacct tcttgctgat     1200
gagtccccgc cagctgtacg agcatttccg gggtgactat cagacacatg acattggctg     1260
gagtgaggag caggccagca cagtgctaca agcctggcag cggcgctttg tgcagctggc     1320
ccaggaggcc ctgcctgaga acgcttccca gcagatccat gccttctcct ccaccaccct     1380
ggatgacatc ctgcatgcgt tctctgaagt cagtgctgcc cgtgtggtgg aggctatct      1440 gctcatgctg gcctatgcct gtgtgaccat gctgcggtgg gactgcgccc agtcccaggg     1500
ttccgtgggc cttgccgggg tactgctggt ggccctggcg gtggcctcag gccttgggct     1560
ctgtgccctg ctcggcatca ccttcaatgc tgccactacc caggtgctgc ctttcttggc     1620
tctgggaatc ggcgtggatg acgtattcct gctggcgcat gccttcacag aggctctgcc     1680 tggcaccct ctccaggagc gcatgggcga gtgtctgcag cgcacgggca ccagtgtcgt      1740
actcacatcc atcaacaaca tggccgcctt cctcatggct gccctcgttc catccctgc     1800 gctgcgagcc ttctccctac aggcggccat agtggttggc tgcacctttg tagccgtgat     1860
gcttgtcttc ccagccatcc tcagcctgga cctacggcgg cgccactgcc agcgccttga     1920
tgtgctctgc tgcttctcca gtccctgctc tgctcaggtg attcagatcc tgccccagga     1980
gctgggggac gggacagtac cagtgggcat gcccacctc actgccacag ttcaagcctt      2040
tacccactgt gaagccagca gccagcatgt ggtcaccatc ctgcctcccc aagcccacct     2100
ggtgccccca ccttctgacc cactgggctc tgagctcttc agccctggag gtccacacg     2160 ggaccttcta ggccaggagg aggagacaag gcagaaggca gcctgcaagt ccctgccctg     2220
tgcccgctgg aatcttgccc atttcgcccg ctatcagttt gccccgttgc tgctccagtc     2280
acatgccaag gccatcgtgc tggtgctctt tggtgctctt ctgggcctga gcctctacgg     2340
agccaccttg gtgcaagacg gcctggccct gacggatgtg gtgcctcggg gcaccaagga     2400
gcatgccttc ctgagcgccc agctcaggta cttctccctg tacgaggtgg ccctggtgac     2460
ccagggtggc tttgactacg cccattccca acgcgccctc tttgatctgc accagcgctt     2520
cagttccctc aaggcggtgc tgcccccacc ggccacccag gcaccccgca cctggctgca     2580
ctattaccgc aactggctac agggaatcca ggctgccttt gaccaggact gggcttctgg     2640
```

```
gcgcatcacc cgccactcgt accgcaatgg ctctgaggat ggggccctgg cctacaagct    2700
gctcatccag actggagacg cccaggagcc tctggatttc agccagctga ccacaaggaa    2760
gctggtggac agagagggac tgattccacc cgagctcttc tacatggggc tgaccgtgtg    2820
ggtgagcagt gacccctgg gtctggcagc ctcacaggcc aacttctacc ccccacctcc    2880
tgaatggctg cacgacaaat acgacaccac ggggagaac cttcgcatcc cgccagctca    2940
gcccttggag tttgcccagt tccccttcct gctgcgtggc ctccagaaga ctgcagactt    3000
tgtggaggcc atcgagggg cccgggcagc atgcgcagag gccggccagg ctggggtgca    3060
cgcctacccc agcggctccc ccttcctctt ctgggaacag tatctgggcc tgcggcgctg    3120
cttcctgctg gccgtctgca tcctgctggt gtgcactttc ctcgtctgtg ctctgctgct    3180
cctcaacccc tggacggctg gcctcatagt gctggtcctg gcgatgatga cagtggaact    3240
ctttggtatc atgggtttcc tgggcatcaa gctgagtgcc atcccgtgg tgatccttgt    3300 ggcctctgta ggcattggcg ttgagttcac agtccacgtg gctctgggct tcctgaccac    3360
ccagggcagc cggaacctgc gggccgccca tgcccttgag cacacatttg ccccgtgac    3420 cgatggggcc atctccacat tgctgggtct gctcatgctt gctggttccc actttgactt    3480
cattgtaagg tacttctttg cggcgctgac agtgctcacg ctcctgggcc tcctccatgg    3540
actcgtgctg ctgcctgtgc tgctgtccat cctgggcccg ccgccagagg tgatacagat    3600
gtacaaggaa agcccagaga tcctgagtcc accagctcca cagggaggcg ggcttaggtg    3660
gggggcatcc tcctccctgc cccagagctt tgccagagtg actacctcca tgaccgtggc    3720
catccaccca cccccccctgc ctggtgccta catccatcca gcccctgatg agccccttg    3780 gtcccctgct gccactagct ctggcaacct cagttccagg ggaccaggtc agccactgg    3840 gtgaaagagc agctgaagca cagagaccat gtgtggggcg tgtggggtca ctgggaagca    3900
ctgggtctgg tgttagacgc aggacggacc cctggagggc cctgctgctg ctgcatcccc    3960
tctcccgacc cagctgtcat gggcctccct gatatcgaat tcaatcgata gaaccgaggt    4020
gcagttggac                                                          4030
```

<210> SEQ ID NO 2
<211> LENGTH: 1203
<212> TYPE: PRT
<213> ORGANISM: Homo sapiens

<400> SEQUENCE: 2

```
Met Thr Arg Ser Pro Leu Arg Glu Leu Pro Ser Tyr Thr Pro
1               5                   10                  15
Pro

Pro Ala Arg Thr Ala Ala Pro Gln Ile Leu Ala Gly Ser Leu Lys Ala
            20                  25                  30

Pro Leu Trp Leu Arg Ala Tyr Phe Gln Gly Leu Leu Phe Ser Leu Gly
        35                  40                  45

Cys Gly Ile Gln Arg His Cys Gly Lys Val Leu Phe Leu Gly Leu Leu
    50                  55                  60

Ala Phe Gly Ala Leu Ala Leu Gly Leu Arg Met Ala Ile Ile Glu Thr
65                  70                  75                  80

Asn Leu Glu Gln Leu Trp Val Glu Val Gly Ser Arg Val Ser Gln Glu
                85                  90                  95

Leu His Tyr Thr Lys Glu Lys Leu Gly Glu Glu Ala Ala Tyr Thr Ser
            100                 105                 110

Gln Met Leu Ile Gln Thr Ala Arg Gln Glu Gly Glu Asn Ile Leu Thr
```

-continued

```
            115                 120                 125
Pro Glu Ala Leu Gly Leu His Leu Gln Ala Ala Leu Thr Ala Ser Lys
        130                 135                 140
Val Gln Val Ser Leu Tyr Gly Lys Ser Trp Asp Leu Asn Lys Ile Cys
145                 150                 155                 160
Tyr Lys Ser Gly Val Pro Leu Ile Glu Asn Gly Met Ile Glu Trp Met
                165                 170                 175
Ile Glu Lys Leu Phe Pro Cys Val Ile Leu Thr Pro Leu Asp Cys Phe
            180                 185                 190
Trp Glu Gly Ala Lys Leu Gln Gly Gly Ser Ala Tyr Leu Pro Gly Arg
        195                 200                 205
Pro Asp Ile Gln Trp Thr Asn Leu Asp Pro Glu Gln Leu Leu Glu Glu
    210                 215                 220
Leu Gly Pro Phe Ala Ser Leu Glu Gly Phe Arg Glu Leu Leu Asp Lys
225                 230                 235                 240
Ala Gln Val Gly Gln Ala Tyr Val Gly Arg Pro Cys Leu His Pro Asp
                245                 250                 255
Asp Leu His Cys Pro Pro Ser Ala Pro Asn His His Ser Arg Gln Ala
            260                 265                 270
Pro Asn Val Ala His Glu Leu Ser Gly Gly Cys His Gly Phe Ser His
        275                 280                 285
Lys Phe Met His Trp Gln Glu Glu Leu Leu Leu Gly Gly Met Ala Arg
    290                 295                 300
Asp Pro Gln Gly Glu Leu Leu Arg Ala Glu Ala Leu Gln Ser Thr Phe
305                 310                 315                 320
Leu Leu Met Ser Pro Arg Gln Leu Tyr Glu His Phe Arg Gly Asp Tyr
                325                 330                 335
Gln Thr His Asp Ile Gly Trp Ser Glu Glu Gln Ala Ser Thr Val Leu
            340                 345                 350
Gln Ala Trp Gln Arg Arg Phe Val Gln Leu Ala Gln Glu Ala Leu Pro
        355                 360                 365
Glu Asn Ala Ser Gln Gln Ile His Ala Phe Ser Ser Thr Thr Leu Asp
    370                 375                 380
Asp Ile Leu His Ala Phe Ser Glu Val Ser Ala Ala Arg Val Val Gly
385                 390                 395                 400
Gly Tyr Leu Leu Met Leu Ala Tyr Ala Cys Val Thr Met Leu Arg Trp
                405                 410                 415
Asp Cys Ala Gln Ser Gly Ser Val Gly Leu Ala Gly Val Leu Leu
            420                 425                 430
Val Ala Leu Ala Val Ala Ser Gly Leu Gly Leu Cys Ala Leu Leu Gly
        435                 440                 445
Ile Thr Phe Asn Ala Ala Thr Thr Gln Val Leu Pro Phe Leu Ala Leu
    450                 455                 460
Gly Ile Gly Val Asp Asp Val Phe Leu Leu Ala His Ala Phe Thr Glu
465                 470                 475                 480
Ala Leu Pro Gly Thr Pro Leu Gln Glu Arg Met Gly Glu Cys Leu Gln
                485                 490                 495
Arg Thr Gly Thr Ser Val Val Leu Thr Ser Ile Asn Asn Met Ala Ala
            500                 505                 510
Phe Leu Met Ala Ala Leu Val Pro Ile Pro Ala Leu Arg Ala Phe Ser
        515                 520                 525
Leu Gln Ala Ala Ile Val Val Gly Cys Thr Phe Val Ala Val Met Leu
    530                 535                 540
```

```
Val Phe Pro Ala Ile Leu Ser Leu Asp Leu Arg Arg His Cys Gln
545                 550                 555                 560

Arg Leu Asp Val Leu Cys Cys Phe Ser Pro Cys Ser Ala Gln Val
                565                 570                 575

Ile Gln Ile Leu Pro Gln Glu Leu Gly Asp Gly Thr Val Pro Val Gly
            580                 585                 590

Ile Ala His Leu Thr Ala Thr Val Gln Ala Phe Thr His Cys Glu Ala
        595                 600                 605

Ser Ser Gln His Val Val Thr Ile Leu Pro Pro Gln Ala His Leu Val
    610                 615                 620

Pro Pro Pro Ser Asp Pro Leu Gly Ser Glu Leu Phe Ser Pro Gly Gly
625                 630                 635                 640

Ser Thr Arg Asp Leu Leu Gly Gln Glu Glu Thr Arg Gln Lys Ala
                645                 650                 655

Ala Cys Lys Ser Leu Pro Cys Ala Arg Trp Asn Leu Ala His Phe Ala
            660                 665                 670

Arg Tyr Gln Phe Ala Pro Leu Leu Gln Ser His Ala Lys Ala Ile
    675                 680                 685

Val Leu Val Leu Phe Gly Ala Leu Leu Gly Leu Ser Leu Tyr Gly Ala
690                 695                 700

Thr Leu Val Gln Asp Gly Leu Ala Leu Thr Asp Val Val Pro Arg Gly
705                 710                 715                 720

Thr Lys Glu His Ala Phe Leu Ser Ala Gln Leu Arg Tyr Phe Ser Leu
            725                 730                 735

Tyr Glu Val Ala Leu Val Thr Gln Gly Gly Phe Asp Tyr Ala His Ser
        740                 745                 750

Gln Arg Ala Leu Phe Asp Leu His Gln Arg Phe Ser Ser Leu Lys Ala
    755                 760                 765

Val Leu Pro Pro Ala Thr Gln Ala Pro Arg Thr Trp Leu His Tyr
770                 775                 780

Tyr Arg Asn Trp Leu Gln Gly Ile Gln Ala Ala Phe Asp Gln Asp Trp
785                 790                 795                 800

Ala Ser Gly Arg Ile Thr Arg His Ser Tyr Arg Asn Gly Ser Glu Asp
            805                 810                 815

Gly Ala Leu Ala Tyr Lys Leu Leu Ile Gln Thr Gly Asp Ala Gln Glu
        820                 825                 830

Pro Leu Asp Phe Ser Gln Leu Thr Thr Arg Lys Leu Val Asp Arg Glu
    835                 840                 845

Gly Leu Ile Pro Pro Glu Leu Phe Tyr Met Gly Leu Thr Val Trp Val
850                 855                 860

Ser Ser Asp Pro Leu Gly Leu Ala Ala Ser Gln Ala Asn Phe Tyr Pro
865                 870                 875                 880

Pro Pro Pro Glu Trp Leu His Asp Lys Tyr Asp Thr Thr Gly Glu Asn
            885                 890                 895

Leu Arg Ile Pro Pro Ala Gln Pro Leu Glu Phe Ala Gln Phe Pro Phe
        900                 905                 910

Leu Leu Arg Gly Leu Gln Lys Thr Ala Asp Phe Val Glu Ala Ile Glu
    915                 920                 925

Gly Ala Arg Ala Ala Cys Ala Glu Ala Gly Gln Gly Val His Ala
930                 935                 940

Tyr Pro Ser Gly Ser Pro Phe Leu Phe Trp Glu Gln Tyr Leu Gly Leu
945                 950                 955                 960
```

-continued

```
Arg Arg Cys Phe Leu Leu Ala Val Cys Ile Leu Val Cys Thr Phe
            965                 970                 975

Leu Val Cys Ala Leu Leu Leu Asn Pro Trp Thr Ala Gly Leu Ile
            980                 985                 990

Val Leu Val Leu Ala Met Met Thr Val Glu Leu Phe Gly Ile Met Gly
            995                 1000                1005

Phe Leu Gly Ile Lys Leu Ser Ala Ile Pro Val Val Ile Leu Val
            1010                1015                1020

Ala Ser Val Gly Ile Gly Val Glu Phe Thr Val His Val Ala Leu
            1025                1030                1035

Gly Phe Leu Thr Thr Gln Gly Ser Arg Asn Leu Arg Ala Ala His
            1040                1045                1050

Ala Leu Glu His Thr Phe Ala Pro Val Thr Asp Gly Ala Ile Ser
            1055                1060                1065

Thr Leu Leu Gly Leu Leu Met Leu Ala Gly Ser His Phe Asp Phe
            1070                1075                1080

Ile Val Arg Tyr Phe Phe Ala Ala Leu Thr Val Leu Thr Leu Leu
            1085                1090                1095

Gly Leu Leu His Gly Leu Val Leu Leu Pro Val Leu Leu Ser Ile
            1100                1105                1110

Leu Gly Pro Pro Pro Glu Val Ile Gln Met Tyr Lys Glu Ser Pro
            1115                1120                1125

Glu Ile Leu Ser Pro Pro Ala Pro Gln Gly Gly Gly Leu Arg Trp
            1130                1135                1140

Gly Ala Ser Ser Ser Leu Pro Gln Ser Phe Ala Arg Val Thr Thr
            1145                1150                1155

Ser Met Thr Val Ala Ile His Pro Pro Pro Leu Pro Gly Ala Tyr
            1160                1165                1170

Ile His Pro Ala Pro Asp Glu Pro Pro Trp Ser Pro Ala Ala Thr
            1175                1180                1185

Ser Ser Gly Asn Leu Ser Ser Arg Gly Pro Gly Pro Ala Thr Gly
            1190                1195                1200
```

```
<210> SEQ ID NO 3
<211> LENGTH: 228
<212> TYPE: DNA
<213> ORGANISM: Homo sapiens
<220> FEATURE:
<221> NAME/KEY: Unsure
<222> LOCATION: (20)..(20)
<223> OTHER INFORMATION: unknown base
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: Unsure
<222> LOCATION: (27)..(27)
<223> OTHER INFORMATION: unknown base
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: Unsure
<222> LOCATION: (135)..(135)
<223> OTHER INFORMATION: unknown base
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: Unsure
```

```
<222> LOCATION: (156)..(156)
<223> OTHER INFORMATION: unknown base
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: Unsure
<222> LOCATION: (210)..(210)
<223> OTHER INFORMATION: unknown base
<220> FEATURE:
<221> NAME/KEY: misc_feature
<222> LOCATION: (210)..(210)
<223> OTHER INFORMATION: n is a, c, g, or t

<400> SEQUENCE: 3
gctggggtgc acgcctaccn cagcggntcc cccttcctct tctgggaaca gtatctgggc      60
ctgcggcgct gcttcctgct ggccgtctgc atcctgctgg tgtgcacttt cctcgtctgt     120
gctctgctgc tcctnaaccc ctggacggct ggcctnatag tgctggtcct ggcgatgatg     180
acagtggaac tctttggtat catgggtttn ctgggcatca agctgagt                 228

<210> SEQ ID NO 4
<211> LENGTH: 76
<212> TYPE: PRT
<213> ORGANISM: Homo sapiens

<400> SEQUENCE: 4

Leu Gly Leu Ser Ser Tyr Pro Asn Gly Tyr Pro Phe Leu Phe Trp Glu
1               5                   10                  15

Gln Tyr Ile Gly Leu Arg His Trp Leu Leu Leu Phe Ile Ser Val Val
            20                  25                  30

Leu Ala Cys Thr Phe Leu Val Cys Ala Val Phe Leu Leu Asn Pro Trp
        35                  40                  45

Thr Ala Gly Ile Ile Val Met Val Leu Ala Leu Met Thr Val Glu Leu
    50                  55                  60

Phe Gly Met Met Gly Leu Ile Gly Ile Lys Leu Ser
65                  70                  75

<210> SEQ ID NO 5
<211> LENGTH: 125
<212> TYPE: DNA
<213> ORGANISM: Homo sapiens
<220> FEATURE:
<221> NAME/KEY: unsure
<222> LOCATION: (115)..(115)
<223> OTHER INFORMATION: unknown base
<220> FEATURE:
<221> NAME/KEY: misc_feature
<222> LOCATION: (115)..(115)
<223> OTHER INFORMATION: n is a, c, g, or t

<400> SEQUENCE: 5
gctggggtgc acgcctaccc cagcggctcc cccttcctct tctgggaaca gtatctgggc      60
ctgcggcgct gcttcctgct ggccgtctgc atcctgctgg tgtgcacttt cctcntctgt     120
gctct                                                                125

<210> SEQ ID NO 6
<211> LENGTH: 50
<212> TYPE: DNA
<213> ORGANISM: Homo sapiens
<220> FEATURE:
<221> NAME/KEY: unsure
<222> LOCATION: (13)..(13)
<223> OTHER INFORMATION: unknown base
```

```
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: unsure
<222> LOCATION: (14)..(14)
<223> OTHER INFORMATION: unknown base

<400> SEQUENCE: 6
ccgggcggca tgnngcgaag cggaccacgc tgggggtgg ctcaggggag            50

<210> SEQ ID NO 7
<211> LENGTH: 1182
<212> TYPE: PRT
<213> ORGANISM: Mus musculus

<400> SEQUENCE: 7
```

| | | | | | | | | | | | | | | |
|---|---|---|---|---|---|---|---|---|---|---|---|---|---|---|
| Met | Val | Arg | Pro | Leu | Ser | Leu | Gly | Glu | Leu | Pro | Pro | Ser | Tyr | Thr | Pro |
| 1 | | | | 5 | | | | | 10 | | | | | 15 | |
| Pro | Ala | Arg | Ser | Ser | Ala | Pro | His | Ile | Leu | Ala | Gly | Ser | Leu | Gln | Ala |
| | | | 20 | | | | | 25 | | | | | 30 | | |
| Pro | Leu | Trp | Leu | Arg | Ala | Tyr | Phe | Gln | Gly | Leu | Leu | Phe | Ser | Leu | Gly |
| | | | 35 | | | | | 40 | | | | | 45 | | |
| Cys | Arg | Ile | Gln | Lys | His | Cys | Gly | Lys | Val | Leu | Phe | Leu | Gly | Leu | Val |
| 50 | | | | | 55 | | | | | 60 | | | | | |
| Ala | Phe | Gly | Ala | Leu | Ala | Leu | Gly | Leu | Arg | Val | Ala | Val | Ile | Glu | Thr |
| 65 | | | | | 70 | | | | | 75 | | | | | 80 |
| Asp | Leu | Glu | Gln | Leu | Trp | Val | Glu | Val | Gly | Ser | Arg | Val | Ser | Gln | Glu |
| | | | | 85 | | | | | 90 | | | | | 95 | |
| Leu | His | Tyr | Thr | Lys | Glu | Lys | Leu | Gly | Glu | Glu | Ala | Ala | Tyr | Thr | Ser |
| | | | 100 | | | | | 105 | | | | | 110 | | |
| Gln | Met | Leu | Ile | Gln | Thr | Ala | His | Gln | Glu | Gly | Gly | Asn | Val | Leu | Thr |
| | | | 115 | | | | | 120 | | | | | 125 | | |
| Pro | Glu | Ala | Leu | Asp | Leu | His | Leu | Gln | Ala | Ala | Leu | Thr | Ala | Ser | Lys |
| 130 | | | | | 135 | | | | | 140 | | | | | |
| Val | Gln | Val | Ser | Leu | Tyr | Gly | Lys | Ser | Trp | Asp | Leu | Asn | Lys | Ile | Cys |
| 145 | | | | | 150 | | | | | 155 | | | | | 160 |
| Tyr | Lys | Ser | Gly | Val | Pro | Leu | Ile | Glu | Asn | Gly | Met | Ile | Glu | Arg | Met |
| | | | | 165 | | | | | 170 | | | | | 175 | |
| Ile | Glu | Lys | Leu | Phe | Pro | Cys | Val | Ile | Leu | Thr | Pro | Leu | Asp | Cys | Phe |
| | | | 180 | | | | | 185 | | | | | 190 | | |
| Trp | Glu | Gly | Ala | Lys | Leu | Gln | Gly | Gly | Ser | Ala | Tyr | Leu | Pro | Gly | Arg |
| | | | 195 | | | | | 200 | | | | | 205 | | |
| Pro | Asp | Ile | Gln | Trp | Thr | Asn | Leu | Asp | Pro | Gln | Gln | Leu | Leu | Glu | Glu |
| 210 | | | | | 215 | | | | | 220 | | | | | |
| Leu | Gly | Pro | Phe | Ala | Ser | Leu | Glu | Gly | Phe | Arg | Glu | Leu | Leu | Asp | Lys |
| 225 | | | | | 230 | | | | | 235 | | | | | 240 |
| Ala | Gln | Val | Gly | Gln | Ala | Tyr | Val | Gly | Arg | Pro | Cys | Leu | Asp | Pro | Asp |
| | | | | 245 | | | | | 250 | | | | | 255 | |
| Asp | Pro | His | Cys | Pro | Pro | Ser | Ala | Pro | Asn | Arg | His | Ser | Arg | Gln | Ala |
| | | | 260 | | | | | 265 | | | | | 270 | | |
| Pro | Asn | Val | Ala | Gln | Glu | Leu | Ser | Gly | Cys | His | Gly | Phe | Ser | His | His |
| | | | 275 | | | | | 280 | | | | | 285 | | |
| Lys | Phe | Met | His | Trp | Gln | Glu | Glu | Leu | Leu | Leu | Gly | Gly | Thr | Ala | Arg |
| 290 | | | | | 295 | | | | | 300 | | | | | |
| Asp | Leu | Gln | Gly | Gln | Leu | Leu | Arg | Ala | Glu | Ala | Leu | Gln | Ser | Thr | Phe |

```
305                 310                 315                 320

Leu Leu Met Ser Pro Arg Gln Leu Tyr Glu His Phe Arg Gly Asp Tyr
                325                 330                 335

Gln Thr His Asp Ile Gly Trp Ser Glu Glu Gln Ala Ser Met Val Leu
                340                 345                 350

Gln Ala Trp Gln Arg Arg Phe Val Gln Leu Ala Gln Glu Ala Leu Pro
                355                 360                 365

Ala Asn Ala Ser Gln Gln Ile His Ala Phe Ser Ser Thr Thr Leu Asp
        370                 375                 380

Asp Ile Leu Arg Ala Phe Ser Glu Val Ser Thr Thr Arg Val Val Gly
385                 390                 395                 400

Gly Tyr Leu Leu Met Leu Ala Tyr Ala Cys Val Thr Met Leu Arg Trp
                405                 410                 415

Asp Cys Ala Gln Ser Gln Gly Ala Val Gly Leu Ala Gly Val Leu Leu
                420                 425                 430

Val Ala Leu Ala Val Ala Ser Gly Leu Gly Leu Cys Ala Leu Leu Gly
                435                 440                 445

Ile Thr Phe Asn Ala Ala Thr Thr Gln Val Leu Pro Phe Leu Ala Leu
        450                 455                 460

Gly Ile Gly Val Asp Asp Ile Phe Leu Leu Ala His Ala Phe Thr Lys
465                 470                 475                 480

Ala Pro Pro Asp Thr Pro Leu Pro Glu Arg Met Gly Glu Cys Leu Arg
                485                 490                 495

Ser Thr Gly Thr Ser Val Ala Leu Thr Ser Val Asn Asn Met Val Ala
                500                 505                 510

Phe Phe Met Ala Ala Leu Val Pro Ile Pro Ala Leu Arg Ala Phe Ser
                515                 520                 525

Leu Gln Ala Ala Ile Val Val Gly Cys Asn Phe Ala Ala Val Met Leu
        530                 535                 540

Val Phe Pro Ala Ile Leu Ser Leu Asp Leu Arg Arg Arg His Arg Gln
545                 550                 555                 560

Arg Leu Asp Val Leu Cys Cys Phe Ser Ser Pro Cys Ser Ala Gln Val
                565                 570                 575

Ile Gln Met Leu Pro Gln Glu Leu Gly Asp Arg Ala Val Pro Val Gly
                580                 585                 590

Ile Ala His Leu Thr Ala Thr Val Gln Ala Phe Thr His Cys Glu Ala
                595                 600                 605

Ser Ser Gln His Val Val Thr Ile Leu Pro Pro Gln Ala His Leu Leu
        610                 615                 620

Ser Pro Ala Ser Asp Pro Leu Gly Ser Glu Leu Tyr Ser Pro Gly Gly
625                 630                 635                 640

Ser Thr Arg Asp Leu Leu Ser Gln Glu Glu Gly Thr Gly Pro Gln Ala
                645                 650                 655

Ala Cys Arg Pro Leu Leu Cys Ala His Trp Thr Leu Ala His Phe Ala
                660                 665                 670

Arg Tyr Gln Phe Ala Pro Leu Leu Leu Gln Thr Arg Ala Lys Ala Leu
                675                 680                 685

Val Leu Leu Phe Phe Gly Ala Leu Leu Gly Leu Ser Leu Tyr Gly Ala
                690                 695                 700

Thr Leu Val Gln Asp Gly Leu Ala Leu Thr Asp Val Val Pro Arg Gly
705                 710                 715                 720

Thr Lys Glu His Ala Phe Leu Ser Ala Gln Leu Arg Tyr Phe Ser Leu
                725                 730                 735
```

```
Tyr Glu Val Ala Leu Val Thr Gln Gly Gly Phe Asp Tyr Ala His Ser
            740                 745                 750

Gln Arg Ala Leu Phe Asp Leu His Gln Arg Phe Ser Ser Leu Lys Ala
            755                 760                 765

Val Leu Pro Pro Pro Ala Thr Gln Ala Pro Arg Thr Trp Leu His Tyr
            770                 775                 780

Tyr Arg Ser Trp Leu Gln Gly Ile Gln Ala Ala Phe Asp Gln Asp Trp
785                 790                 795                 800

Ala Ser Gly Arg Ile Thr Cys His Ser Tyr Arg Asn Gly Ser Glu Asp
                    805                 810                 815

Gly Ala Leu Ala Tyr Lys Leu Leu Ile Gln Thr Gly Asn Ala Gln Glu
                    820                 825                 830

Pro Leu Asp Phe Ser Gln Leu Thr Thr Arg Lys Leu Val Asp Lys Glu
                    835                 840                 845

Gly Leu Ile Pro Pro Glu Leu Phe Tyr Met Gly Leu Thr Val Trp Val
                    850                 855                 860

Ser Ser Asp Pro Leu Gly Leu Ala Ala Ser Gln Ala Asn Phe Tyr Pro
865                 870                 875                 880

Pro Pro Pro Glu Trp Leu His Asp Lys Tyr Asp Thr Thr Gly Glu Asn
                    885                 890                 895

Leu Arg Ile Pro Ala Ala Gln Pro Leu Glu Phe Ala Gln Phe Pro Phe
                    900                 905                 910

Leu Leu His Gly Leu Gln Lys Thr Ala Asp Phe Val Glu Ala Ile Glu
                    915                 920                 925

Gly Ala Arg Ala Ala Cys Thr Glu Ala Gly Gln Ala Gly Val His Ala
            930                 935                 940

Tyr Pro Ser Gly Ser Pro Phe Leu Phe Trp Glu Gln Tyr Leu Gly Leu
945                 950                 955                 960

Arg Arg Cys Phe Leu Leu Ala Val Cys Ile Leu Leu Val Cys Thr Phe
                    965                 970                 975

Leu Val Cys Ala Leu Leu Leu Leu Ser Pro Trp Thr Ala Gly Leu Ile
                    980                 985                 990

Val Leu Val Leu Ala Met Met Thr Val Glu Leu Phe Gly Ile Met Gly
            995                 1000                1005

Phe Leu Gly Ile Lys Leu Ser Ala Ile Pro Val Val Ile Leu Val
        1010                1015                1020

Ala Ser Ile Gly Ile Gly Val Glu Phe Thr Val His Val Ala Leu
        1025                1030                1035

Gly Phe Leu Thr Ser His Gly Ser Arg Asn Leu Arg Ala Ala Ser
        1040                1045                1050

Ala Leu Glu Gln Thr Phe Ala Pro Val Thr Asp Gly Ala Val Ser
        1055                1060                1065

Thr Leu Leu Gly Leu Leu Met Leu Ala Gly Ser Asn Phe Asp Phe
        1070                1075                1080

Ile Ile Arg Tyr Phe Phe Val Val Leu Thr Val Leu Thr Leu Leu
        1085                1090                1095

Gly Leu Leu His Gly Leu Leu Leu Leu Pro Val Leu Leu Ser Ile
        1100                1105                1110

Leu Gly Pro Pro Pro Gln Val Val Gln Val Tyr Lys Glu Ser Pro
        1115                1120                1125

Gln Thr Leu Asn Ser Ala Ala Pro Gln Arg Gly Gly Leu Arg Trp
        1130                1135                1140
```

Asp Arg Pro Pro Thr Leu Pro Gln Ser Phe Ala Arg Val Thr Thr
1145                1150                1155

Ser Met Thr Val Ala Leu His Pro Pro Leu Pro Gly Ala Tyr
1160                1165                1170

Val His Pro Ala Ser Glu Glu Pro Thr
1175                1180

<210> SEQ ID NO 8
<211> LENGTH: 4004
<212> TYPE: DNA
<213> ORGANISM: Homo sapiens

<400> SEQUENCE: 8

| | | | | | |
|---|---|---|---|---|---|
| cccacgcgtc | cgggagaagc | tgggggagga | ggctgcatac | acctctcaga | tgctgataca | 60 |
| gaccgcacgc | caggagggag | agaacatcct | cacacccgaa | gcacttggcc | tccacctcca | 120 |
| ggcagccctc | actgccagta | aagtccaagt | atcactctat | gggaagtcct | gggatttgaa | 180 |
| caaaatctgc | tacaagtcag | gagttcccct | tattgaaaat | ggaatgattg | agcggatgat | 240 |
| tgagaagctg | tttccgtgcg | tgatcctcac | cccctcgac | tgcttctggg | agggagccaa | 300 |
| actccaaggg | ggctccgcct | acctgccgct | cccaatgtgg | ctcacgagct | gagtggggc | 360 |
| tgccatggct | tctcccacaa | attcatgcac | tggcaggagg | aattgctgct | gggaggcatg | 420 |
| gccagagacc | ccaaggaga | gctgctgagg | gcagaggccc | tgcagagcac | cttcttgctg | 480 |
| atgagtcccc | gccagctgta | cgagcatttc | cggggtgact | atcagacaca | tgacattggc | 540 |
| tggagtgagg | agcaggccag | cacagtgcta | caagcctggc | agcggcgctt | tgtgcaggtc | 600 |
| ggtatggaca | aggacagggg | ggtgccctga | ggccattccc | tcctcctgcc | ccctcctatc | 660 |
| caccctgttt | ctccagctgg | cccaggaggc | cctgcctgag | aacgcttccc | agcagatcca | 720 |
| tgccttctcc | tccaccaccc | tggatgacat | cctgcatgcg | ttctctgaag | tcagtgctgc | 780 |
| ccgtgtggtg | ggaggctatc | tgctcatggt | gggtcttgca | cctggcacct | tgccccacc | 840 |
| ccacctccaa | ccagtgccca | ccctggggag | ccctgagac | tgccctttcc | ccccacagct | 900 |
| ggcctatgcc | tgtgtgacca | tgctgcgtgt | ggactgcgcc | cagtcccagg | gttccgtggg | 960 |
| ccttgccggg | gtactgctgg | tggccctggc | ggtggcctca | ggccttgggc | tctgtgccct | 1020 |
| gctcggcatc | accttcaatg | ctgccactac | ccaggtacgc | caggactgca | gggcagactc | 1080 |
| agtgccagtc | accaggcttc | acgggtcctc | agctgcccgc | tcctctgccc | ctccaggtgc | 1140 |
| tgccttctt | gactctggga | atcggcgtgg | atgacgtatt | cctgctgcg | catgccttca | 1200 |
| cagaggctct | gcctggcacc | cctctccagg | tggggccttg | tccccaggg | ctcatctgag | 1260 |
| gcagctcagc | ttactggtta | agagcctctt | ggttcaagtg | accttgggct | gctaatgaac | 1320 |
| ctcggtgcct | cttgtcccca | tgtgtaaaca | ggggaaataa | tagtgctgtg | tcctaagggt | 1380 |
| tattgtttgg | atcagtgaag | taactcaagt | tgaatgctta | gaacagccca | tcatacgtac | 1440 |
| atggtaccca | ataaatgcta | gccactgtgt | tatgactgcc | ccacctctgc | accccaagtt | 1500 |
| cctgagcctc | cccttcactc | cactttgaca | cggcccctcc | cttgtgacct | gagggcaggt | 1560 |
| ccccactctg | tcctggcagg | agcgcatggg | cgagtgtctg | cagcgcacgg | gcaccagtgt | 1620 |
| tgtactcaca | tccatcaaca | acatggccgc | cttcctcatg | gctgccctcg | ttcccatccc | 1680 |
| tgcgctgcga | gccttctccc | tacagcctgg | acctacggcg | gcgccactgc | cagcgccttg | 1740 |
| atgtgctctg | ctgcttctcc | aggtactgcc | tgcgcccag | cccttcctc | ccgtgaccca | 1800 |
| cgccagcctg | tcccctcacc | agcatttcaa | ggcacagacc | tgtcatccac | tctctacctc | 1860 |

-continued

```
ttccagtccc tgctctgctc aggtgattca gatcctgccc caggagctgg gggacgggac    1920
agtaccagtg ggcattgccc acctcactgc cacagttcaa gcctttaccc actgtgaagc    1980
cagcagccag catgtggtca ccatcctgcc tccccaagcc cacctggtgc ccccaccttc    2040
tgacccactg ggctctgagc tcttcagccc tggagggtcc acacgggacc ttctaggcca    2100
ggaggaggag acaaggcaga aggcagcctg caagtccctg ccctgtgccc gctggaatct    2160
tgcccatttc gcccgctatc agtttgcccc gttgctgctc cagtcacatg ccaaggccat    2220
cgtgctggtg ctctttggtg ctcttctggg cctgagcctc tacggagcca ccttggtgca    2280
agacggcctg gccctgacgg atgtggtgcc tcggggcacc aaggagcatg ccttcctgag    2340
cgcccagctc aggtacttct ccctgtacga ggtggccctg gtgacccagg gtggctttga    2400
ctacgcccac tccaacgcg ccctctttga tctgcaccag cgcttcagtt ccctcaaggc    2460
ggtgctgccc ccaccggcca cccaggcacc ccgcacctgg ctgcactatt accgcaactg    2520
gctacaggga atccaggctg cctttgacca ggactgggct tctgggcgca tcacccgcca    2580
ctcgtaccgc aatggctctg aggatggggc cctggcctac aagctgctca tccagactgg    2640
agacgcccag gagcctctgg atttcagcca ggttgggaga gggctggagg ggtccactag    2700
tacaggggct gcaggcctcc tgggcccagg ccttcagccc tctctgcctc tgcagctgac    2760
cacaaggaag ctggtggaca gagagggact gattccaccc gagctcttct acatggggct    2820
gaccgtgtgg gtgagcagtg accccctggg tctggcagcc tcacaggcca acttctaccc    2880
cccacctcct gaatggctgc acgacaaata cgacaccacg ggggagaacc ttcgcagtga    2940
gtcttggggg gagctcggca agagcctcag cctcgcccac acaagccctg agcctgaggc    3000 cctgccact ctgcccgtg ctcaccgcc tgtccctctc cctcttctcc cttccctcc    3060 cctccacagt cccgccagct cagcccttgg agtttgccca gttccccttc ctgctgcgtg    3120
gcctccagaa gactgcagac tttgtggagg ccatcgaggg ggcccgggca gcatgcgcag    3180
aggccggcca ggctggggtg cacgcctacc ccagcggctc ccccttcctc ttctgggaac    3240
agtatctggg cctgcggcgc tgcttcctgc tggccgtctg catcctgctg gtgtgcactt    3300
tcctcgtctg tgctctgctg ctcctcaacc cctggacggc tggcctcata gtgagtgctt    3360
gcaggagtgg ggacagagac accccaccct tccctgccca gcctgtcatc cctcctgcca    3420
ggagccctct gtgagccctg tctccctcag gtgctggtcc tggcgatgat gacagtggaa    3480
ctctttggta tcatgggttt cctgggcatc aagctgagtg ccatccccgt ggtgatcctt    3540
gtggcctctg taggcattgg cgttgagttc acagtccacg tggctctggt gagcacgggc    3600
accccgggga gggaccaatc agctgattca gtattcaaca catattgttc aagcccctac    3660
tatgtgctag gtactattta agaatttggg ctggtggac gtggtggctc attcctgtaa    3720
tcccagcact ttgggaggcc gaggcgggtg gatcacctga ggtcgggagt tcgaaaccag    3780
cctggccaac atggtgaaac cctgtcttta ctaaaaatac aaaaaattag ccaggcgtgg    3840
tggcacatgc cagtagtccc agctactttg aggctgagg cagaattgct tgaacctggg    3900
aggcgaaggt tgcagtgagc tgagatcgtg ccattgcact ccagcctggg caacaagagt    3960
gcaactctcc gtctcaaaaa aaaaaaaaaa aagggcggcc gcga                   4004
```

<210> SEQ ID NO 9
<211> LENGTH: 2082
<212> TYPE: DNA
<213> ORGANISM: Homo sapiens

<400> SEQUENCE: 9

```
ttccggcatg actcgatcgc cgccccctcag agagctgccc ccgagttaca caccccccagc     60 tcgaaccgca gcaccccaga tcctagctgg gagcctgaag gctccactct ggcttcgtgc    120
ttacttccag ggcctgctct tctctctggg atgcgggatc cagagacatt gtggcaaagt    180
gctctttctg ggactgttgg cctttggggc cctggcatta ggtctccgca tggccattat    240
tgagacaaac ttggaacagc tctgggtaga agtgggcagc cgggtgagcc aggagctgca    300
ttacaccaag gagaagctgg gggaggaggc tgcatacacc tctcagatgc tgatacagac    360
cgcacgccag gagggagaga acatcctcac acccgaagca cttggcctcc acctccaggc    420
agccctcact gccagtaaag tccaagtatc actctatggg aagtcctggg atttgaacaa    480
aatctgctac aagtcaggag ttccccttat tgaaaatgga atgattgagt ggatgattga    540
gaagctgttt ccgtgcgtga tcctcacccc cctcgactgc ttctgggagg gagccaaact    600
ccaagggggc tccgcctacc tgcccggccg cccggatatc cagtggacca acctggatcc    660
agagcagctg ctggaggagc tgggtccctt tgcctcccctt gagggcttcc gggagctgct    720
agacaaggca caggtgggcc aggcctacgt ggggcggccc tgtctgcacc ctgatgacct    780
ccactgccca cctagtgccc ccaaccatca cagcaggcag gctcccaatg tggctcacga    840
gctgagtggg ggctgccatg gcttctccca caaattcatg cactggcagg aggaattgct    900
gctgggaggc atggccagag accccaagg agagctgctg agggcagagg ccctgcagag    960
caccttcttg ctgatgagtc cccgccagct gtacgagcat ttccggggtg actatcagac   1020
acatgacatt ggctggagtg aggagcaggc cagcacagtg ctacaagcct ggcagcggcg   1080 cttttgtgcag ctggcccagg aggccctgcc tgagaacgct tcccagcaga tccatgcctt   1140
ctcctccacc accctggata acatcctgca tgcgttctct gaagtcagtg ctgcccgtgt   1200
ggtgggaggc tatctgctca tgctggccta tgcctgtgtg accatgctgc ggtgggactg   1260
cgcccagtcc cagggttccg tgggccttgc cggggtactg ctggtggccc tggcggtggc   1320
ctcaggcctt gggctctgtg ccctgctcgg catcaccttc aatgctgcca ctacccaggt   1380
gctgcccttc ttggctctgg gaatcggcgt ggatgacgta ttcctgctgg cgcatgcctt   1440
cacagaggct ctgcctggca cccctctcca ggagcgcatg ggcgagtgtc tgcagcgcac   1500
gggcaccagt gtcgtactca catccatcaa caacatggcc gccttcctca tggctgccct   1560
cgttcccatc cctgcgctgc gagccttctc cttacagcca tcctcagcct ggacctacgg   1620
cggcgccact gccagcgcct tgatgtgctc tgctgcttct ccagtccctg ctctgctcag   1680
gtgattcaga tcctgcccca ggagctgggg gacgggacag taccagtggg cattgcccac   1740
ctcactgcca cagttcaagc ctttacccac tgtgaagcca gcagccagca tgtggtcacc   1800
atcctgcctc cccaagccca cctggtgccc ccaccttctg acccactggg ctctgagctc   1860
ttcagccctg gagggtccac acgggaccttt ctaggccagg aggaggagac aaggcagaag   1920
gcagcctgca agtccctgcc ctgtgcccgc tggaatcttg cccatttcgc cccggaattc   1980
ctgcagcccg ggggatccac tagttctaga gcggccgcca ccgcggtgga gctccagctt   2040 ttgttcccctt tagtgagggt taattgcgcg cttgggtatc tt                      2082
```

<210> SEQ ID NO 10
<211> LENGTH: 1315
<212> TYPE: PRT
<213> ORGANISM: Homo sapiens

<400> SEQUENCE: 10

-continued

```
Met Glu Lys Tyr His Val Leu Glu Met Ile Gly Gly Ser Phe Gly
1               5                   10                  15

Arg Val Tyr Lys Gly Arg Arg Lys Tyr Ser Ala Gln Val Val Ala Leu
                20                  25                  30

Lys Phe Ile Pro Lys Leu Gly Arg Ser Glu Lys Glu Leu Arg Asn Leu
            35                  40                  45

Gln Arg Glu Ile Glu Ile Met Arg Gly Leu Arg His Pro Asn Ile Val
    50                  55                  60

His Met Leu Asp Ser Phe Glu Thr Asp Lys Glu Val Val Val Thr
65                  70                  75                  80

Asp Tyr Ala Glu Gly Glu Leu Phe Gln Ile Leu Glu Asp Asp Gly Lys
                85                  90                  95

Leu Pro Glu Asp Gln Val Gln Ala Ile Ala Ala Gln Leu Val Ser Ala
            100                 105                 110

Leu Tyr Tyr Leu His Ser His Arg Ile Leu His Arg Asp Met Lys Pro
        115                 120                 125

Gln Asn Ile Leu Leu Ala Lys Gly Gly Ile Lys Leu Cys Asp Phe
    130                 135                 140

Gly Phe Ala Arg Ala Met Ser Thr Asn Thr Met Val Leu Thr Ser Ile
145                 150                 155                 160

Lys Gly Thr Pro Leu Tyr Met Ser Pro Glu Leu Val Glu Glu Arg Pro
                165                 170                 175

Tyr Asp His Thr Ala Asp Leu Trp Ser Val Gly Cys Ile Leu Tyr Glu
            180                 185                 190

Leu Ala Val Gly Thr Pro Pro Phe Tyr Ala Thr Ser Ile Phe Gln Leu
        195                 200                 205

Val Ser Leu Ile Leu Lys Asp Pro Val Arg Trp Pro Ser Thr Ile Ser
210                 215                 220

Pro Cys Phe Lys Asn Phe Leu Gln Gly Leu Leu Thr Lys Asp Pro Arg
225                 230                 235                 240

Gln Arg Leu Ser Trp Pro Asp Leu Leu Tyr His Pro Phe Ile Ala Gly
                245                 250                 255

His Val Thr Ile Ile Thr Glu Pro Ala Gly Pro Asp Leu Gly Thr Pro
            260                 265                 270

Phe Thr Ser Arg Leu Pro Pro Glu Leu Gln Val Leu Lys Asp Glu Gln
        275                 280                 285

Ala His Arg Leu Ala Pro Lys Gly Asn Gln Ser Arg Ile Leu Thr Gln
    290                 295                 300

Ala Tyr Lys Arg Met Ala Glu Glu Ala Met Gln Lys Lys His Gln Asn
305                 310                 315                 320

Thr Gly Pro Ala Leu Glu Gln Glu Asp Lys Thr Ser Lys Val Ala Pro
                325                 330                 335

Gly Thr Ala Pro Leu Pro Arg Leu Gly Ala Thr Pro Gln Glu Ser Ser
            340                 345                 350

Leu Leu Ala Gly Ile Leu Ala Ser Glu Leu Lys Ser Ser Trp Ala Lys
        355                 360                 365

Ser Gly Thr Gly Glu Val Pro Ser Ala Pro Arg Glu Asn Arg Thr Thr
    370                 375                 380

Pro Asp Cys Glu Arg Ala Phe Pro Glu Glu Arg Pro Glu Val Leu Gly
385                 390                 395                 400

Gln Arg Ser Thr Asp Val Val Asp Leu Glu Asn Glu Glu Pro Asp Ser
                405                 410                 415

Asp Asn Glu Trp Gln His Leu Leu Glu Thr Thr Glu Pro Val Pro Ile
```

-continued

```
                420                 425                 430
Gln Leu Lys Ala Pro Leu Thr Leu Leu Cys Asn Pro Asp Phe Cys Gln
            435                 440                 445
Arg Ile Gln Ser Gln Leu His Glu Ala Gly Gln Ile Leu Lys Gly
        450                 455                 460
Ile Leu Glu Gly Ala Ser His Ile Leu Pro Ala Phe Arg Val Leu Ser
465                 470                 475                 480
Ser Leu Leu Ser Ser Cys Ser Asp Ser Val Ala Leu Tyr Ser Phe Cys
                485                 490                 495
Arg Glu Ala Gly Leu Pro Gly Leu Leu Ser Leu Leu Arg His Ser
            500                 505                 510
Gln Glu Ser Asn Ser Leu Gln Gln Gln Ser Trp Tyr Gly Thr Phe Leu
        515                 520                 525
Gln Asp Leu Met Ala Val Ile Gln Ala Tyr Phe Ala Cys Thr Phe Asn
        530                 535                 540
Leu Glu Arg Ser Gln Thr Ser Asp Ser Leu Gln Val Phe Gln Glu Ala
545                 550                 555                 560
Ala Asn Leu Phe Leu Asp Leu Leu Gly Lys Leu Leu Ala Gln Pro Asp
                565                 570                 575
Asp Ser Glu Gln Thr Leu Arg Arg Asp Ser Leu Met Cys Phe Thr Val
            580                 585                 590
Leu Cys Glu Ala Met Asp Gly Asn Ser Arg Ala Ile Ser Lys Ala Phe
        595                 600                 605
Tyr Ser Ser Leu Leu Thr Thr Gln Gln Val Val Leu Asp Gly Leu Leu
        610                 615                 620
His Gly Leu Thr Val Pro Gln Leu Pro Val His Thr Pro Gln Gly Ala
625                 630                 635                 640
Pro Gln Val Ser Gln Pro Leu Arg Glu Gln Ser Glu Asp Ile Pro Gly
                645                 650                 655
Ala Ile Ser Ser Ala Leu Ala Ala Ile Cys Thr Ala Pro Val Gly Leu
            660                 665                 670
Pro Asp Cys Trp Asp Ala Lys Glu Gln Val Cys Trp His Leu Ala Asn
        675                 680                 685
Gln Leu Thr Glu Asp Ser Ser Gln Leu Arg Pro Ser Leu Ile Ser Gly
        690                 695                 700
Leu Gln His Pro Ile Leu Cys Leu His Leu Leu Lys Val Leu Tyr Ser
705                 710                 715                 720
Cys Cys Leu Val Ser Glu Gly Leu Cys Arg Leu Leu Gly Gln Glu Pro
                725                 730                 735
Leu Ala Leu Glu Ser Leu Phe Met Leu Ile Gln Gly Lys Val Lys Val
            740                 745                 750
Val Asp Trp Glu Glu Ser Thr Glu Val Thr Leu Tyr Phe Leu Ser Leu
        755                 760                 765
Leu Val Phe Arg Leu Gln Asn Leu Pro Cys Gly Met Glu Lys Leu Gly
        770                 775                 780
Ser Asp Val Ala Thr Leu Phe Thr His Ser His Val Ser Leu Val
785                 790                 795                 800
Ser Ala Ala Ala Cys Leu Leu Gly Gln Leu Gly Gln Gln Gly Val Thr
                805                 810                 815
Phe Asp Leu Gln Pro Met Glu Trp Met Ala Ala Thr His Ala Leu
            820                 825                 830
Ser Ala Pro Ala Glu Val Arg Leu Thr Pro Pro Gly Ser Cys Gly Phe
        835                 840                 845
```

-continued

```
Tyr Asp Gly Leu Leu Ile Leu Leu Gln Leu Leu Thr Glu Gln Gly
    850                 855                 860

Lys Ala Ser Leu Ile Arg Asp Met Ser Ser Glu Met Trp Thr Val
865                 870                 875                 880

Leu Trp His Arg Phe Ser Met Val Leu Arg Leu Pro Glu Glu Ala Ser
                    885                 890                 895

Ala Gln Glu Gly Glu Leu Ser Leu Ser Ser Pro Pro Ser Pro Glu Pro
                900                 905                 910

Asp Trp Thr Leu Ile Ser Pro Gln Gly Met Ala Ala Leu Leu Ser Leu
                915                 920                 925

Ala Met Ala Thr Phe Thr Gln Glu Pro Gln Leu Cys Leu Ser Cys Leu
    930                 935                 940

Ser Gln His Gly Ser Ile Leu Met Ser Ile Leu Lys His Leu Leu Cys
945                 950                 955                 960

Pro Ser Phe Leu Asn Gln Leu Arg Gln Ala Pro His Gly Ser Glu Phe
                965                 970                 975

Leu Pro Val Val Val Leu Ser Val Cys Gln Leu Leu Cys Phe Pro Phe
                980                 985                 990

Ala Leu Asp Met Asp Ala Asp Leu Leu Ile Val Val Leu Ala Asp Leu
                995                 1000                1005

Arg Asp Ser Glu Val Ala Ala His Leu Leu Gln Val Cys Cys Tyr
    1010                1015                1020

His Leu Pro Leu Met Gln Val Glu Leu Pro Ile Ser Leu Leu Thr
    1025                1030                1035

Arg Leu Ala Leu Met Asp Pro Thr Ser Leu Asn Gln Phe Val Asn
    1040                1045                1050

Thr Val Ser Ala Ser Pro Arg Thr Ile Val Ser Phe Leu Ser Val
    1055                1060                1065

Ala Leu Leu Ser Asp Gln Pro Leu Leu Thr Ser Asp Leu Leu Ser
    1070                1075                1080

Leu Leu Ala His Thr Ala Arg Val Leu Ser Pro Ser His Leu Ser
    1085                1090                1095

Phe Ile Gln Glu Leu Leu Ala Gly Ser Asp Glu Ser Tyr Arg Pro
    1100                1105                1110

Leu Arg Ser Leu Leu Gly His Pro Glu Asn Ser Val Arg Ala His
    1115                1120                1125

Thr Tyr Arg Leu Leu Gly His Leu Leu Gln His Ser Met Ala Leu
    1130                1135                1140

Arg Gly Ala Leu Gln Ser Gln Ser Gly Leu Leu Ser Leu Leu Leu
    1145                1150                1155

Leu Gly Leu Gly Asp Lys Asp Pro Val Val Arg Cys Ser Ala Ser
    1160                1165                1170

Phe Ala Val Gly Asn Ala Ala Tyr Gln Ala Gly Pro Leu Gly Pro
    1175                1180                1185

Ala Leu Ala Ala Ala Val Pro Ser Met Thr Gln Leu Leu Gly Asp
    1190                1195                1200

Pro Gln Ala Gly Ile Arg Arg Asn Val Ala Ser Ala Leu Gly Asn
    1205                1210                1215

Leu Gly Pro Glu Gly Leu Gly Glu Glu Leu Leu Gln Cys Glu Val
    1220                1225                1230

Pro Gln Arg Leu Leu Glu Met Ala Cys Gly Asp Pro Gln Pro Asn
    1235                1240                1245
```

```
Val Lys Glu Ala Ala Leu Ile Ala Leu Arg Ser Leu Gln Gln Glu
    1250                1255                1260

Pro Gly Ile His Gln Val Leu Val Ser Leu Gly Ala Ser Glu Lys
    1265                1270                1275

Leu Ser Leu Ser Leu Gly Asn Gln Ser Leu Pro His Ser Ser
    1280                1285                1290

Pro Arg Pro Ala Ser Ala Lys His Cys Arg Lys Leu Ile His Leu
    1295                1300                1305

Leu Arg Pro Ala His Ser Met
    1310                1315

<210> SEQ ID NO 11
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 11
ctatgaaatt aaccctcact aaagggagct cccgtgagtc cctatgtg          48

<210> SEQ ID NO 12
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 12
ggattctaat acgactcact atagggcccc taaactccgc tgctccac          48

<210> SEQ ID NO 13
<211> LENGTH: 396
<212> TYPE: PRT
<213> ORGANISM: Mus musculus

<400> SEQUENCE: 13

Met Ala Leu Pro Ala Ser Leu Leu Pro Leu Cys Cys Leu Ala Leu Leu
1               5                   10                  15

Ala Leu Ser Ala Gln Ser Cys Gly Pro Gly Arg Gly Pro Val Gly Arg
            20                  25                  30

Arg Arg Tyr Val Arg Lys Gln Leu Val Pro Leu Leu Tyr Lys Gln Phe
        35                  40                  45

Val Pro Ser Met Pro Glu Arg Thr Leu Gly Ala Ser Gly Pro Ala Glu
    50                  55                  60

Gly Arg Val Thr Arg Gly Ser Glu Arg Phe Arg Asp Leu Val Pro Asn
65                  70                  75                  80

Tyr Asn Pro Asp Ile Ile Phe Lys Asp Glu Glu Asn Ser Gly Ala Asp
                85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
    130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175
```

```
Glu Ser Arg Asn His Ile His Val Ser Val Lys Ala Asp Asn Ser Leu
                180                 185                 190

Ala Val Arg Ala Gly Gly Cys Phe Pro Gly Asn Ala Thr Val Arg Leu
            195                 200                 205

Arg Ser Gly Glu Arg Lys Gly Leu Arg Glu Leu His Arg Gly Asp Trp
        210                 215                 220

Val Leu Ala Ala Asp Ala Ala Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Arg Pro Pro Arg Lys Leu Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
        290                 295                 300

Gly Asp Ala Leu Gln Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu His Ala Leu Gly Ala
        355                 360                 365

Leu Leu Pro Gly Gly Ala Val Gln Pro Thr Gly Met His Trp Tyr Ser
370                 375                 380

Arg Leu Leu Tyr Arg Leu Ala Glu Glu Leu Met Gly
385                 390                 395

<210> SEQ ID NO 14
<211> LENGTH: 437
<212> TYPE: PRT
<213> ORGANISM: Mus musculus

<400> SEQUENCE: 14

Met Leu Leu Leu Leu Ala Arg Cys Phe Leu Val Ile Leu Ala Ser Ser
1               5                   10                  15

Leu Leu Val Cys Pro Gly Leu Ala Cys Gly Pro Gly Arg Gly Phe Gly
            20                  25                  30

Lys Arg Arg His Pro Lys Lys Leu Thr Pro Leu Ala Tyr Lys Gln Phe
        35                  40                  45

Ile Pro Asn Val Ala Glu Lys Thr Leu Gly Ala Ser Gly Arg Tyr Glu
    50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Arg Leu Arg Val Thr Glu Gly
        115                 120                 125

Trp Asp Glu Asp Gly His His Ser Glu Glu Ser Leu His Tyr Glu Gly
    130                 135                 140

Arg Ala Val Asp Ile Thr Thr Ser Asp Arg Asp Arg Ser Lys Tyr Gly
```

-continued

```
                145                 150                 155                 160
Met Leu Ala Arg Leu Ala Val Glu Ala Gly Phe Asp Trp Val Tyr Tyr
                    165                 170                 175

Glu Ser Lys Ala His Ile His Cys Ser Val Lys Ala Glu Asn Ser Val
                180                 185                 190

Ala Ala Lys Ser Gly Gly Cys Phe Pro Gly Ser Ala Thr Val His Leu
            195                 200                 205

Glu Gln Gly Gly Thr Lys Leu Val Lys Asp Leu Arg Pro Gly Asp Arg
        210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Leu Thr Ala Ala His Leu
            260                 265                 270

Leu Phe Val Ala Pro His Asn Asp Ser Gly Pro Thr Pro Gly Pro Ser
        275                 280                 285

Ala Leu Phe Ala Ser Arg Val Arg Pro Gly Gln Arg Val Tyr Val Val
    290                 295                 300

Ala Glu Arg Gly Gly Asp Arg Arg Leu Leu Pro Ala Ala Val His Ser
305                 310                 315                 320

Val Thr Leu Arg Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
        355                 360                 365

Ala His Ala Leu Leu Ala Ala Leu Ala Pro Ala Arg Thr Asp Gly Gly
    370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
            420                 425                 430

Ala Val Lys Ala Ser
        435

<210> SEQ ID NO 15
<211> LENGTH: 803
<212> TYPE: PRT
<213> ORGANISM: Rattus norvegicus

<400> SEQUENCE: 15

Met Ala Ala Gly Arg Pro Val Arg Gly Pro Glu Leu Ala Pro Arg Arg
1               5                   10                  15

Leu Leu Gln Leu Leu Leu Val Leu Leu Gly Gly Arg Gly Arg Gly
            20                  25                  30

Ala Ala Leu Ser Gly Asn Val Thr Gly Pro Gly Pro Arg Ser Ala Gly
        35                  40                  45

Gly Ser Ala Arg Arg Asn Ala Pro Val Thr Ser Pro Pro Pro Leu
    50                  55                  60

Leu Ser His Cys Gly Arg Ala Ala His Cys Glu Pro Leu Arg Tyr Asn
65                  70                  75                  80
```

-continued

```
Val Cys Leu Gly Ser Ala Leu Pro Tyr Gly Ala Thr Thr Thr Leu Leu
                85                  90                  95

Ala Gly Asp Ser Asp Ser Gln Glu Glu Ala His Ser Lys Leu Val Leu
            100                 105                 110

Trp Ser Gly Leu Arg Asn Ala Pro Arg Cys Trp Ala Val Ile Gln Pro
        115                 120                 125

Leu Leu Cys Ala Val Tyr Met Pro Lys Cys Glu Asn Asp Arg Val Glu
    130                 135                 140

Leu Pro Ser Arg Thr Leu Cys Gln Ala Thr Arg Gly Pro Cys Ala Ile
145                 150                 155                 160

Val Glu Arg Glu Arg Gly Trp Pro Asp Phe Leu Arg Cys Thr Pro Asp
                165                 170                 175

His Phe Pro Glu Gly Cys Pro Asn Glu Val Gln Asn Ile Lys Phe Asn
            180                 185                 190

Ser Ser Gly Gln Cys Glu Ala Pro Leu Val Arg Thr Asp Asn Pro Lys
        195                 200                 205

Ser Trp Tyr Glu Asp Val Glu Gly Cys Gly Ile Gln Cys Gln Asn Pro
    210                 215                 220

Leu Phe Thr Glu Ala Glu His Gln Asp Met His Ser Tyr Ile Ala Ala
225                 230                 235                 240

Phe Gly Ala Val Thr Gly Leu Cys Thr Leu Phe Thr Leu Ala Thr Phe
                245                 250                 255

Val Ala Asp Trp Arg Asn Ser Asn Arg Tyr Pro Ala Val Ile Leu Phe
            260                 265                 270

Tyr Val Asn Ala Cys Phe Phe Val Gly Ser Ile Gly Trp Leu Ala Gln
        275                 280                 285

Phe Met Asp Gly Ala Arg Arg Glu Ile Val Cys Arg Ala Asp Gly Thr
    290                 295                 300

Met Arg Phe Gly Glu Pro Thr Ser Ser Glu Thr Leu Ser Cys Val Ile
305                 310                 315                 320

Ile Phe Val Ile Val Tyr Tyr Ala Leu Met Ala Gly Val Val Trp Phe
                325                 330                 335

Val Val Leu Thr Tyr Ala Trp His Thr Ser Phe Lys Ala Leu Gly Thr
            340                 345                 350

Thr Tyr Gln Pro Leu Ser Gly Lys Thr Ser Tyr Phe His Leu Leu Thr
        355                 360                 365

Trp Ser Leu Pro Phe Val Leu Thr Val Ala Ile Leu Ala Val Ala Gln
    370                 375                 380

Val Asp Gly Asp Ser Val Ser Gly Ile Cys Phe Val Gly Tyr Lys Asn
385                 390                 395                 400

Tyr Arg Tyr Arg Ala Gly Phe Val Leu Ala Pro Ile Gly Leu Val Leu
                405                 410                 415

Ile Val Gly Gly Tyr Phe Leu Ile Arg Gly Val Met Thr Leu Phe Ser
            420                 425                 430

Ile Lys Ser Asn His Pro Gly Leu Leu Ser Glu Lys Ala Ala Ser Lys
        435                 440                 445

Ile Asn Glu Thr Met Leu Arg Leu Gly Ile Phe Gly Phe Leu Ala Phe
    450                 455                 460

Gly Phe Val Leu Ile Thr Phe Ser Cys His Phe Tyr Asp Phe Phe Asn
465                 470                 475                 480

Gln Ala Glu Trp Glu Arg Ser Phe Arg Asp Tyr Val Leu Cys Gln Ala
                485                 490                 495

Asn Val Thr Ile Gly Leu Pro Thr Lys Lys Pro Ile Pro Asp Cys Glu
```

-continued

```
                500                 505                 510
Ile Lys Asn Arg Pro Ser Leu Leu Val Glu Lys Ile Asn Leu Phe Ala
            515                 520                 525

Met Phe Gly Thr Gly Ile Ala Met Ser Thr Trp Val Trp Thr Lys Ala
530                 535                 540

Thr Leu Leu Ile Trp Arg Arg Thr Trp Cys Arg Leu Thr Gly His Ser
545                 550                 555                 560

Asp Asp Glu Pro Lys Arg Ile Lys Lys Ser Lys Met Ile Ala Lys Ala
                565                 570                 575

Phe Ser Lys Arg Arg Glu Leu Leu Gln Asn Pro Gly Gln Glu Leu Ser
            580                 585                 590

Phe Ser Met His Thr Val Ser His Asp Gly Pro Val Ala Gly Leu Ala
            595                 600                 605

Phe Glu Leu Asn Glu Pro Ser Ala Asp Val Ser Ser Ala Trp Ala Gln
            610                 615                 620

His Val Thr Lys Met Val Ala Arg Arg Gly Ala Ile Leu Pro Gln Asp
625                 630                 635                 640

Val Ser Val Thr Pro Val Ala Thr Pro Val Pro Pro Glu Glu Gln Ala
                645                 650                 655

Asn Leu Trp Leu Val Glu Ala Glu Ile Ser Pro Glu Leu Glu Lys Arg
            660                 665                 670

Leu Gly Arg Lys Lys Arg Lys Arg Lys Lys Glu Val Cys Pro
            675                 680                 685

Leu Gly Pro Ala Pro Glu Leu His His Ser Ala Pro Val Pro Ala Thr
            690                 695                 700

Ser Ala Val Pro Arg Leu Pro Gln Leu Pro Arg Gln Lys Cys Leu Val
705                 710                 715                 720

Ala Ala Asn Ala Trp Gly Thr Gly Glu Pro Cys Arg Gln Gly Ala Trp
                725                 730                 735

Thr Val Val Ser Asn Pro Phe Cys Glu Pro Ser Pro His Gln Asp
            740                 745                 750

Pro Phe Leu Pro Gly Ala Ser Ala Pro Arg Val Trp Ala Gln Gly Arg
            755                 760                 765

Leu Gln Gly Leu Gly Ser Ile His Ser Arg Thr Asn Leu Met Glu Ala
            770                 775                 780

Glu Leu Leu Asp Ala Asp Ser Asp Phe Glu Gln Lys Leu Ile Ser Glu
785                 790                 795                 800

Glu Asp Leu

<210> SEQ ID NO 16
<211> LENGTH: 793
<212> TYPE: PRT
<213> ORGANISM: Rattus norvegicus

<400> SEQUENCE: 16

Met Ala Ala Gly Arg Pro Val Arg Gly Pro Glu Leu Ala Pro Arg Arg
1               5                   10                  15

Leu Leu Gln Leu Leu Leu Val Leu Gly Arg Gly Arg Gly
            20                  25                  30

Ala Ala Leu Ser Gly Asn Val Thr Gly Pro Gly Pro Arg Ser Ala Gly
            35                  40                  45

Gly Ser Ala Arg Arg Asn Ala Pro Val Thr Ser Pro Pro Pro Leu
        50                  55                  60

Leu Ser His Cys Gly Arg Ala Ala His Cys Glu Pro Leu Arg Tyr Asn
```

-continued

```
             65                  70                  75                  80
Val Cys Leu Gly Ser Ala Leu Pro Tyr Gly Ala Thr Thr Leu Leu
                    85                  90                  95
Ala Gly Asp Ser Asp Ser Gln Glu Ala His Ser Lys Leu Val Leu
                100                 105                 110
Trp Ser Gly Leu Arg Asn Ala Pro Arg Cys Trp Ala Val Ile Gln Pro
                115                 120                 125
Leu Leu Cys Ala Val Tyr Met Pro Lys Cys Glu Asn Asp Arg Val Glu
        130                 135                 140
Leu Pro Ser Arg Thr Leu Cys Gln Ala Thr Arg Gly Pro Cys Ala Ile
145                 150                 155                 160
Val Glu Arg Glu Arg Gly Trp Pro Asp Phe Leu Arg Cys Thr Pro Asp
                165                 170                 175
His Phe Pro Glu Gly Cys Pro Asn Glu Val Gln Asn Ile Lys Phe Asn
                180                 185                 190
Ser Ser Gly Gln Cys Glu Ala Pro Leu Val Arg Thr Asp Asn Pro Lys
                195                 200                 205
Ser Trp Tyr Glu Asp Val Glu Gly Cys Gly Ile Gln Cys Gln Asn Pro
        210                 215                 220
Leu Phe Thr Glu Ala Glu His Gln Asp Met His Ser Tyr Ile Ala Ala
225                 230                 235                 240
Phe Gly Ala Val Thr Gly Leu Cys Thr Leu Phe Thr Leu Ala Thr Phe
                    245                 250                 255
Val Ala Asp Trp Arg Asn Ser Asn Arg Tyr Pro Ala Val Ile Leu Phe
                260                 265                 270
Tyr Val Asn Ala Cys Phe Phe Val Gly Ser Ile Gly Trp Leu Ala Gln
                275                 280                 285
Phe Met Asp Gly Ala Arg Arg Glu Ile Val Cys Arg Ala Asp Gly Thr
        290                 295                 300
Met Arg Phe Gly Glu Pro Thr Ser Ser Glu Thr Leu Ser Cys Val Ile
305                 310                 315                 320
Ile Phe Val Ile Val Tyr Tyr Ala Leu Met Ala Gly Val Val Trp Phe
                    325                 330                 335
Val Val Leu Thr Tyr Ala Trp His Thr Ser Phe Lys Ala Leu Gly Thr
                340                 345                 350
Thr Tyr Gln Pro Leu Ser Gly Lys Thr Ser Tyr Phe His Leu Leu Thr
        355                 360                 365
Trp Ser Leu Pro Phe Val Leu Thr Val Ala Ile Leu Ala Val Ala Gln
        370                 375                 380
Val Asp Gly Asp Ser Val Ser Gly Ile Cys Phe Val Gly Tyr Lys Asn
385                 390                 395                 400
Tyr Arg Tyr Arg Ala Gly Phe Val Leu Ala Pro Ile Gly Leu Val Leu
                405                 410                 415
Ile Val Gly Gly Tyr Phe Leu Ile Arg Gly Val Met Thr Leu Phe Ser
                420                 425                 430
Ile Lys Ser Asn His Pro Gly Leu Leu Ser Glu Lys Ala Ala Ser Lys
                435                 440                 445
Ile Asn Glu Thr Met Leu Arg Leu Gly Ile Phe Gly Phe Leu Ala Phe
        450                 455                 460
Gly Phe Val Leu Ile Thr Phe Ser Cys His Phe Tyr Asp Phe Phe Asn
465                 470                 475                 480
Gln Ala Glu Trp Glu Arg Ser Phe Arg Asp Tyr Val Leu Cys Gln Ala
                485                 490                 495
```

```
Asn Val Thr Ile Gly Leu Pro Thr Lys Lys Pro Ile Pro Asp Cys Glu
            500                 505                 510
Ile Lys Asn Arg Pro Ser Leu Leu Val Glu Lys Ile Asn Leu Phe Ala
        515                 520                 525
Met Phe Gly Thr Gly Ile Ala Met Ser Thr Leu Val Trp Thr Lys Ala
    530                 535                 540
Thr Leu Leu Ile Trp Arg Arg Thr Trp Cys Arg Leu Thr Gly His Ser
545                 550                 555                 560
Asp Asp Glu Pro Lys Arg Ile Lys Lys Ser Lys Met Ile Ala Lys Ala
                565                 570                 575
Phe Ser Lys Arg Arg Glu Leu Leu Gln Asn Pro Gly Gln Glu Leu Ser
            580                 585                 590
Phe Ser Met His Thr Val Ser His Asp Gly Pro Val Ala Gly Leu Ala
        595                 600                 605
Phe Glu Leu Asn Glu Pro Ser Ala Asp Val Ser Ser Ala Trp Ala Gln
    610                 615                 620
His Val Thr Lys Met Val Ala Arg Arg Gly Ala Ile Leu Pro Gln Asp
625                 630                 635                 640
Val Ser Val Thr Pro Val Ala Thr Pro Val Pro Glu Glu Gln Ala
                645                 650                 655
Asn Leu Trp Leu Val Glu Ala Glu Ile Ser Pro Glu Leu Glu Lys Arg
            660                 665                 670
Leu Gly Arg Lys Lys Lys Arg Lys Arg Lys Lys Glu Val Cys Pro
        675                 680                 685
Leu Gly Pro Ala Pro Glu Leu His His Ser Ala Pro Val Pro Ala Thr
    690                 695                 700
Ser Ala Val Pro Arg Leu Pro Gln Leu Pro Arg Gln Lys Cys Leu Val
705                 710                 715                 720
Ala Ala Asn Ala Trp Gly Thr Gly Glu Pro Cys Arg Gln Gly Ala Trp
                725                 730                 735
Thr Val Val Ser Asn Pro Phe Cys Pro Glu Pro Ser Pro His Gln Asp
            740                 745                 750
Pro Phe Leu Pro Gly Ala Ser Ala Pro Arg Val Trp Ala Gln Gly Arg
        755                 760                 765
Leu Gln Gly Leu Gly Ser Ile His Ser Arg Thr Asn Leu Met Glu Ala
    770                 775                 780
Glu Leu Leu Asp Ala Asp Ser Asp Phe
785                 790

<210> SEQ ID NO 17
<211> LENGTH: 793
<212> TYPE: PRT
<213> ORGANISM: Homo sapiens

<400> SEQUENCE: 17

Met Ala Ala Gly Arg Pro Val Arg Gly Pro Glu Leu Ala Pro Arg Arg
1               5                   10                  15
Leu Leu Gln Leu Leu Leu Val Leu Gly Arg Gly Arg Gly
            20                  25                  30
Ala Ala Leu Ser Gly Asn Val Thr Gly Pro Gly Pro Arg Ser Ala Gly
        35                  40                  45
Gly Ser Ala Arg Arg Asn Ala Pro Val Thr Ser Pro Pro Pro Leu
    50                  55                  60
Leu Ser His Cys Gly Arg Ala Ala His Cys Glu Pro Leu Arg Tyr Asn
```

```
          65                  70                  75                  80
Val Cys Leu Gly Ser Ala Leu Pro Tyr Gly Thr Thr Leu Leu
                    85                  90                  95
Ala Gly Asp Ser Asp Ser Gln Glu Ala His Ser Lys Leu Val Leu
                100                 105                 110
Trp Ser Gly Leu Arg Asn Ala Pro Arg Cys Trp Ala Val Ile Gln Pro
            115                 120                 125
Leu Leu Cys Ala Val Tyr Met Pro Lys Cys Glu Asn Asp Arg Val Glu
        130                 135                 140
Leu Pro Ser Arg Thr Leu Cys Gln Ala Thr Arg Gly Pro Cys Ala Ile
145                 150                 155                 160
Val Glu Arg Glu Arg Gly Trp Pro Asp Phe Leu Arg Cys Thr Pro Asp
                165                 170                 175
His Phe Pro Glu Gly Cys Pro Asn Glu Val Gln Asn Ile Lys Phe Asn
                180                 185                 190
Ser Ser Gly Gln Cys Glu Ala Pro Leu Val Arg Thr Asp Asn Pro Lys
            195                 200                 205
Ser Trp Tyr Glu Asp Val Glu Gly Cys Gly Ile Gln Cys Gln Asn Pro
        210                 215                 220
Leu Phe Thr Glu Ala Glu His Gln Asp Met His Ser Tyr Ile Ala Ala
225                 230                 235                 240
Phe Gly Ala Val Thr Gly Leu Cys Thr Leu Phe Thr Leu Ala Thr Phe
                245                 250                 255
Val Ala Asp Trp Arg Asn Ser Asn Arg Tyr Pro Ala Val Ile Leu Phe
                260                 265                 270
Tyr Val Asn Ala Cys Phe Phe Val Gly Ser Ile Gly Trp Leu Ala Gln
            275                 280                 285
Phe Met Asp Gly Ala Arg Arg Glu Ile Val Cys Arg Ala Asp Gly Thr
        290                 295                 300
Met Arg Phe Gly Glu Pro Thr Ser Ser Glu Thr Leu Ser Cys Val Ile
305                 310                 315                 320
Ile Phe Val Ile Val Tyr Tyr Ala Leu Met Ala Gly Val Val Trp Phe
                325                 330                 335
Val Val Leu Thr Tyr Ala Trp His Thr Ser Phe Lys Ala Leu Gly Thr
            340                 345                 350
Thr Tyr Gln Pro Leu Ser Gly Lys Thr Ser Tyr Phe His Leu Leu Thr
        355                 360                 365
Trp Ser Leu Pro Phe Val Leu Thr Val Ala Ile Leu Ala Val Ala Gln
370                 375                 380
Val Asp Gly Asp Ser Val Ser Gly Ile Cys Phe Val Gly Tyr Lys Asn
385                 390                 395                 400
Tyr Arg Tyr Arg Ala Gly Phe Val Leu Ala Pro Ile Gly Leu Val Leu
                405                 410                 415
Ile Val Gly Gly Tyr Phe Leu Ile Arg Gly Val Met Thr Leu Phe Ser
            420                 425                 430
Ile Lys Ser Asn His Pro Gly Leu Leu Ser Glu Lys Ala Ala Ser Lys
        435                 440                 445
Ile Asn Glu Thr Met Leu Arg Leu Gly Ile Phe Gly Phe Leu Ala Phe
    450                 455                 460
Gly Phe Val Leu Ile Thr Phe Ser Cys His Phe Tyr Asp Phe Phe Asn
465                 470                 475                 480
Gln Ala Glu Trp Glu Arg Ser Phe Arg Asp Tyr Val Leu Cys Gln Ala
                485                 490                 495
```

```
Asn Val Thr Ile Gly Leu Pro Thr Lys Lys Pro Ile Pro Asp Cys Glu
            500                 505                 510

Ile Lys Asn Arg Pro Ser Leu Leu Val Glu Lys Ile Asn Leu Phe Ala
        515                 520                 525

Met Phe Gly Thr Gly Ile Ala Met Ser Thr Trp Val Trp Thr Lys Ala
    530                 535                 540

Thr Leu Leu Ile Trp Arg Arg Thr Trp Cys Arg Leu Thr Gly His Ser
545                 550                 555                 560

Asp Asp Glu Pro Lys Arg Ile Lys Lys Ser Lys Met Ile Ala Lys Ala
                565                 570                 575

Phe Ser Lys Arg Arg Glu Leu Leu Gln Asn Pro Gly Gln Glu Leu Ser
            580                 585                 590

Phe Ser Met His Thr Val Ser His Asp Gly Pro Val Ala Gly Leu Ala
        595                 600                 605

Phe Glu Leu Asn Glu Pro Ser Ala Asp Val Ser Ser Ala Trp Ala Gln
    610                 615                 620

His Val Thr Lys Met Val Ala Arg Arg Gly Ala Ile Leu Pro Gln Asp
625                 630                 635                 640

Val Ser Val Thr Pro Val Ala Thr Pro Val Pro Glu Glu Gln Ala
                645                 650                 655

Asn Leu Trp Leu Val Glu Ala Glu Ile Ser Pro Glu Leu Glu Lys Arg
            660                 665                 670

Leu Gly Arg Lys Lys Lys Arg Arg Lys Arg Lys Lys Glu Val Cys Pro
        675                 680                 685

Leu Gly Pro Ala Pro Glu Leu His His Ser Ala Pro Val Pro Ala Thr
    690                 695                 700

Ser Ala Val Pro Arg Leu Pro Gln Leu Pro Arg Gln Lys Cys Leu Val
705                 710                 715                 720

Ala Ala Asn Ala Trp Gly Thr Gly Glu Pro Cys Arg Gln Gly Ala Trp
                725                 730                 735

Thr Val Val Ser Asn Pro Phe Cys Pro Glu Pro Ser Pro His Gln Asp
            740                 745                 750

Pro Phe Leu Pro Gly Ala Ser Ala Pro Arg Val Trp Ala Gln Gly Arg
        755                 760                 765

Leu Gln Gly Leu Gly Ser Ile His Ser Arg Thr Asn Leu Met Glu Ala
    770                 775                 780

Glu Leu Leu Asp Ala Asp Ser Asp Phe
785                 790

<210> SEQ ID NO 18
<211> LENGTH: 228
<212> TYPE: DNA
<213> ORGANISM: Homo sapiens

<400> SEQUENCE: 18
ctggggctgt ccagttaccc caacggctac cccttcctct tctgggagca gtacatcggc        60
ctccgccact ggctgctgct gttcatcagc gtggtgttgg cctgcacatt cctcgtgtgc       120
gctgtcttcc ttctgaaccc ctggacggcc gggatcattg tgatggtcct ggcgctgatg       180
acggtcgagc tgttcggcat gatgggcctc atcggaatca agctcagt                   228

<210> SEQ ID NO 19
<211> LENGTH: 18
<212> TYPE: DNA
<213> ORGANISM: Homo sapiens
```

```
<400> SEQUENCE: 19
aggcggggga tcacagca                                                   18

<210> SEQ ID NO 20
<211> LENGTH: 18
<212> TYPE: DNA
<213> ORGANISM: Homo sapiens

<400> SEQUENCE: 20
ataccaaaga gttccact                                                   18

<210> SEQ ID NO 21
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 21
ctgcggcgct gcttcctgct ggccgtctgc atcctgctgg tgtgc                     45

<210> SEQ ID NO 22
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 22
agagcacaga cgaggaaagt gcacaccagc aggatgcaga cggcc                     45

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 23
actcctgact tgtagcagat t                                               21

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 24
aggctgcata cacctctcag a                                               21

<210> SEQ ID NO 25
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 25
gcttaggccc gaggagat                                                   18

<210> SEQ ID NO 26
<211> LENGTH: 20
<212> TYPE: DNA
```

-continued

```
<213> ORGANISM: Artificial Sequence
<220> FEATURE:
<223> OTHER INFORMATION: Synthetic oligonucleotide

<400> SEQUENCE: 26
aactcacaac tttctctcca                                                   20

<210> SEQ ID NO 27
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 27
ggattctaat acgactcact atagggccca atggcctaaa ccgactgc                    48

<210> SEQ ID NO 28
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 28
ctatgaaatt aaccctcact aaagggaccc acggcctctc ctcaca                      46

<210> SEQ ID NO 29
<211> LENGTH: 449
<212> TYPE: PRT
<213> ORGANISM: Mus musculus

<400> SEQUENCE: 29

Met Glu Ser Pro Arg Ala Thr Gln Thr Pro Glu Ser Pro Lys Leu Ser
1               5                   10                  15

Gln Pro Arg Ala His Leu Ser Ala His Gln Ala Pro Ser Pro Ala Ala
            20                  25                  30

Leu Pro Gly Tyr Pro Ala Met Ser Pro Ala Trp Leu Arg Pro Arg Leu
        35                  40                  45

Arg Phe Cys Leu Phe Leu Leu Leu Leu Leu Val Pro Ala Ala Arg
    50                  55                  60

Gly Cys Gly Pro Gly Arg Val Val Gly Ser Arg Arg Pro Arg
65                  70                  75                  80

Lys Leu Val Pro Leu Ala Tyr Lys Gln Phe Ser Pro Asn Val Pro Glu
                85                  90                  95

Lys Thr Leu Gly Ala Ser Gly Arg Tyr Glu Gly Lys Ile Ala Arg Ser
            100                 105                 110

Ser Glu Arg Phe Lys Glu Leu Thr Pro Asn Tyr Asn Pro Asp Ile Ile
        115                 120                 125

Phe Lys Asp Glu Glu Asn Thr Gly Ala Asp Arg Leu Met Thr Gln Arg
    130                 135                 140

Cys Lys Asp Arg Leu Asn Ser Leu Ala Ile Ser Val Met Asn Gln Trp
145                 150                 155                 160

Pro Gly Val Lys Leu Arg Val Thr Glu Gly Trp Asp Glu Asp Gly His
                165                 170                 175

His Ser Glu Glu Ser Leu His Tyr Glu Gly Arg Ala Val Asp Ile Thr
            180                 185                 190

Thr Ser Asp Arg Asp Arg Asn Lys Tyr Gly Leu Leu Ala Arg Leu Ala
        195                 200                 205
```

Val Glu Ala Gly Phe Asp Trp Val Tyr Tyr Glu Ser Lys Ala His Val
    210                 215                 220

His Cys Ser Val Lys Ser Glu His Ser Ala Ala Ala Lys Thr Gly Gly
225                 230                 235                 240

Cys Phe Pro Ala Gly Ala Gln Val Arg Leu Glu Asn Gly Glu Arg Val
                245                 250                 255

Ala Leu Ser Ala Val Lys Pro Gly Asp Arg Val Leu Ala Met Gly Glu
            260                 265                 270

Asp Gly Thr Pro Thr Phe Ser Asp Val Leu Ile Phe Leu Asp Arg Glu
        275                 280                 285

Pro Asn Arg Leu Arg Ala Phe Gln Val Ile Glu Thr Gln Asp Pro Pro
    290                 295                 300

Arg Arg Leu Ala Leu Thr Pro Ala His Leu Leu Phe Ile Ala Asp Asn
305                 310                 315                 320

His Thr Glu Pro Ala Ala His Phe Arg Ala Thr Phe Ala Ser His Val
                325                 330                 335

Gln Pro Gly Gln Tyr Val Leu Val Ser Gly Val Pro Gly Leu Gln Pro
            340                 345                 350

Ala Arg Val Ala Ala Val Ser Thr His Val Ala Leu Gly Ser Tyr Ala
        355                 360                 365

Pro Leu Thr Arg His Gly Thr Leu Val Val Glu Asp Val Val Ala Ser
    370                 375                 380

Cys Phe Ala Ala Val Ala Asp His His Leu Ala Gln Leu Ala Phe Trp
385                 390                 395                 400

Pro Leu Arg Leu Phe Pro Ser Leu Ala Trp Gly Ser Trp Thr Pro Ser
                405                 410                 415

Glu Gly Val His Trp Tyr Pro Gln Met Leu Tyr Arg Leu Gly Arg Leu
            420                 425                 430

Leu Leu Glu Glu Ser Thr Phe His Pro Leu Gly Met Ser Gly Ala Gly
        435                 440                 445

Ser

<210> SEQ ID NO 30
<211> LENGTH: 228
<212> TYPE: DNA
<213> ORGANISM: Homo sapiens

<400> SEQUENCE: 30
ctggggctgt ccagttaccc caacggctac cccttcctct tctgggagca gtacatcggc      60
ctccgccact ggctgctgct gttcatcagc gtggtgttgg cctgcacatt cctcgtgtgc     120
gctgtcttcc ttctgaaccc ctggacggcc gggatcattg tgatggtcct ggcgctgatg     180
acggtcgagc tgttcggcat gatgggcctc atcggaatca agctcagt                  228

<210> SEQ ID NO 31
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 31
tcgacaagca gggaacaccc aagtagaagc tc                                    32

<210> SEQ ID NO 32
<211> LENGTH: 32
<212> TYPE: DNA

<213> ORGANISM: Artificial Sequence
<220> FEATURE:
<223> OTHER INFORMATION: Synthetic oligonucleotide

<400> SEQUENCE: 32
tcgacaagca gggaagtggg aagtagaagc tc                32

<210> SEQ ID NO 33
<211> LENGTH: 1447
<212> TYPE: PRT
<213> ORGANISM: Homo sapiens

<400> SEQUENCE: 33

```
Met Ala Ser Ala Gly Asn Ala Ala Glu Pro Gln Asp Arg Gly Gly Gly
1               5                   10                  15

Gly Ser Gly Cys Ile Gly Ala Pro Arg Pro Ala Gly Gly Gly Arg
            20                  25                  30

Arg Arg Arg Thr Gly Gly Leu Arg Arg Ala Ala Pro Asp Arg Asp
                35                  40                  45

Tyr Leu His Arg Pro Ser Tyr Cys Asp Ala Ala Phe Ala Leu Glu Gln
    50                  55                  60

Ile Ser Lys Gly Lys Ala Thr Gly Arg Lys Ala Pro Leu Trp Leu Arg
65                  70                  75                  80

Ala Lys Phe Gln Arg Leu Leu Phe Lys Leu Gly Cys Tyr Ile Gln Lys
                85                  90                  95

Asn Cys Gly Lys Phe Leu Val Val Gly Leu Leu Ile Phe Gly Ala Phe
            100                 105                 110

Ala Val Gly Leu Lys Ala Ala Asn Leu Glu Thr Asn Val Glu Glu Leu
        115                 120                 125

Trp Val Glu Val Gly Gly Arg Val Ser Arg Glu Leu Asn Tyr Thr Arg
130                 135                 140

Gln Lys Ile Gly Glu Glu Ala Met Phe Asn Pro Gln Leu Met Ile Gln
145                 150                 155                 160

Thr Pro Lys Glu Glu Gly Ala Asn Val Leu Thr Thr Glu Ala Leu Leu
                165                 170                 175

Gln His Leu Asp Ser Ala Leu Gln Ala Ser Arg Val His Val Tyr Met
            180                 185                 190

Tyr Asn Arg Gln Trp Lys Leu Glu His Leu Cys Tyr Lys Ser Gly Glu
        195                 200                 205

Leu Ile Thr Glu Thr Gly Tyr Met Asp Gln Ile Ile Glu Tyr Leu Tyr
    210                 215                 220

Pro Cys Leu Ile Ile Thr Pro Leu Asp Cys Phe Trp Glu Gly Ala Lys
225                 230                 235                 240

Leu Gln Ser Gly Thr Ala Tyr Leu Leu Gly Lys Pro Pro Leu Arg Trp
                245                 250                 255

Thr Asn Phe Asp Pro Leu Glu Phe Leu Glu Glu Leu Lys Lys Ile Asn
            260                 265                 270

Tyr Gln Val Asp Ser Trp Glu Glu Met Leu Asn Lys Ala Glu Val Gly
        275                 280                 285

His Gly Tyr Met Asp Arg Pro Cys Leu Asn Pro Ala Asp Pro Asp Cys
    290                 295                 300

Pro Ala Thr Ala Pro Asn Lys Asn Ser Thr Lys Pro Leu Asp Met Ala
305                 310                 315                 320

Leu Val Leu Asn Gly Gly Cys His Gly Leu Ser Arg Lys Tyr Met His
                325                 330                 335
```

```
Trp Gln Glu Glu Leu Ile Val Gly Gly Thr Val Lys Asn Ser Thr Gly
                340                 345                 350
Lys Leu Val Ser Ala His Ala Leu Gln Thr Met Phe Gln Leu Met Thr
            355                 360                 365
Pro Lys Gln Met Tyr Glu His Phe Lys Gly Tyr Glu Tyr Val Ser His
370                 375                 380
Ile Asn Trp Asn Glu Asp Lys Ala Ala Ala Ile Leu Glu Ala Trp Gln
385                 390                 395                 400
Arg Thr Tyr Val Glu Val His Gln Ser Val Ala Gln Asn Ser Thr
                405                 410                 415
Gln Lys Val Leu Ser Phe Thr Thr Thr Leu Asp Asp Ile Leu Lys
            420                 425                 430
Ser Phe Ser Asp Val Ser Val Ile Arg Val Ala Ser Gly Tyr Leu Leu
            435                 440                 445
Met Leu Ala Tyr Ala Cys Leu Thr Met Leu Arg Trp Asp Cys Ser Lys
        450                 455                 460
Ser Gln Gly Ala Val Gly Leu Ala Gly Val Leu Leu Val Ala Leu Ser
465                 470                 475                 480
Val Ala Ala Gly Leu Gly Leu Cys Ser Leu Ile Gly Ile Ser Phe Asn
                485                 490                 495
Ala Ala Thr Thr Gln Val Leu Pro Phe Leu Ala Leu Gly Val Gly Val
            500                 505                 510
Asp Asp Val Phe Leu Leu Ala His Ala Phe Ser Glu Thr Gly Gln Asn
            515                 520                 525
Lys Arg Ile Pro Phe Glu Asp Arg Thr Gly Glu Cys Leu Lys Arg Thr
530                 535                 540
Gly Ala Ser Val Ala Leu Thr Ser Ile Ser Asn Val Thr Ala Phe Phe
545                 550                 555                 560
Met Ala Ala Leu Ile Pro Ile Pro Ala Leu Arg Ala Phe Ser Leu Gln
                565                 570                 575
Ala Ala Val Val Val Phe Asn Phe Ala Met Val Leu Leu Ile Phe
            580                 585                 590
Pro Ala Ile Leu Ser Met Asp Leu Tyr Arg Arg Glu Asp Arg Arg Leu
            595                 600                 605
Asp Ile Phe Cys Cys Phe Thr Ser Pro Cys Val Ser Arg Val Ile Gln
        610                 615                 620
Val Glu Pro Gln Ala Tyr Thr Asp Thr His Asp Asn Thr Arg Tyr Ser
625                 630                 635                 640
Pro Pro Pro Pro Tyr Ser Ser His Ser Phe Ala His Glu Thr Gln Ile
                645                 650                 655
Thr Met Gln Ser Thr Val Gln Leu Arg Thr Glu Tyr Asp Pro His Thr
            660                 665                 670
His Val Tyr Tyr Thr Thr Ala Glu Pro Arg Ser Glu Ile Ser Val Gln
            675                 680                 685
Pro Val Thr Val Thr Gln Asp Thr Leu Ser Cys Gln Ser Pro Glu Ser
        690                 695                 700
Thr Ser Ser Thr Arg Asp Leu Leu Ser Gln Phe Ser Asp Ser Ser Leu
705                 710                 715                 720
His Cys Leu Glu Pro Pro Cys Thr Lys Trp Thr Leu Ser Ser Phe Ala
                725                 730                 735
Glu Lys His Tyr Ala Pro Phe Leu Leu Lys Pro Lys Ala Lys Val Val
            740                 745                 750
Val Ile Phe Leu Phe Leu Gly Leu Leu Gly Val Ser Leu Tyr Gly Thr
```

-continued

```
                755                 760                 765
Thr Arg Val Arg Asp Gly Leu Asp Leu Thr Asp Ile Val Pro Arg Glu
770                 775                 780

Thr Arg Glu Tyr Asp Phe Ile Ala Ala Gln Phe Lys Tyr Phe Ser Phe
785                 790                 795                 800

Tyr Asn Met Tyr Ile Val Thr Gln Lys Ala Asp Tyr Pro Asn Ile Gln
                805                 810                 815

His Leu Leu Tyr Asp Leu His Arg Ser Phe Ser Asn Val Lys Tyr Val
                820                 825                 830

Met Leu Glu Glu Asn Lys Gln Leu Pro Lys Met Trp Leu His Tyr Phe
                835                 840                 845

Arg Asp Trp Leu Gln Gly Leu Gln Asp Ala Phe Asp Ser Asp Trp Glu
                850                 855                 860

Thr Gly Lys Ile Met Pro Asn Asn Tyr Lys Asn Gly Ser Asp Asp Gly
865                 870                 875                 880

Val Leu Ala Tyr Lys Leu Leu Val Gln Thr Gly Ser Arg Asp Lys Pro
                885                 890                 895

Ile Asp Ile Ser Gln Leu Thr Lys Gln Arg Leu Val Asp Ala Asp Gly
                900                 905                 910

Ile Ile Asn Pro Ser Ala Phe Tyr Ile Tyr Leu Thr Ala Trp Val Ser
                915                 920                 925

Asn Asp Pro Val Ala Tyr Ala Ala Ser Gln Ala Asn Ile Arg Pro His
                930                 935                 940

Arg Pro Glu Trp Val His Asp Lys Ala Asp Tyr Met Pro Glu Thr Arg
945                 950                 955                 960

Leu Arg Ile Pro Ala Ala Glu Pro Ile Glu Tyr Ala Gln Phe Pro Phe
                965                 970                 975

Tyr Leu Asn Gly Leu Arg Asp Thr Ser Asp Phe Val Glu Ala Ile Glu
                980                 985                 990

Lys Val Arg Thr Ile Cys Ser Asn Tyr Thr Ser Leu Gly Leu Ser Ser
                995                 1000                1005

Tyr Pro Asn Gly Tyr Pro Phe Leu Phe Trp Glu Gln Tyr Ile Gly
1010                1015                1020

Leu Arg His Trp Leu Leu Leu Phe Ile Ser Val Val Leu Ala Cys
1025                1030                1035

Thr Phe Leu Val Cys Ala Val Phe Leu Leu Asn Pro Trp Thr Ala
1040                1045                1050

Gly Ile Ile Val Met Val Leu Ala Leu Met Thr Val Glu Leu Phe
1055                1060                1065

Gly Met Met Gly Leu Ile Gly Ile Lys Leu Ser Ala Val Pro Val
1070                1075                1080

Val Ile Leu Ile Ala Ser Val Gly Ile Gly Val Glu Phe Thr Val
1085                1090                1095

His Val Ala Leu Ala Phe Leu Thr Ala Ile Gly Asp Lys Asn Arg
1100                1105                1110

Arg Ala Val Leu Ala Leu Glu His Met Phe Ala Pro Val Leu Asp
1115                1120                1125

Gly Ala Val Ser Thr Leu Leu Gly Val Leu Met Leu Ala Gly Ser
1130                1135                1140

Glu Phe Asp Phe Ile Val Arg Tyr Phe Phe Ala Val Leu Ala Ile
1145                1150                1155

Leu Thr Ile Leu Gly Val Leu Asn Gly Leu Val Leu Leu Pro Val
1160                1165                1170
```

```
Leu Leu Ser Phe Phe Gly Pro Tyr Pro Glu Val Ser  Pro Ala Asn
    1175                1180                1185

Gly Leu Asn Arg Leu Pro Thr Pro Ser Pro Glu Pro  Pro Pro Ser
    1190                1195                1200

Val Val Arg Phe Ala Met Pro Pro Gly His Thr His  Ser Gly Ser
    1205                1210                1215

Asp Ser Ser Asp Ser Glu Tyr Ser Ser Gln Thr Thr  Val Ser Gly
    1220                1225                1230

Leu Ser Glu Glu Leu Arg His Tyr Glu Ala Gln Gln  Gly Ala Gly
    1235                1240                1245

Gly Pro Ala His Gln Val Ile Val Glu Ala Thr Glu  Asn Pro Val
    1250                1255                1260

Phe Ala His Ser Thr Val Val His Pro Glu Ser Arg  His His Pro
    1265                1270                1275

Pro Ser Asn Pro Arg Gln Gln Pro His Leu Asp Ser  Gly Ser Leu
    1280                1285                1290

Pro Pro Gly Arg Gln Gly Gln Pro Arg Arg Asp  Pro Pro Arg
    1295                1300                1305

Glu Gly Leu Trp Pro Pro Leu Tyr Arg Pro Arg Arg  Asp Ala Phe
    1310                1315                1320

Glu Ile Ser Thr Glu Gly His Ser Gly Pro Ser Asn  Arg Ala Arg
    1325                1330                1335

Trp Gly Pro Arg Gly Ala Arg Ser His Asn Pro Arg  Asn Pro Ala
    1340                1345                1350

Ser Thr Ala Met Gly Ser Ser Val Pro Gly Tyr Cys  Gln Pro Ile
    1355                1360                1365

Thr Thr Val Thr Ala Ser Ala Ser Val Thr Val Ala  Val His Pro
    1370                1375                1380

Pro Pro Val Pro Gly Pro Gly Arg Asn Pro Arg Gly  Gly Leu Cys
    1385                1390                1395

Pro Gly Tyr Pro Glu Thr Asp His Gly Leu Phe Glu  Asp Pro His
    1400                1405                1410

Val Pro Phe His Val Arg Cys Glu Arg Arg Asp Ser  Lys Val Glu
    1415                1420                1425

Val Ile Glu Leu Gln Asp Val Glu Cys Glu Glu Arg  Pro Arg Gly
    1430                1435                1440

Ser Ser Ser Asn
    1445

<210> SEQ ID NO 34
<211> LENGTH: 75
<212> TYPE: DNA
<213> ORGANISM: Homo sapiens

<400> SEQUENCE: 34
gctgctgctg ttcatcagcg tggtgttggc ctgcacattc ctcgtgtgcg ctgtcttcct    60
tctgaacccc tggac                                                    75

<210> SEQ ID NO 35
<211> LENGTH: 125
<212> TYPE: DNA
<213> ORGANISM: Homo sapiens

<400> SEQUENCE: 35
ctggggctgt ccagttaccc caacggctac cccttcctct tctgggagca gtacatcggc    60
```

```
ctccgccact ggctgctgct gttcatcagc gtggtgttgg cctgcacatt cctcgtgtgc    120
gctgt                                                                 125
```